(12) United States Patent
Frankel et al.

(10) Patent No.: US 6,316,003 B1
(45) Date of Patent: *Nov. 13, 2001

(54) TAT-DERIVED TRANSPORT POLYPEPTIDES

(75) Inventors: Alan Frankel, Tiburon, CA (US); Carl Pabo, Newton, MA (US); James G. Barsoum, Lexington, MA (US); Stephen E. Fawell, Winchester, MA (US); R. Blake Pepinsky, Arlington, MA (US)

(73) Assignees: Whitehead Institute for Biomedical Research, Cambridge, MA (US); Johns Hopkins Univ. School of Medicine, Baltimore, MD (US); Biogen, Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/235,403

(22) Filed: Apr. 28, 1994

Related U.S. Application Data

(63) Continuation-in-part of application No. 08/158,015, filed on Nov. 24, 1993, now abandoned, which is a continuation of application No. 07/636,662, filed on Jan. 2, 1991, now abandoned, which is a continuation-in-part of application No. 07/454,450, filed on Dec. 21, 1989, now abandoned, application No. PCT/US93/07833, filed on Aug. 19, 1993, and application No. 07/934,375, filed on Aug. 21, 1992, now abandoned.

(51) Int. Cl.$^7$ .................................................. A61K 39/12

(52) U.S. Cl. ................................ 424/196.11; 424/195.11; 424/194.1; 424/193.1; 424/192.1

(58) Field of Search ................................. 435/69.1, 91.1, 435/172.1, 252.3, 254.11; 424/196.1, 130.1, 195.11, 184.1, 194.1, 192.1, 192.11, 193.1, 208.1; 530/350, 324; 514/12, 2

(56) References Cited

U.S. PATENT DOCUMENTS

| | | | |
|---|---|---|---|
| 4,861,588 | 8/1989 | Neurath et al. | 424/89 |
| 4,918,166 | 4/1990 | Kingsman | 530/350 |
| 5,132,213 | 7/1992 | Bachmair et al. | 435/69 |
| 5,219,990 | 6/1993 | Androphy et al. | 530/350 |

FOREIGN PATENT DOCUMENTS

| | | | |
|---|---|---|---|
| 0 243 204 | 10/1987 | (EP) | C12N/7/00 |
| 0 302 758 | 6/1989 | (EP) | C12N/15/00 |
| 0 388758 | 9/1990 | (EP) | C12N/15/87 |
| 61-249277 | 5/1988 | (JP) | C12N/15/00 |
| WO 88/05077 | 7/1988 | (WO) | C12N/15/00 |
| WO 89/12461 | 12/1989 | (WO) | A61K/39/12 |
| WO 91/09958 | 7/1991 | (WO) | C12N/15/87 |
| WO 92/12728 | 6/1992 | (WO) | C12N/15/37 |

OTHER PUBLICATIONS

Endo et al, Virus Genes, vol. 3,(2), pp. 99–110, 1989.
E.J. Androphy et al., "Bovine Papillomavirus E2–Trans–Activating Gene Product Binds to Specific Sites in Papillomavirus DNA", *Nature*, 325, pp. 70–73 (1987).
S.K. Arya et al., "Trans–Activator Gene of Human T–Lymphotropic Virus Type III (HTLV–III)", *Science*, 229:69–73 (1985).
S.K. Arya and R.C. Gallo, "Three Novel Genes of Human T–Lymphotropic Virus Type III: Immune Reactivity of their Products with Sera from Acquired Immune Deficiency Syndrome Patients", *Proc. Natl. Acad. Sci. USA*, 83:2209–13 (1986).
S.K. Arya et al., "New Human and Simian HIV–Related Retroviruses Possess Functional Transactivator (tat) Gene", *Nature*, vol. 328, pp. 548–550 (1987).
J. Barsoum, "Introduction of Stable High–Copy–Number DNA into Chinese Hamster Ovary Cells by Electroporation", *DNA Cell Biol.*, 9, pp. 293–300 (1990).
J. Barsoum et al., "Mechanism of Action of the Papillomavirus E2 Repressor: Repression in the Absence of DNA Binding", *J. Virol.*, vol. 66, pp. 3941–3945 (1992).
R. Carroll et al., "Identification of Lentivirus Tat Functional Domains through Generation of Equine Infectious Anemia Virus/Human Immunodeficiency Virus Type 1 tat Gene Chimeras", *J. Virol.*, vol., 65, pp. 3460–3467 (1991).
R. Carroll et al., "Inhibition of Human Immunodeficiency Virus Type 1 Tat Activity by Coexpression of Heterologous trans Activators", *J. Virol.*, vol., 66, pp. 2000–2007 (1992).
R.L. Cate et al., "Isolation of the Bovine and Human Genes for Mullerian Inhibiting Substance and Expression of the Human Gene in Animal Cells", *Cell*, vol. 45, pp. 685–698 (1986).
L. Chakrabarti et al., "Sequence of Simian Immunodeficiency Virus from Macaque and Its Relationship to other Human and Simian Retroviruses", *Nature*, vol. 328, pp. 543–547 (1987).

(List continued on next page.)

*Primary Examiner*—Keith D. MacMillan
*Assistant Examiner*—T. D. Wessendorf

(57) ABSTRACT

This invention relates to delivery of biologically active cargo molecules, such as polypeptides and nucleic acids, into the cytoplasm and nuclei of cells in vitro and in vivo. Intracellular delivery of cargo molecules according to this invention is accomplished by the use of novel transport polypeptides which include HIV tat protein or one or more portions thereof, and which are covalently attached to cargo molecules. The transport polypeptides in preferred embodiments of this invention are characterized by the presence of the tat basic region (amino acids 49–57), the absence of the tat cysteine-rich region (amino acids 22–36) and the absence of the tat exon 2-encoded carboxy-terminal domain (amino acids 73–86) of the naturally-occurring tat protein. By virtue of the absence of the cysteine-rich region, the preferred transport polypeptides of this invention solve the potential problems of spurious trans-activation and disulfide aggregation. The reduced size of the preferred transport polypeptides of this invention also minimizes interference with the biological activity of the cargo molecule.

11 Claims, 16 Drawing Sheets

OTHER PUBLICATIONS

J. Choe et al., "Bovine Papillomavirus Type 1 Encodes Two Forms of a Transcriptional Repressor: Structural and Functional Analysis of New Viral cDNAs", *J. Virol.*, 63, pp. 1743–1755 (1989).

G. Chu et al., "Electroporation for the Efficient Transfection of Mammalian Cells with DNA", *Nuc. Acids Res.*, 15, pp. 1311–1326 (1987).

B.R. Cullen, "Trans–Activation of Human Immunodeficiency Virus Occurs Via A Bimodal Mechanism", *Cell*, 46:973–82 (1986).

C.V. Dang and W.M.F. Lee, "Nuclear and Nucleolar Targeting Sequences of c–erb–A, c–myb, N–myc, p53, HSP70, and HIV tat Proteins", *J.Biol.Chem.*, 264:18019–23 (1989).

N. Dostatni et al., A Dimer of BPV–1 E2 Containing a Protease Resistant Core Interacts with its DNA Target, *EMBO J.*, 7, pp. 3807–3816 (1988).

M. Durst et al., "A Papillomavirus DNA from a Cervical Carcinoma and Its prevalence in Cancer Biopsy Samples from Different Geographic Regions", *Proc. Natl. Acad. Sci. USA*, vol. 80, pp. 3812–3815 (1983).

B. Elangovan et al., "Functional Comparison of the Basic Domains of the Tat Proteins of Human Immunodeficiency Virus Types 1 and 2 in trans Activation", *J. Virol.*, vol., 66, pp. 2031–2036 (1992).

M. Emerman et al., "The Specificity of the Human Immunodeficiency Virus Type 2 Transactivator Is Different From That of Human Immunodeficiency Virus Type 1", *EMBO J.*, vol. 6, pp. 3755–3760 (1987).

H. Farhood et al., "Regulated Gene Transfer By Co–Delivery Of A Cis–Acting DNA Element And A Trans–Acting Protein Factor To Mammalian Cells With Cationic Liposomes", *J. Cell. Biochem.*, Supp 17E:242 (1993).

R. Fenrick et al., "Functional Analysis of the Tat trans Activator of Human Immunodeficiency Virus Type 2", *J. Virol.*, vol., 63, pp. 5006–5012 (1989).

A.D. Frankel et al., "Activity of Synthetic Peptides from the Tat Protein of Human Immunodeficiency Virus Type 1," *Proc. Natl. Acad. Sci. USA*, 86:7397–401 (1989).

A.D. Frankel and C.O. Pabo, "Cellular Uptake of the Tat Protein from Human Immunodeficiency Virus", *Cell*, 55:1189–93 (1988).

A.D. Frankel et al., "Tat Protein from Human Immunodeficiency Virus Forms a Metal–Linked Dimer," *Science*, 240:70–73 (1988).

A.D. Frankel et al., "Dimerization of the Tat Protein from Human Immunodeficiency Virus: A Cysteine–Rich Peptide Mimics the Normal Metal–Linked Dimer Interface", *Proc. Natl. Acad. Sci. USA*, 85:6297–300 (1988).

J.A. Garcia et al., "Functional Domains Required for Tat–induced Transcriptional Activation of the HIV–1 Long Terminal Repeat", *EMBO J.*, 7:3143–47 (1988).

I. Giri et al., "Study of the E2 Gene Product of the Cottontail Rabbit Papillomavirus Reveals a Common Mechanism of Transactivation Among Papillomaviruses", *J. Virol.*, 62, pp. 1573–1581 (1988b).

I. Giri et al., "Structural and Mutational Analysis of E2 Trans–Activating Proteins of Papillomaviruses Reveals Three Distinct Functional Domains", *EMBO J.*, 7, pp. 2823–2829 (1988a).

M. Green and P.M. Loewenstein, "Autonomous Functional Domains of Chemically Synthesized Human Immunodeficiency Virus Tat Trans–Activator Protein", *Cell*, 55:1179–88 (1988).

M. Green et al., "Mutational Analysis of HIV–1 Tat Minimal Domain Peptides: Identification of Trans–Dominant Mutants That Suppress HIV–LTR–Driven Gene Expression", *Cell*, 58:215–23 (1989).

M. Guyader et al., "Genome Organization and Transactivation of the Human Immunodeficiency Virus Type 2", *Nature*, vol. 326, pp. 662–669 (1987).

G.S. Harrison et al., "Toward HIV–Regulated Expression of A Diptheria Toxin A Gene In Transfected Cells", *J. Cell. Biochem.*, Supp. 13B:302 (1989).

J. Hauber et al., "Mutational Analysis of the Conserved Basic Domain of Human Immunodeficiency Virus tat Protein," *J. Virol.*, 63:1181–87 (1989).

T.H. Haugen et al. "Trans–Activation of an Upstream Early Gene Promoter of Bovine Papillomavirus–1 by a Product of the Viral E2 Gene", *EMBO J.*, 6, pp. 145–152 (1987).

T.H. Haugen et al., "Sequence–Specific and General Transcriptional Activation by the Bovine Papillomavirus–1 E2 trans–Activator Require an N–Terminal Amphipathic Helix–Containing E2 Domain", *EMBO J.*, 7. pp. 4245–4253 (1988).

P. Hawley–Nelson et al., "The Specific DNA Recognition Sequence of the Bovine Papillomavirus E2 Protein is an E2–Dependent Enhancer", *EMBO J.*, 7, pp. 525–531 (1988).

H. Hirochika et al., "Enhancers and trans–Acting E2 Transcriptional Factors of Papillomaviruses", *J. Virol.*, 61, pp. 2599–2606 (1987).

H. Hirochika et al., "Functional Mapping of the Human Papillomavirus Type 11 Transcriptional Enhancer and its Interaction with the trans–Acting E2 Proteins", *Genes Dev.*, 2, 54–67 (1988).

V. Hirsch et al., "The Genome Organization of STLV–3 is Similar to That of the AIDS Virus Except for a Truncated Transmembrane Protein", *Cell*, vol. 49, pp. 307–319 (1987).

P. Hoffmann et al., "Stimulation of Human and Murine Adherent Cells by Bacterial Lipoprotein and Synthetic Lipopeptide Analogues", *Immunobiol.*, vol. 177, pp. 158–170 (1988).

D. Kalderon et al., "A Short Amino Acid Sequence Able to Specify Nuclear Location," *Cell*, 39:499–509 (1984).

M. Kuppuswamy et al., "Multiple Functional Domains of Tat, the Trans–activator of HIV–1, Defined by Mutational Analysis", *Nuc. Acids Res.*, 17:3351–61 (1989).

P.F. Lambert et al., "Genetic Assignment of Multiple E2 Gene Products in Bovine Papillomavirus–Transformed Cells", *J. Virol.*, 63, pp. 3151–3154 (1989).

P.F. Lambert et al., "A Transcriptional Repressor Encoded by BPV–1 Shares a Common Carboxy–Terminal Domain with the E2 Transactivator", *Cell*, 50, pp. 69–78 (1987).

C.P. Leamon et al., "Delivery of Macromolecules Into Living Cells: A Method that Exploits Folate Receptor Endocytosis", *Proc. Nat. Acad. Sci. USA*, vol. 88, pp. 5572–5576 (1991).

R. Li et al., "Specific Recognition Nucleotides and Their DNA Context Determine the Affinity of E2 Protein for 17 Binding Sites in the BPV–1 Genome", *Genes Dev.*, 3, pp. 510–526 (1989).

D.A. Mann et al., "Endocytosis and Targeting of Exogenous HIV–1 Tat Protein", *EMBO J.*, vol. 10, pp. 1733–1739 (1991).

A.A. McBride et al., "E2 Polypeptides Encoded by Bovine Papillomavirus Type 1 Form Dimers through the Common Carboxyl–Terminal Domain: Transactivation is Mediated by the Conserved Amino–Terminal Domain", *Proc. Natl. Acad. Sci. USA*, 86, pp. 510–514 (1989).

A.A. McBride et al., "The Carboxy–Terminal Domain Shared by the Bovine Papillomavirus E2 Transactivator and Repressor Proteins Contains a Specific DNA Binding Activity", *EMBO J.*, 7, pp. 533–539 (1988).

I.J. Mohr et al., "Targeting the E1 Replication Protein to the Papillomavirus Origin of Replication by Complex Formation with the E2 Transactivator", *Science*, 250, pp. 1694–1699 (1990).

L.C. Morrissey et al., "trans–Activation by the Bovine Papillomavirus E2 Protein in *Saccharomyces cerevisiae*", *J. Virol.*, 63, pp. 4422–4425 (1989).

C. Moskaluk et al., "The E2 'Gene' of Bovine Papillomavirus Encodes an Enhancer Binding Protein", *Proc. Natl. Acad. Sci. USA*, 84, pp. 1215–1218 (1987).

C. Moskaluk et al., "Interaction of the Bovine Papillomavirus Type 1 E2 Transcriptional Control Protein with the Viral Enhancer: Purification of the DNA–Binding Domain and Analysis of Its Contact Points with DNA", *J. Virol.*, 62, pp. 1925–1931 (1988a).

C. Moskaluk et al., "The Bovine Papillomavirus Type 1 Transcriptional Activator E2 Protein Binds to Its DNA Recognition Sequence as a Dimer", *Virology*, 169, pp. 236–238 (1989).

C. Moskaluk et al., "DNA Bending is Induced in an Enhancer by the DNA–Binding Domain of the Bovine Papillomavirus E2 Protein", *Proc. Natl. Acad. Sci. USA*, 85, pp. 1826–1830 (1988b).

M.A. Muesing et al., "Regulation of mRNA Accumulation by a Human Immunodeficiency Virus Trans–Activator Protein", *Cell*, 48:691–701 (1987).

L. Pearson et al., "A Transdominant tat Mutant that Inhibits Tat–Induced Gene Expression From The Human Immunodeficiency Virus Long Terminal Repeat", *Proc. Natl. Acad. Sci. USA*, 87:5079–83 (1990).

T.I. Prior et al., "Barnase Toxin: A New Chimeric Toxin Composed of Pseudomonas Exotoxin A and Barnase", *Cell*, vol. 64, pp. 1017–1023 (1991).

J. Rappaport et al., "The Acidic Amino–Terminal Region of the HIV–1 Tat Protein Constitutes an Essential Activating Domain", *New Biologist*, 1:101–10 (1989).

A.P. Rice and F. Carlotti, "Mutational Analysis of the Conserved Cysteine–Rich Region of the Human Immunodeficiency Virus Type 1 Tat Protein", *J. Virol.*, 64:1864–68 (1990).

S. Ruben et al., "Structural and Functional Characterization of Human Immunodeficiency Virus tat Protein," *J. Virol.*, 63:1–8 (1989).

L.J. Seigel et al., "Transactivation Induced by Human T–Lymphotropic Virus Type III (HTLV III) Maps to a Viral Sequence Encoding 58 Amino Acids and Lacks Tissue Specificity", *Virology*, 148:226–31 (1986).

A. Seiler–Tuyns et al., "Expression and Regulation of Chicken Actin Genes Introduced into Mouse Myogenic and Nonmyogenic Cells", *Proc. Natl. Acad. Sci. USA*, 81, pp. 2980–2984 (1984).

W.C. Shen and H.J.–P. Ryser, "Conjugation of poly–L–l-ysine to Albumin and Horseradish Peroxidase: A Novel Method of Enhancing the Cellular Uptake of Proteins", *Proc. Natl. Acad. Sci. USA*, 75, pp. 1872–1876 (1978).

H. Siomi et al., "Effects of a Highly Basic Region of Human Immunodeficiency Virus Tat Protein on Nucleolar Localization", *J. Virol.*, 64:1803–07 (1990).

J. Sodroski et al., "Trans–Acting Transcriptional Regulation of Human T–Cell Leukemia Virus Type III Long Terminal Repeat", *Science*, vol. 227, pp. 171–173 (1985).

J. Sodroski et al., "Location of the Trans–Activating Region on the Genome of Human T–Cell Lymphotropic Virus Type III", *Science*, 229:74–77 (1985).

B.A. Spalholz et al., "Bovine Papillomavirus Transcriptional Regulation: Localization of the E2–Responsive Elements of the Long Control Region", *J. Virol.*, 61, pp. 2128–2137 (1987).

B.A. Spalholz et al., "Transactivation of a Bovine Papilloma Virus Transcriptional Regulatory Element by the E2 Gene Product", *Cell*, 42, pp. 183–191 (1985).

J.C. Stavridis and M. Psallidopoulos, "Use of Transferrin as a Gene–Carrier to the Erythroid Cells of the Marrow", *Cell. Mol. Biol.*, 28:15–18 (1982).

A. Stenlund et al., "The E2 trans–Activator Can Act as a Repressor by Interfering with a Cellular Transcription Factor", *Genes Dev.*, 4, pp. 123–136 (1990).

L.A. Sternson, "Obstacles to Polypeptide Delivery" *Ann. N.Y. Acad. Sci.*, pp. 19–21 (1987).

F.W. Studier and B.A. Moffett, "Use of Bacteriophage T7 RNA Polymerase to Direct Selective High–Level Expression of Cloned Genes", *J. Mol. Biol.*, 189:113–30 (1986).

L.S. Tiley et al., "Does the Human Immunodeficiency Virus trans–Activator Contain a Discrete Activation Domain?", *Virology*, 178:560–67 (1990).

R.P. Viscidi et al., "Inhibition of Antigen–Induced Lymphocyte Proliferation by Tat Protein from HIV–1", *Science*, 246:1606–08 (1989).

S. Wain–Hobson et al., "Nucleotide Sequence of the AIDS Virus, LAV", *Cell*, 40:9–17 (1985).

G. Winkler et al., "CD4–Pseudomonas Exotoxin Hybrid Proteins: Modulation of Potency and Therapeutic Window Through Structural Design and Characterization of Cell Internalization", *AIDS Res. Hum. Retroviruses*, vol. 7, pp. 393–401 (1991).

G.Y. Wu et al., "Delivery Systems for Gene Therapy", *Biotherapy*, vol. 3, pp. 87–95 (1991).

```
Met Glu Pro Val Asp Pro Arg Leu Glu Pro Trp Lys His Pro Gly
 1               5                  10                  15

Ser Gln Pro Lys Thr Ala Cys Thr Asn Cys Tyr Cys Lys Lys Cys
                20                  25                  30

Cys Phe His Cys Gln Val Cys Phe Ile Thr Lys Ala Leu Gly Ile
                35                  40                  45

Ser Tyr Gly Arg Lys Lys Arg Arg Gln Arg Arg Arg Pro Pro Gln
                50                  55                  60

Gly Ser Gln Thr His Gln Val Ser Leu Ser Lys Gln Pro Thr Ser
                65                  70                  75

Gln Ser Arg Gly Asp Pro Thr Gly Pro Lys Glu
                80                  85
```

FIG. 1

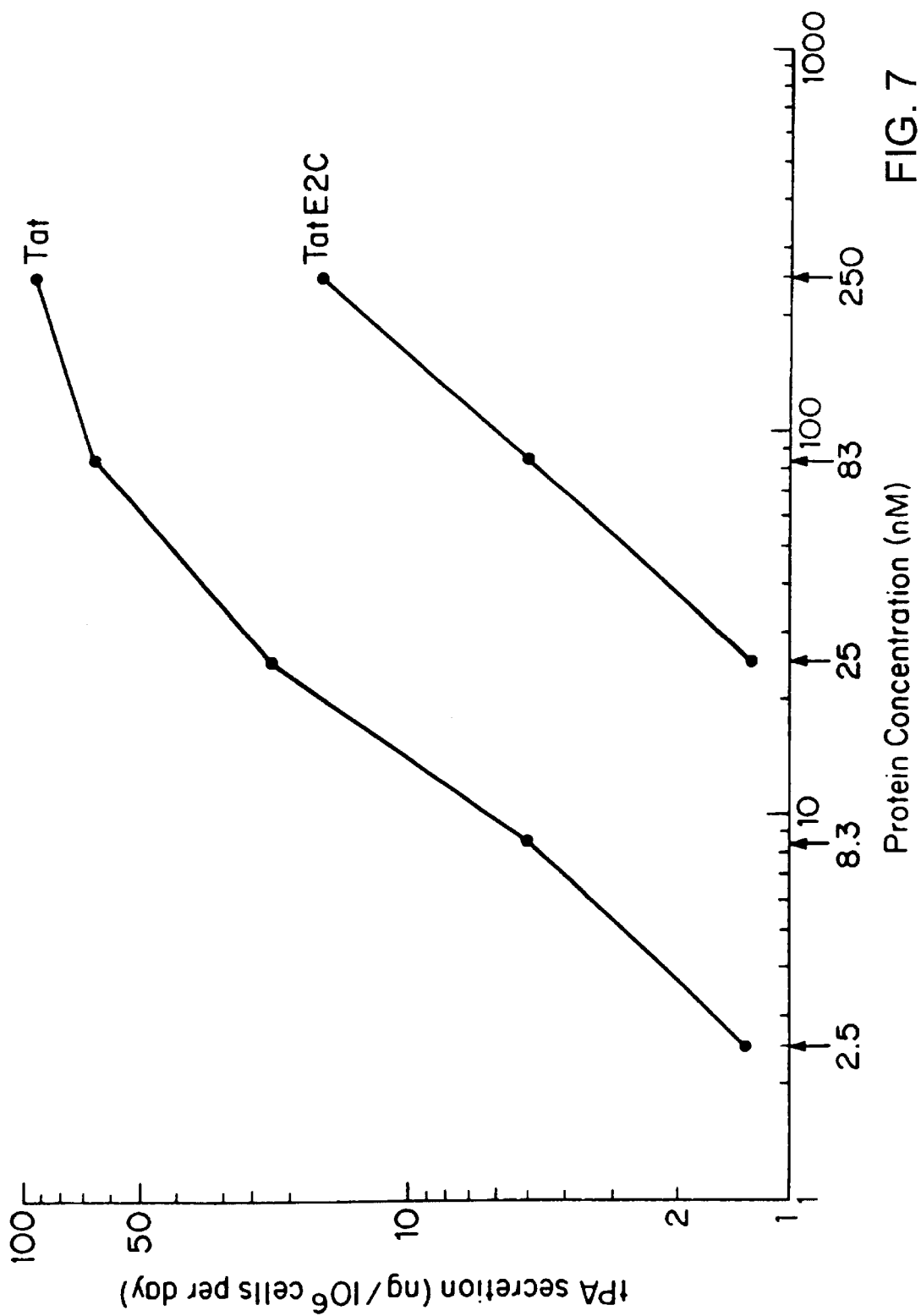

*MET* TYR GLY ARG LYS LYS ARG ARG GLN ARG ARG
 47

ARG PRO PRO ASP THR GLY ASN PRO CYS HIS THR THR
 58  245

LYS LEU LEU HIS ARG ASP SER VAL ASP SER ALA PRO
255

ILE LEU THR ALA PHE ASN SER SER HIS LYS GLY ARG
267

ILE ASN CYS ASN SER ASN THR THR PRO ILE VAL HIS
279

LEU LYS GLY ASP ALA ASN THR LEU LYS CYS LEU ARG
291

TYR ARG PHE LYS LYS HIS CYS THR LEU TYR THR ALA
303

VAL SER SER THR TRP HIS TRP THR GLY HIS ASN VAL
315

LYS HIS LYS SER ALA ILE VAL THR LEU THR TYR ASP
327

SER GLU TRP GLN ARG ASP GLN PHE LEU SER GLN VAL
339

LYS ILE PRO LYS THR ILE THR VAL SER THR GLY PHE
351
     365
MET SER ILE

FIG. 18

TAT-DERIVED TRANSPORT POLYPEPTIDES

This application is a continuation-in-part of copending application Ser. No. 08/158,015, filed Nov. 24, 1993 now abandoned, which is a file wrapper continuation of Ser. No. 07/636,662, filed Jan. 2, 1991, now abandoned, which is a continuation-in-part of Ser. No. 07/454,450, filed Dec. 21, 1989, now abandoned, and also a continuation-in-part of PCT/US93/07833, filed Aug. 19, 1993, designating the United States and claiming priority from and a continuation-in-part Ser. No. 07/934,375, filed Aug. 21, 1992, now abandoned.

Work described herein was supported, in part, by the National Institutes of Health, Whitehead Institute for Biomedical Research, Howard Hughes Medical Institute and Johns Hopkins University School of Medicine.

TECHNICAL FIELD OF THE INVENTION

This invention relates to delivery of biologically active cargo molecules, such as polypeptides and nucleic acids, into the cytoplasm and nuclei of cells in vitro and in vivo. Intracellular delivery of cargo molecules according to this invention is accomplished by the use of novel transport polypeptides which comprise HIV tat protein or one or more portions thereof, and which are covalently attached to cargo molecules. The transport polypeptides in preferred embodiments of this invention are characterized by the presence of the tat basic region (amino acids 49–57), the absence of the tat cysteine-rich region (amino acids 22–36) and the absence of the tat exon 2-encoded carboxy-terminal domain (amino acids 73–86) of the naturally-occurring tat protein. By virtue of the absence of the cysteine-rich region, the preferred transport polypeptides of this invention solve the potential problems of spurious trans-activation and disulfide aggregation. The reduced size of the preferred transport polypeptides of this invention also minimizes interference with the biological activity of the cargo molecule.

BACKGROUND OF THE INVENTION

Biological cells are generally impermeable to macromolecules, including proteins and nucleic acids. Some small molecules enter living cells at very low rates. The lack of means for delivering macromolecules into cells in vivo has been an obstacle to the therapeutic, prophylactic and diagnostic use of a potentially large number of proteins and nucleic acids having intracellular sites of action. Accordingly, most therapeutic, prophylactic and diagnostic candidates produced to date using recombinant DNA technology are polypeptides that act in the extracellular environment or on the target cell surface.

Various methods have been developed for delivering macromolecules into cells in vitro. A list of such methods includes electroporation, membrane fusion with liposomes, high velocity bombardment with DNA-coated microprojectiles, incubation with calcium-phosphate-DNA precipitate, DEAE-dextran mediated transfection, infection with modified viral nucleic acids, and direct micro-injection into single cells. These in vitro methods typically deliver the nucleic acid molecules into only a fraction of the total cell population, and they tend to damage large numbers of cells. Experimental delivery of macromolecules into cells in vivo has been accomplished with scrape loading, calcium phosphate precipitates and liposomes. However, these techniques have, to date, shown limited usefulness for in vivo cellular delivery. Moreover, even with cells in vitro, such methods are of extremely limited usefulness for delivery of proteins.

General methods for efficient delivery of biologically active proteins into intact cells, in vitro and in vivo, are needed. (L. A. Sternson, "Obstacles to Polypeptide Delivery", Ann. N.Y. Acad. Sci, 57, pp. 19–21 (1987)). Chemical addition of a lipopeptide (P. Hoffmann et al., "Stimulation of Human and Murine Adherent Cells by Bacterial Lipoprotein and Synthetic Lipopeptide Analogues", Immunobiol., 177, pp. 158–70 (1988)) or a basic polymer such as polylysine or polyarginine (W-C. Chen et al., "Conjugation of Poly-L-Lysine Albumin and Horseradish Peroxidase: A Novel Method of Enhancing the Cellular Uptake of Proteins", Proc. Natl. Acad. Sci. USA, 75, pp. 1872–76 (1978)) have not proved to be highly reliable or generally useful (see Example 4 infra,). Folic acid has been used as a transport moiety (C. P. Leamon and Low, Delivery of Macromolecules into Living Cells: A Method That Exploits Folate Receptor Endocytosis", Proc. Natl. Acad. Sci USA, 88, pp. 5572–76 (1991)). Evidence was presented for internalization of folate conjugates, but not for cytoplasmic delivery. Given the high levels of circulating folate in vivo, the usefulness of this system has not been fully demonstrated. Pseudomonas exotoxin has also been used as a transport moiety (T. I. Prior et al., "Barnase Toxin: A New Chimeric Toxin Composed of Pseudomonas Exotoxin A and Barnase", Cell, 64, pp. 1017–23 (1991)). The efficiency and general applicability of this system for the intracellular delivery of biologically active cargo molecules is not clear from the published work, however.

Purified human immunodeficiency virus type-1 ("HIV") tat protein is taken up from the surrounding medium by human cells growing in culture (A. D. Frankel and C. O. Pabo, "Cellular Uptake of the Tat Protein from Human Immunodeficiency Virus", Cell, 55, pp. 1189–93 (1988)). Tat protein trans-activates certain HIV genes and is essential for viral replication. The full-length HIV-1 tat protein has 86 amino acid residues. The HIV tat gene has two exons. Tat amino acids 1–72 are encoded by exon 1, and amino acids 73–86 are encoded by exon 2. The full-length tat protein is characterized by a basic region which contains two lysines and six arginines (amino acids 49–57) and a cysteine-rich region which contains seven cysteine residues (amino acids 22–37).

The basic region (i.e., amino acids 49–57) is thought to be important for nuclear localization. Ruben, S. et al., J. Virol. 63: 1–8 (1989); Hauber, J. et al., J. Virol. 63 1181–1187 (1989). The cysteine-rich region mediates the formation of metal-linked dimers in vitro (Frankel, A. D. et al, Science 240: 70–73 (1988); Frankel, A. D. et al., Proc. Natl. Acad. Sci USA 85: 6297–6300 (1988)) and is essential for its activity as a transactivator (Garcia, J. A. et al., EMBO J. 7:3143 (1988); Sadaie, M. R. et al., J. Virol. 63: 1 (1989)). As in other regulatory proteins, the N-terminal region may be involved in protection against intracellular proteases (Bachmair, A. et al., Cell 56: 1019–1032 (1989)).

At the present time, the need exists for generally applicable means for safe, efficient delivery of biologically active molecule of interest or cargo molecules into the cytoplasm and nuclei of living cells.

SUMMARY OF THE INVENTION

The present invention relates to the use of HIV tat protein, or a tat-derived polypeptide, to deliver a molecule of interest or cargo molecule into eukaryotic cells, particularly into the cell nucleus, in vitro or in vivo. It further relates to conjugates that include an HIV tat protein and a molecule of interest, or a tat-derived polypeptide and a cargo molecule, which are useful in the method of the present invention for delivering biologically active molecules into the cytoplasm and nuclei of cells.

More particularly, this invention provides processes and products for the efficient cytoplasmic and nuclear delivery of biologically active non-tat proteins, nucleic acids and other molecules that are (1) not inherently capable of entering target cells or cell nuclei, or (2) not inherently capable of entering target cells at a useful rate. Intracellular delivery of cargo molecules according to this invention is accomplished by the use of novel transport proteins which comprise one or more portions of HIV tat protein and which are covalently attached to the cargo molecules. According to various embodiments, this invention relates to novel transport polypeptides, methods for making those transport polypeptides, transport polypeptide-cargo conjugates, pharmaceutical, prophylactic and diagnostic compositions comprising transport polypeptide-cargo conjugates, and methods for delivery of cargo into cells by means of tat-derived transport polypeptides.

The preferred transport polypeptides of this invention are characterized by the presence of the tat basic region amino acid sequence (amino acids 49–57 of naturally-occurring tat protein); the absence of the tat cysteine-rich region amino acid sequence (amino acids 22–36 of naturally-occurring tat protein) and the absence of the tat exon 2-encoded carboxy-terminal domain (amino acids 73–86 of naturally-occurring tat protein). Preferred embodiments of such transport polypeptides are: tat37-72 (SEQ ID NO:2), tat37-58 (SEQ ID NO:3), tat38-58GGC (SEQ ID NO:4), tatCGG47-58 (SEQ ID NO:5) tat47-58GGC (SEQ ID NO:6), and tatΔcys (SEQ ID NO:7). It will be recognized by those of ordinary skill in the art that when the transport polypeptide is genetically fused to the cargo moiety, an amino-terminal methionine must be added, but the spacer amino acids (e.g., CysGlyGly or GlyGlyCys) need not be added.

By virtue of the absence of the cysteine-rich region present in conventional tat proteins, the preferred transport polypeptides of this invention solve the problem of disulfide aggregation, which can result in loss of the cargo's biological activity, insolubility of the transport polypeptide-cargo conjugate, or both. The reduced size of the preferred transport polypeptides of this invention also advantageously minimizes interference with the biological activity of the cargo. A further advantage of the reduced transport polypeptide size is enhanced uptake efficiency in embodiments of this invention involving attachment of multiple transport polypeptides per cargo molecule.

Transport polypeptides of this invention may be advantageously attached to cargo molecules by chemical cross-linking or by genetic fusion. A unique terminal cysteine residue is a preferred means of chemical cross-linking. According to some preferred embodiments of this invention, the carboxy terminus of the transport moiety is genetically fused to the amino terminus of the cargo moiety. A particularly preferred embodiment of the present invention is JB106, which consists of an amino-terminal methionine followed by tat residues 47-58, followed by HPV-16 E2 residues 245–365.

According to one preferred embodiment of this invention, a biologically active cargo is delivered into the cells of various organs and tissues following introduction of a transport polypeptide-cargo conjugate into a live human or animal. By virtue of the foregoing features, this invention opens the way for biological research and disease therapy involving proteins, nucleic acids and other molecules with cytoplasmic or nuclear sites of action.

BRIEF DESCRIPTION OF THE DRAWINGS

FIG. 1 depicts the amino acid sequence of HIV-1 tat protein (SEQ ID NO:1).

FIG. 7 summarizes data on transactivation of a tPA reporter gene under the control of the HIV-1 LTR in HeLa.318 cells upon addition of exogenous tat protein or a tatE2C fusion protein.

FIG. 18 depicts the complete amino acid sequence of protein JB106.

DETAILED DESCRIPTION OF THE INVENTION

Figure 2:
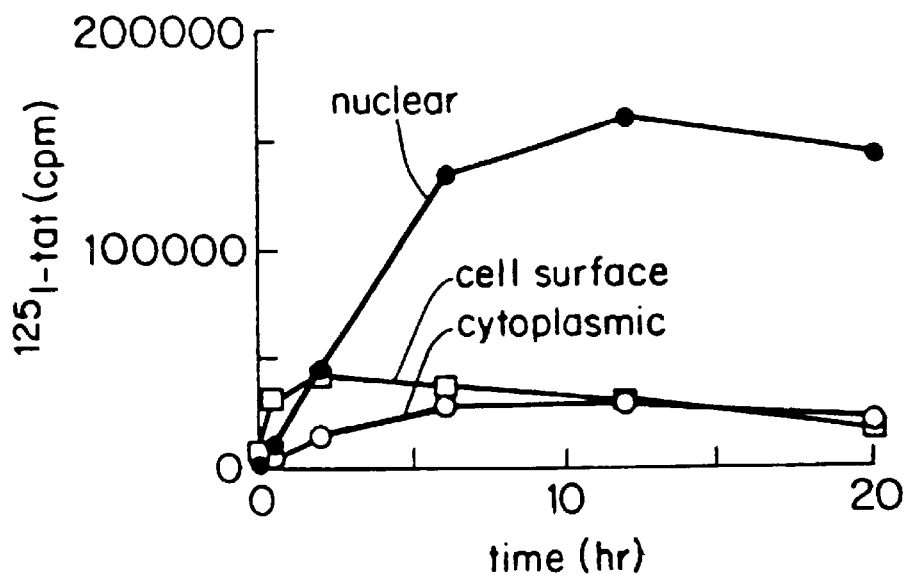
FIG. 2 graphically depicts the cellular uptake and nuclear localization of $^{125}$I-labeled tat protein.

In order that the invention herein described may be more fully understood, the following detailed description is set forth.

In the description, the following terms are employed:

Amino acid—A monomeric unit of a peptide, polypeptide or protein. The twenty protein amino acids (L-isomers) are: alanine ("Ala" or "A"), arginine ("Arg" or "R"), asparagine ("Asn" or "N"), aspartic acid ("Asp" or "D"), cysteine ("Cys" or "C"), glutamine ("Gln" or "Q"), glutamic acid ("Glu" or "E"), glycine ("Gly" or "G"), histidine ("His" or "H"), isoleucine ("Ile" or "I"), leucine ("Leu" or "L"), lysine ("Lys" or "K"), methionine ("Met" or "M"), phenylalanine ("Phe" or "F"), proline ("Pro" or "P"), serine ("Ser" or "S"), threonine ("Thr" or "T"), tryptophan ("Trp" or "W"), tyrosine ("Tyr" or "Y") and valine ("Val" or "V"). The term amino acid, as used herein, also includes analogs of the protein amino acids, and D-isomers of the protein amino acids and their analogs.

Cargo—A molecule that is not a tat protein or a fragment thereof, and that is either (1) not inherently capable of entering target cells, or (2) not inherently capable of entering target cells at a useful rate. ("Cargo", as used in this application, refers either to a molecule, per se, i.e., before conjugation, or to the cargo moiety of a transport polypeptide-cargo conjugate.) Examples of "cargo" include, but are not limited to, small molecules and macromolecules, such as polypeptides, nucleic acids and polysaccharides.

Chemical cross-linking—Covalent bonding of two or more pre-formed molecules.

Cargo conjugate—A molecule comprising at least one transport polypeptide moiety and at least one cargo moiety, formed either through genetic fusion or chemical cross-linking of a transport polypeptide and a cargo molecule.

Genetic fusion—Co-linear, covalent linkage of two or more proteins via their polypeptide backbones, through genetic expression of a DNA molecule encoding those proteins.

Macromolecule—A molecule, such as a peptide, polypeptide, protein or nucleic acid.

Molecule of interest—See definition of cargo, above.

Polypeptide—Any polymer consisting essentially of any of the 20 protein amino acids (above), regardless of its size. Although "protein" is often used in reference to relatively large polypeptides, and "peptide" is often used in reference to small polypeptides, usage of these terms in the art overlaps and varies. The term "polypeptide" as used herein refers to peptides, polypeptides and proteins, unless otherwise noted.

Reporter gene—A gene the expression of which depends on the occurrence of a cellular event of interest, and the expression of which can be conveniently observed in a genetically transformed host cell.

Reporter plasmid—A plasmid vector comprising one or more reporter genes.

Small molecule—A molecule other than a macromolecule.

Spacer amino acid—An amino acid (preferably having a small side chain) included between a transport moiety and an amino acid residue used for chemical cross-linking (e.g., to provide molecular flexibility and avoid steric hindrance).

Target cell—A cell into which a cargo is delivered by a transport polypeptide. A "target cell" may be any cell, including human cells, either in vivo or in vitro.

Transport moiety or transport polypeptide—A polypeptide capable of delivering a covalently attached cargo into a target cell, e.g., tat protein or a tat-derived polypeptide.

The present invention is based on the unexpected finding that when tat protein from immunodeficiency virus (e.g., HIV-1, HIV-2, SIV) is present extracellularly, it is readily taken up into cells and subsequently into the cell nucleus. This is evidenced by the fact that when cultured cells with an integrated HIV-1 promoter are treated with tat in the medium, they exhibit high levels of transactivation of the HIV-1 promoter. In light of the fact that proteins and peptides are typically poorly taken up (Sternson, L. A., *Ann. N.Y. Acad. Sci.* 57:19–21 (1987)), the finding that tat is readily taken up into cells is surprising.

As a result of this finding, it is now possible to use tat protein to deliver molecules (e.g., proteins, peptides, nucleic acids) into cells and, specifically, into the cell nucleus. The present invention relates to a method of delivering a molecule of interest into cells and, particularly, of targeting a molecule to the cell nucleus, as well as a conjugate useful in the method. Any molecule can be delivered into cells, especially into the cell nucleus, using the method of the subject invention. For example, in one embodiment of the present method, the molecule to be delivered into cells is a protein, a peptide or an oligonucleotide. The present invention is particularly useful for delivery of proteins or peptides, such as regulatory factors, enzymes, antibodies, drugs or toxins, as well as DNA or RNA, into the cell nucleus.

A stabilizing agent, which serves to increase tat stability and uptake, can be brought into contact with cells, in conjunction with the molecule of interest and tat protein. For example, metal ions which bind to tat protein and increase its stability and uptake, can be used for this purpose.

In a further embodiment of this invention, a lysosomotrophic agent is provided extracellularly in conjunction with tat protein and a molecule of interest, in order to enhance uptake by cells. The lysosomotrophic agent can be used alone or in conjunction with a stabilizer. For example, lysosomotrophic agents such as chloroquine, monensin, amantadine and methylamine, which have been shown to increase uptake of tat in some cells by a few hundred fold, can be used for this purpose.

In another embodiment, a basic peptide, such as tat 38-58 or protamine, is provided extracellularly with tat and a molecule of interest to enhance uptake of Tat. Such basic peptides can also be used alone, in combination or with stabilizing agents or lysosomotrophic agents.

In one embodiment of the present invention, a molecule of interest-tat protein conjugate, which includes a molecule of interest (i.e., a molecule to be introduced into cells) attached to HIV tat protein, is brought into contact with cells into which introduction of the molecule of interest is desired, under conditions appropriate for its entry into cells. As a result, the conjugate enters into cells, passing into the nucleus.

The present invention may be used to deliver a molecule of interest either in vitro or in vivo. For example, delivery can be carried out in vitro by adding a molecule of interest-tat conjugate to cultured cells, by producing cells that synthesize tat or tat conjugate or by combining a sample (e.g., blood, bone marrow) obtained from an individual with the conjugate, under appropriate conditions. Thus, the target cells may be in vitro cells, i.e., cultured animal cells, human cells or micro-organisms. Delivery can be carried out in vivo by administering the molecule of interest and tat protein to an individual in whom it is to be used for diagnostic, preventative or therapeutic purposes. The target cells may be in vivo cells, i.e., cells composing the organs or tissues of living animals or humans, or microorganisms found in living animals or humans.

This invention is generally applicable for therapeutic, prophylactic or diagnostic intracellular delivery of small molecules and macromolecules, such as proteins, nucleic acids and polysaccharides, that are not inherently capable of entering target cells at a useful rate. It should be appreciated, however, that alternate embodiments of this invention are not limited to clinical applications. This invention may be advantageously applied in medical and biological research. In research applications of this invention, the cargo may be a drug or a reporter molecule. Transport polypeptides of this invention may be used as research laboratory reagents, either alone or as part of a transport polypeptide conjugation kit.

Wide latitude exists in the selection of drugs and reporter molecules for use in the practice of this invention. Factors to be considered in selecting reporter molecules include, but are not limited to, the type of experimental information sought, non-toxicity, convenience of detection, quantifiability of detection, and availability. Many such reporter molecules are known to those skilled in the art.

As will be appreciated from the examples presented below, we have used enzymes for which calorimetric assays exist, as model cargo to demonstrate the operability and useful features of the transport polypeptides of this invention. These enzyme cargos provide for sensitive, convenient, visual detection of cellular uptake. Furthermore, since visual readout occurs only if the enzymatic activity of the cargo is preserved, these enzymes provide a sensitive and reliable test for preservation of biological activity of the cargo moiety in transport polypeptide-cargo conjugates according to this invention. A preferred embodiment of this invention comprises horseradish peroxidase ("HRP") as the cargo moiety of the transport polypeptide-cargo conjugate. A particularly preferred model cargo moiety for practice of this invention is β-galactosidase.

Model cargo proteins may also be selected according to their site of action within the cell. As described in Examples 6 and 7, below, we have used the ADP ribosylation domain from Pseudomonas exotoxin ("PE") and pancreatic ribonuclease to confirm cytoplasmic delivery of a properly folded cargo proteins by transport polypeptides according to this invention.

Full-length Pseudomonas exotoxin is itself capable of entering cells, where it inactivates ribosomes by means of an ADP ribosylation reaction, thus killing the cells. A portion of the Pseudomonas exotoxin protein known as the ADP ribosylation domain is incapable of entering cells, but it retains the ability to inactivate ribosomes if brought into contact with them. Thus, cell death induced by transport polypeptide-PE ADP ribosylation domain conjugates is a test for cytoplasmic delivery of the cargo by the transport polypeptide.

We have also used ribonuclease to confirm cytoplasmic delivery of a properly folded cargo protein by transport polypeptides of this invention. Protein synthesis, an RNA-dependent process, is highly sensitive to ribonuclease, which digests RNA. Ribonuclease is, by itself, incapable of entering cells, however. Thus, inhibition of protein synthesis by a transport polypeptide-ribonuclease conjugate is a test for intracellular delivery of biologically active ribonuclease.

Of course, delivery of a given cargo molecule to the cytoplasm may be followed by further delivery of the same cargo molecule to the nucleus. Nuclear delivery necessarily involves traversing some portion of the cytoplasm.

Papillomavirus E2 repressor proteins are examples of macromolecular drugs that may be delivered into the nuclei of target cells by the transport polypeptides of this invention. Papillomavirus E2 protein, which normally exists as a homodimer, regulates both transcription and replication of the papillomavirus genome. The carboxy-terminal domain of the E2 protein contains DNA binding and dimerization activities. Transient expression of DNA sequences encoding various E2 analogs or E2 carboxy-terminal fragments in transfected mammalian cells inhibits trans-activation by the full-length E2 protein (J. Barsoum et al., "Mechanism of Action of the Papillomavirus E2 Repressor: Repression in the Absence of DNA Binding", *J. Virol.*, 66, pp. 3941–3945 (1992)). E2 repressors added to the growth medium of cultured mammalian cells do not enter the cells, and thus do not inhibit E2 trans-activation in those cells. However, conjugation of the transport polypeptides of this invention to E2 repressors results in translocation of the E2 repressors from the growth medium into the cultured cells, where they display biological activity, repressing E2-dependent expression of a reporter gene.

The rate at which single-stranded and double-stranded nucleic acids enter cells, in vitro and in vivo, may be advantageously enhanced, using the transport polypeptides of this invention. As shown in Example 11 (below), methods for chemical cross-linking of polypeptides to nucleic acids are well known in the art. In a preferred embodiment of this invention, the cargo is a single-stranded antisense nucleic acid. Antisense nucleic acids are useful for inhibiting cellular expression of sequences to which they are complementary. In another embodiment of this invention, the cargo is a double-stranded nucleic acid comprising a binding site recognized by a nucleic acid-binding protein. An example of such a nucleic acid-binding protein is a viral trans-activator.

It will be appreciated that the entire 86 amino acids which make up the tat protein may not be required for the uptake activity of tat. For example, a protein fragment or a peptide which has fewer than the 86 amino acids, but which exhibits uptake into cells and uptake into the cell nucleus, can be used (a functionally effective fragment or portion of tat). As is shown in the Examples below, tat protein containing residues 1–72 is sufficient for uptake activity and tat residues 1–67 are shown to mediate the entry of a heterologous protein into cells. In addition, a synthetic peptide containing tat residues 1–58 has now been shown to have uptake activity. A tat peptide comprising the region that mediates entry and uptake into cells can be further defined using known techniques (see, e.g., Frankel, A. D., et al., *Proc. Natl. Acad. Sci, USA* 86:7397–7401 (1989)).

The tat peptide can be a single (i.e., continuous) amino acid sequence present in tat protein or it can be two or more amino acid sequences which are present in tat protein, but in the naturally-occurring protein are separated by other amino acid sequences. As used herein, tat protein includes a naturally-occurring amino acid sequence which is the same as that of naturally-occurring tat protein, its functional equivalent or functionally equivalent fragments thereof (peptides). Such functional equivalents or functionally equivalent fragments possess uptake activity into the cell and into the cell nucleus that is substantially similar to that of naturally-occurring tat protein. Tat protein can be obtained from naturally-occurring sources or can be produced using genetic engineering techniques or chemical synthesis.

The amino acid sequence of naturally-occurring HIV tat protein can be modified, by addition, deletion and/or substitution of at least one amino acid present in the naturally-occurring tat protein, to produce modified tat protein (also referred to herein as tat protein). Modified tat protein or tat peptide analogs with increased stability can thus be produced using known techniques. Therefore, tat proteins or peptides may have amino acid sequences which are substantially similar, although not identical, to that of naturally-occurring tat protein or portions thereof. In addition, cholesterol or other lipid derivatives can be added to tat protein to produce a modified tat having increased membrane solubility.

Variants of tat protein can be designed to modulate the intracellular location of tat and the molecule of interest following uptake into the cell or when expressed in the cell. When added exogenously, such variants are designed such that the ability of tat to enter cells is retained (i.e., the uptake of the variant tat protein or peptide into the cell is substantially similar to that of naturally-occurring HIV tat). For example, alteration of the basic region thought to be important for nuclear localization (see e.g., Dang, C. V. and Lee, W. M. F., *J. Biol. Chem.* 264:18019–18023 (1989); Hauber, J. et al., *J. Virol.* 63:1181–1187 (1989); Ruben, S. A. et al., *J. Virol.* 63:1–8 (1989)) can result in a cytoplasmic location or partially cytoplasmic location of tat, and therefore, of the molecule of interest. Alternatively, a sequence for binding a cytoplasmic component can be introduced into tat in order to retain tat and the molecule of interest in the cytoplasm or to confer regulation upon nuclear uptake of tat and the molecule of interest.

Naturally-occurring HIV-1 tat protein (FIG. 1) has a region (amino acids 22–37) wherein 7 out of 16 amino acids are cysteine. Those cysteine residues are capable of forming disulfide bonds with each other, with cysteine residues in the cysteine-rich region of other tat protein molecules and with cysteine residues in a cargo protein or the cargo moiety of a conjugate. Such disulfide bond formation can cause loss of the cargo's biological activity. Furthermore, even if there is no potential for disulfide bonding to the cargo moiety (for example, when the cargo protein has no cysteine residues), disulfide bond formation between transport polypeptides leads to aggregation and insolubility of the transport polypeptide, the transport polypeptide-cargo conjugate, or both. The tat cysteine-rich region is potentially a source of serious problems in the use of naturally-occurring tat protein for cellular delivery of cargo molecules.

The cysteine-rich region is required for dimerization of tat in vitro, and is required for trans-activation of HIV DNA sequences. Therefore, removal of the tat cysteine-rich region has the additional advantage of eliminating the natural activity of tat, i.e., induction of HIV transcription and replication. However, the art does not teach whether the cysteine-rich region of the tat protein is required for cellular uptake.

The present invention includes embodiments wherein any problems associated with the tat cysteine-rich region are solved, because that region is not present in the transport polypeptides described herein. In those embodiments, cellular uptake of the transport polypeptide or transport polypeptide-cargo molecule conjugate still occurs. In one group of preferred embodiments of this invention, the sequence of amino acids preceding the cysteine-rich region is fused directly to the sequence of amino acids following the cysteine-rich region. Such transport polypeptides are called tat$\Delta$cys, and have the general formula (tat1-21)–(tat38-n), where n is the number of the carboxy-terminal residue, i.e., 49–86. Preferably, n is 58–72. As will be appreciated from the examples below, the amino acid sequence preceding the cysteine-rich region of the tat protein is not required for cellular uptake. A preferred transport polypeptide (or transport moiety) consists of amino acids 37–72 of tat protein, and is called tat37-72 (SEQ ID NO:2). Retention of tat residue 37, a cysteine, at the amino terminus of the transport polypeptide is preferred, because it is useful for chemical cross-linking.

The advantages of the tat$\Delta$cys polypeptides, tat37-72 and other embodiments of this invention include the following:

a) The natural activity of tat protein, i.e., induction of HIV transcription, is eliminated;

b) Dimers, and higher multimers of the transport polypeptide are avoided;

c) The level of expression of tat$\Delta$cys genetic fusions in *E.coli* may be improved;

d) Some transport polypeptide conjugates display increased solubility and superior ease of handling; and e) Some fusion proteins display increased activity by the cargo moiety, as compared with fusions containing the cysteine-rich region.

The pharmaceutical compositions of this invention may be for therapeutic, prophylactic or diagnostic applications, and may be in a variety of forms. These include, for example, solid, semi-solid, and liquid dosage forms, such as tablets, pills, powders, liquid solutions or suspensions, aerosols, liposomes, suppositories, injectable and infusible solutions and sustained release forms. The preferred form depends on the intended mode of administration and the therapeutic, prophylactic or diagnostic application. According to this invention, a selected molecule of interest-tat protein conjugate or a transport polypeptide-cargo molecule conjugate may be administered by conventional routes of administration, such as parenteral, subcutaneous, intravenous, intramuscular, intralesional, intrasternal, intracranial or aerosol routes. Topical routes of administration may also be used, with application of the compositions locally to a particular part of the body (e.g., skin, lower intestinal tract, vagina, rectum) where appropriate. In the case of a papillomavirus infection, for example, topical administration would be indicated. The compositions also preferably include conventional pharmaceutically acceptable carriers and adjuvants that are known to those of skill in the art.

A selected molecule of interest in combination with tat protein or a molecule of interest-tat protein conjugate can also be used in making a vaccine. For example, the molecule of interest can be an antigen from the bacteria or virus or other infectious agent that the vaccine is to immunize against (e.g., gp120 of HIV). Providing the antigen into the cell cytoplasm allows the cell to process the molecule and express it on the cell surface. Expression of the antigen on the cell surface will raise a killer T-lymphocyte response, thereby inducing immunity.

Generally, the pharmaceutical compositions of the present invention may be formulated and administered using methods and compositions similar to those used for pharmaceutically important polypeptides such as, for example, alpha interferon. It will be understood that conventional doses will vary depending upon the particular cargo involved, as well as the patient's health, weight, age, sex, the condition or disease and the desired mode of administration. The pharmaceutical compositions of this invention include pharmacologically appropriate carriers, adjuvants and vehicles. In general, these carriers include aqueous or alcoholic/aqueous solutions, emulsions or suspensions, including saline and buffered media. Parenteral vehicles can include sodium chloride solution, Ringer's dextrose, dextrose and sodium chloride, lactated Ringer's or fixed oils. In addition, intravenous vehicles can include fluid and nutrient replenishers, and electrolyte replenishers, such as those based on Ringer's dextrose. Preservatives and other additives can also be present, such as, for example, antimicrobials, antioxidants, chelating agents, and inert gases. See, generally, *Remington's Pharmaceutical Sciences*, 16th Ed., Mack, ed. 1980.

The processes and compositions of this invention may be applied to any organism, including humans. The processes and compositions of this invention may also be applied to animals and humans in utero.

For many pharmaceutical applications of this invention, it is necessary for the cargo molecule to be translocated from body fluids into cells of tissues in the body, rather than from a growth medium into cultured cells. Therefore, in addition to examples below involving cultured cells, we have provided examples demonstrating delivery of model cargo proteins into cells of various mammalian organs and tissues, following intravenous injection of transport polypeptide-cargo protein conjugates into live animals. These cargo proteins display biological activity following delivery into the cells in vivo.

As demonstrated in the examples that follow, using the amino acid and DNA sequence information provided herein, the transport polypeptides of this invention may be chemically synthesized or produced by recombinant DNA methods. Methods for chemical synthesis or recombinant DNA production of polypeptides having a known amino acid sequence are well known. Automated equipment for polypeptide or DNA synthesis is commercially available. Host cells, cloning vectors, DNA expression control sequences and oligonucleotide linkers are also commercially available.

Using well-known techniques, one of skill in the art can readily make minor additions, deletions or substitutions in the preferred transport polypeptide amino acid sequences set forth herein. It should be understood, however, that such variations are within the scope of this invention.

Furthermore, tat proteins from other viruses, such as HIV-2 (M. Guyader et al., "Genome Organization and Transactivation of the Human Immunodeficiency Virus Type 2", *Nature*, 326, pp. 662–669 (1987)), equine infectious anemia virus (R. Carroll et al., "Identification of Lentivirus Tat Functional Domains Through Generation of Equine Infectious Anemia Virus/Human Immunodeficiency Virus Type 1 tat Gene Chimeras", *J. Virol.*, 65, pp. 3460–67 (1991)), and simian immunodeficiency virus (L. Chakrabarti et al., "Sequence of Simian Immunodeficiency Virus from Macaque and Its Relationship to Other Human and Simian Retroviruses", *Nature*, 328, pp. 543–47 (1987); S. K. Arya et al., "New Human and Simian HIV-Related Retroviruses Possess Functional Transactivator (tat) Gene", *Nature*, 328, pp. 548–550 (1987)) are known. It should be understood that polypeptides derived from those tat proteins fall within the scope of the present invention, including those characterized by the presence of the tat basic region and the absence of the tat cysteine-rich region.

The Molecule of Interest-Tat Protein Conjugate

A molecule of interest, which will generally be a protein or peptide, a nucleotide sequence, or other chemical which has diagnostic, prophylactic or therapeutic application (referred to herein as a drug) is combined, as described below, with HIV tat protein to produce a molecule of interest-tat protein conjugate. The resulting conjugate is brought into contact with the extracellular surface of cells.

In one embodiment of the present invention, the molecule of interest is a protein, such as an enzyme, antibody, toxin, or regulatory factor (e.g., transcription factor) whose delivery into cells, and particularly into the cell nucleus is desired. For example, some viral oncogenes inappropriately turn on expression of cellular genes by binding to their promoters. By providing a competing binding protein in the cell nucleus, viral oncogene-activity can be inhibited.

In a further embodiment, the molecule of interest is a nucleotide sequence to be used as a diagnostic tool (or probe), or as a therapeutic agent, such as an oligonucleotide sequence which is complementary to a target cellular gene or gene region and capable of inhibiting activity of the cellular gene or gene region by hybridizing with it. In yet another embodiment, the molecule of interest is a drug, such as a peptide analog or small molecule enzyme inhibitor, whose introduction specifically and reliably into the cell nucleus is desired.

The molecule of interest can be obtained or produced using known techniques, such as chemical synthesis, genetic engineering methods and isolation from sources in which it occurs naturally. The molecule of interest can be combined with or attached to the tat protein to form the molecule of interest-tat protein conjugate which is a subject of the present invention.

The attachment of the molecule of interest to tat to produce a molecule of interest-tat protein conjugate may be effected by any means which produces a link between the two constituents which is sufficiently stable to withstand the conditions used and which does not alter the function of either constituent. Preferably, the link between them is covalent. For example, recombinant techniques can be used to covalently attach tat protein to molecules, such as by joining the gene coding for the molecule of interest with the gene coding for tat and introducing the resulting gene construct into a cell capable of expressing the conjugate. Alternatively, the two separate nucleotide sequences can be expressed in a cell or can be synthesized chemically and subsequently joined, using known techniques. Alternatively, the protein of interest-tat molecule can be synthesized chemically as a single amino acid sequence (i.e., one in which both constituents are present) and, thus, joining is not needed.

Numerous chemical cross-linking methods are known and potentially applicable for conjugating the transport polypeptides of this invention to cargo macromolecules. Many known chemical cross-linking methods are non-specific, i.e., they do not direct the point of coupling to any particular site on the transport polypeptide or cargo macromolecule. As a result, use of non-specific cross-linking agents may attack functional sites or sterically block active sites, rendering the conjugated proteins biologically inactive.

A preferred approach to increasing coupling specificity in the practice of this invention is direct chemical coupling to a functional group found only once or a few times in one or both of the polypeptides to be cross-linked. For example, in many proteins, cysteine, which is the only protein amino acid containing a thiol group, occurs only a few times. Also, for example, if a polypeptide contains no lysine residues, a cross-linking reagent specific for primary amines will be selective for the amino terminus of that polypeptide. Successful utilization of this approach to increase coupling specificity requires that the polypeptide have the suitably rare and reactive residues in areas of the molecule that may be altered without loss of the molecule's biological activity.

As demonstrated in the examples below, cysteine residues may be replaced when they occur in parts of a polypeptide sequence where their participation in a cross-linking reaction would likely interfere with biological activity. When a cysteine residue is replaced, it is typically desirable to minimize resulting changes in polypeptide folding. Changes in polypeptide folding are minimized when the replacement is chemically and sterically similar to cysteine. For these reasons, serine is preferred as a replacement for cysteine. As demonstrated in the examples below, a cysteine residue may be introduced into a polypeptide's amino acid sequence for cross-linking purposes. When a cysteine residue is introduced, introduction at or near the amino or carboxy terminus is preferred. Conventional methods are available for such amino acid sequence modifications, whether the polypeptide of interest is produced by chemical synthesis or expression of recombinant DNA.

Coupling of the two constituents can be accomplished via a coupling or conjugating agent. There are several intermolecular cross-linking reagents which can be utilized (see, for example, Means, G. E. and Feeney, R. E., *Chemical Modification of Proteins*, Holden-Day, 1974, pp. 39–43). Among these reagents are, for example, J-succinimidyl 3-(2-pyridyldithio) propionate (SPDP) or N,N'-(1,3-phenylene) bismaleimide (both of which are highly specific for sulhydryl groups and form irreversible linkages); N,N'-ethylene-bis-(iodoacetamide) or other such reagent having 6 to 11 carbon methylene bridges (which relatively specific for sulfhydryl groups); and 1,5-difluoro-2,4-dinitrobenzene (which forms irreversible linkages with amino and tyrosine groups). Other cross-linking reagents useful for this purpose include: p,p'-difluoro-m, m'-dinitrodiphenylsulfone (which forms irreversible cross-linkages with amino and phenolic groups); dimethyl adipimidate (which is specific for amino groups); phenol-1,4-disulfonylchloride (which reacts principally with amino groups); hexamethylenediisocyanate or diisothiocyanate, or azophenyl-p-diisocyanate (which reacts principally with amino groups); glutaraldehyde (which reacts with several different side chains) and disdiazobenzidine (which reacts primarily with tyrosine and histidine).

Cross-linking reagents may be homobifunctional, i.e., having two functional groups that undergo the same reaction. A preferred homobifunctional cross-linking reagent is bismaleimidohexane ("BMH"). BMH contains two maleimide functional groups, which react specifically with sulfhydryl-containing compounds under mild conditions (pH 6.5–7.7). The two maleimide groups are connected by a hydrocarbon chain. Therefore, BMH is useful for irreversible cross-linking of polypeptides that contain cysteine residues.

Cross-linking reagents may also be heterobifunctional. Heterobifunctional cross-linking agents have two different functional groups, for example an amine-reactive group and a thiol-reactive group, that will cross-link two proteins having free amines and thiols, respectively. Examples of heterobifunctional cross-linking agents are succinimidyl 4-(N-maleimidomethyl)cyclohexane-1-carboxylate ("SMCC"), m-maleimidobenzoyl-N-hydroxysuccinimide ester ("MBS"), and succinimide 4-(p-maleimidophenyl) butyrate ("SMPB"), an extended chain analog of MBS. The succinimidyl group of these cross-linkers reacts with a primary amine, and the thiol-reactive maleimide forms a covalent bond with the thiol of a cysteine residue.

Cross-linking reagents often have low solubility in water. A hydrophilic moiety, such as a sulfonate group, may be added to the cross-linking reagent to improve its water solubility. Sulfo-MBS and sulfo-SMCC are examples of cross-linking reagents modified for water solubility.

Many cross-linking reagents yield a conjugate that is essentially non-cleavable under cellular conditions. However, some cross-linking reagents contain a covalent bond, such as a disulfide, that is cleavable under cellular conditions. For example, dithiobis(succinimidylpropionate) ("DSP"), Traut's reagent and N-succinimidyl 3-(2-pyridyldithio) propionate ("SPDP") are well-known cleavable cross-linkers. The use of a cleavable cross-linking reagent permits the cargo moiety to separate from the transport polypeptide after delivery into the target cell. Direct disulfide linkage may also be useful.

Some new cross-linking reagents such as n-γ-maleimidobutyryloxy-succinimide ester ("GMBS") and sulfo-GMBS, have reduced immunogenicity. In some embodiments of the present invention, such reduced immunogenicity may be advantageous.

Numerous cross-linking reagents, including the ones discussed above, are commercially available. Detailed instructions for their use are readily available from the commercial suppliers. A general reference on protein cross-linking and conjugate preparation is: S. S. Wong, *Chemistry of Protein Conjugation and Cross-Linking*, CRC Press (1991).

Chemical cross-linking may include the use of spacer arms. Spacer arms provide intramolecular flexibility or adjust intramolecular distances between conjugated moieties and thereby may help preserve biological activity. A spacer arm may be in the form of a polypeptide moiety comprising spacer amino acids. Alternatively, a spacer arm may be part of the cross-linking reagent, such as in "long-chain SPDP" (Pierce Chem. Co., Rockford, Ill., cat. No. 21651 H).

Delivery of a Molecule of Interest Using the Present Method

The present method can be used to deliver a molecule of interest into cells, particularly into the cell nucleus, in vitro or in vivo. In in vitro applications in which the molecule is to be delivered into cells in culture, the molecule of interest in combination with tat protein or the molecule of interest-tat protein conjugate is simply added to the culture medium. This is useful, for example, as a means of delivering into the nucleus substances whose effect on cell function is to be assessed. For example, the activity of purified transcription factors can be measured, or the in vitro assay can be used to provide an important test of a molecule's activity, prior to its use in in vivo treatment.

Alternatively, the molecule of interest in combination with tat protein or the molecule of interest-tat protein conjugate can be used for prophylactic or therapeutic purposes (for the treatment, prophylaxis or diagnosis of a disease or condition). For example, a selected molecule of interest in combination with tat protein or the molecule of interest-tat protein conjugate can be combined with a sample obtained from an individual (e.g., blood, bone marrow) in order to introduce the molecule of interest into cells present in the sample and, after treatment in this manner, the sample returned to the individual. A series of treatments carried out in this manner can be used to prevent or inhibit the effects of an infectious agent. For example, blood can be removed from an individual infected with HIV or other viruses, or from an individual with a genetic defect. The blood can then be combined with a molecule of interest in combination with tat protein or a molecule of interest-tat protein conjugate in which the molecule of interest is a drug capable of inactivating the virus or an oligonucleotide sequence capable of hybridizing to a selected virus sequence and inactivating it or a protein that supplements a missing or defective protein, under conditions appropriate for entry in cells of the conjugate and maintenance of the sample in such a condition that it can be returned to the individual. After treatment, the blood is returned to the individual.

Alternatively, the molecule of interest in combination with tat protein or a molecule of interest-tat protein conjugate can be delivered in vivo. For example, cells that synthesize tat or tat conjugate can be produced and implanted into an individual so that tat or tat conjugate is constantly present. In another embodiment, the conjugate can be used much like a conventional therapeutic agent and can be a component of a pharmaceutical composition which includes other components useful, for example, for delivery, stability or activity of the conjugate. In this embodiment, a selected molecule of interest in combination with tat protein or a molecule of interest-tat protein conjugate, such as a selected oligonucleotide sequence-tat protein conjugate, can be administered in sufficient quantity to result in entry into cells, particularly cell nuclei, and inhibition (reduction or elimination) of the causative agent (e.g., virus or bacterium) or provision of a missing or defective protein.

Demonstration of Uptake of Tat into the Cell Nucleus

An unexpected result was seen when tat was simply added to the culture medium of HL3T1 cells (HeLa cells containing the integrated LTR-CAT plasmid). Expression of CAT from the integrated HIV-1 promoter increased and was proportional to the tat concentration, indicating that tat was taken up and transactivated the HIV-1 promoter. This result was surprising because proteins and peptides are generally believed to be poorly taken up by cells. Sternson, L. A., *Ann. N.Y. Acad. Sci.*, 5719–21 (1987).

To measure cellular uptake directly, HL3T1 cells were treated with $^{125}$I-labeled tat in the presence or absence of chloroquine, and the amount of radioactive tat present in various cellular fractions was determined. This work is described in greater detail in Example III.

We assessed the expression of CAT by HL3T1 cells incubated with tat protein for 24 hours, at concentrations ranging from 2 ug to 50 ug tat protein. Expression of CAT from the integrated HIV-1 promoter increased and was proportional to the tat concentration. CAT activity did not increase further after 24 hours. Additional small increases in activity (2- to 3-fold) were observed upon addition of 10 mM zinc or 1 mM cadmium, suggesting that metals might stabilize tat either during uptake or once inside the cell.

To explore the uptake process further, various lysosomotrophic agents were added to the culture medium. Lysosomotrophic agents are thought to inhibit receptor-mediated endocytosis. Mellman, I. et al., *Ann. Rev. Biochem.* 55:663–700 (1986).

We also studied the effect that a variety of lysosomotrophic agents had on uptake and subsequent transactivation by tat placed in tissue culture medium. HL3T1 cells were incubated with 5 μg of tat (100 nM) and each agent for 24 hours, the medium was replaced, and CAT activity was determined after 60 hours. We measured activity from untreated cells, cells incubated with tat alone and cells incubated with chloroquine alone. The level of uptake and subsequent transactivation in HL3T1 cells by 5 μg of tat with chloroquine present was about 7000-fold compared with untreated cells, whereas chloroquine gave little increase in promoter activity in the absence of tat. Monensin, amantadine and methylamine also significantly increased transactivation, whereas ammonium chloride only slightly increased activity. No lysosomotrophic agent tested significantly activated the promoter in the absence of tat. The parameters of chloroquine-stimulated tat activity are explained in more detail in Example IV.

FIG. 2 shows that within 6 hours after treating HL3T1 cells with tat and chloroquine, a significant amount of radioactive tat (about 3% of the total) had been taken up by the cells. Most of this tat (<80%) was localized in the nuclear fraction. Trypsin-sensitive counts, representing tat protein bound to the cell surface, remained relatively constant and by 12 hours were less than 20% of the counts found in the nucleus.

In another experiment, we ran nuclear extracts from HL3T1 cells treated with tat on an SDS gel. Gels were analysed in the presence or absence of chloroquine. A radioactive band comigrating with intact tat was readily apparent. HL3T1 cells treated with tat but without chloroquine showed similar kinetics of uptake and nuclear localization when assayed by counting the cellular fractions but only degraded tat was seen on the gel.

The ability of tat to directly enter lymphocytes or monocytes was also assessed; tat readily entered both types of cells, as demonstrated by the high levels of transactivation in cells treated with tat, alone or with chloroquine. H9 lymphocytes and U937 promonocytes ($10^6$ cells) containing an integrated HIV-I LTR-CAT plasmid (H938 and U38 cells, respectively (Felber, B. K. and G. N. Pavlakis, *Science* 239:184 (1988)) were incubated in RPMI 1640 medium containing 10% fetal bovine serum (1 ml in 25 mm wells) at 37° C. (no tat), treated with 5 μg of tat protein (tat) or treated with 5 μg of tat and 100 μm chloroquine (tat+CQ). Cells were harvested 24 hours after tat treatment and assayed for CAT activity (Gorman, C. M. et al., *Mol. Cell Biol.* 2:1044 (1982). HeLa cells ($10^6$ cells) containing an integrated HIV-1 LTR-CAT plasmid (HL3T1) (Felber, B. K. and G. N. Pavlakis, *Science* 239:184 (1988)), were incubated in Dulbecco's modified Eagle's medium (DMEM) with 10% fetal bovine serum (1 ml in 25 mm wells) and similarly treated with tat protein, or with tat and chloroquine, and assayed for CAT activity. Unacetylated (cm) and acetylated (ac) forms of $^{14}$C chloramphenicol were separated by thin layer chromatography.

High levels of transactivation were seen in all cell lines. In the HeLa cells, the addition of chloroquine resulted in a significant stimulation of tat activity. However, in contrast to the case with HeLa cells, chloroquine had little effect on tat entry into lymphocytes or monocytes. The chloroquine-independent entry into lymphocytes and monocytes may suggest a different mechanism of uptake.

The time course of binding was determined in HeLa (HL3T1) cells containing an integrated HIV-I LTR-CAT plasmid (Felber, B. K. and G. N. Pavlakis, *Science* 239:184 (1988)). Cells ($2\times10^6$) were grown to confluence in 12 well tissue culture plates (12 turn well diameter), and washed with phosphate buffered saline (PBS). Cells were incubated in fresh DMEM with 1 μg tat (1-72) and 100 μM chloroquine at 37° C. for different lengths of time. Following two washes with PBS to remove tat, fresh medium was added and transactivation was measured 24 hours after tat addition. CAT activity was used as a measure of transactivation.

Figure 4:
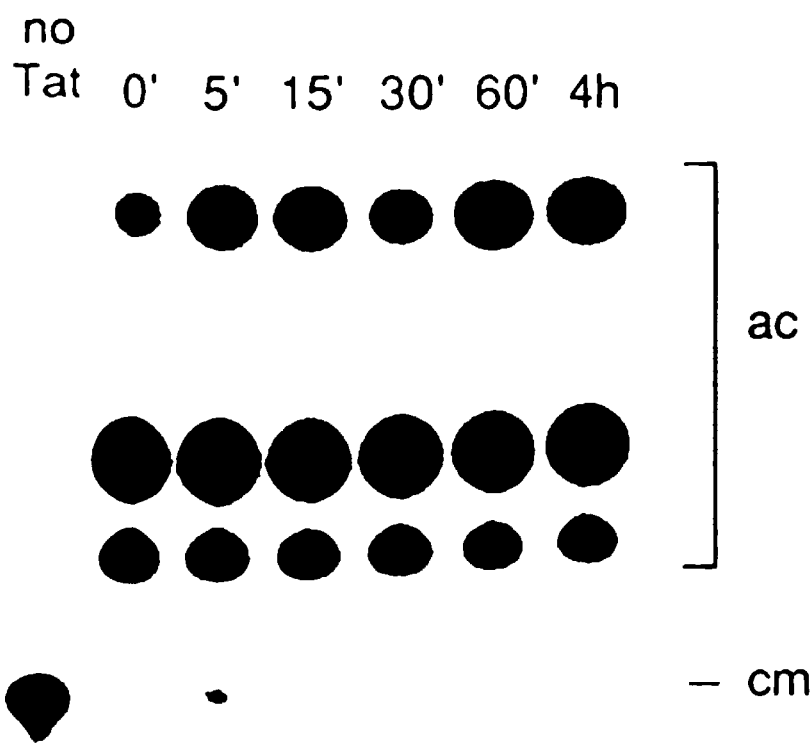
FIG. 4 is a representation of a thin layer chromatogram used to analyze chloramphenicol acetyl transferase activity from HL3T1 cells in experiments illustrating the extent of activation of the CAT reporter gene following various time periods of exposure to 1 μg tat protein+100 μM chloroquine.

The results of this analysis are shown in FIG. 4. The basal level of expression from the HIV-1 LTR in the absence of tat is shown in the "no Tat" lane. Maximal levels of transactivation were observed after a five minute exposure to tat.

Thus, binding is rapid, and a brief exposure can result in uptake by cells, as assayed by transactivation.

Figure 5:
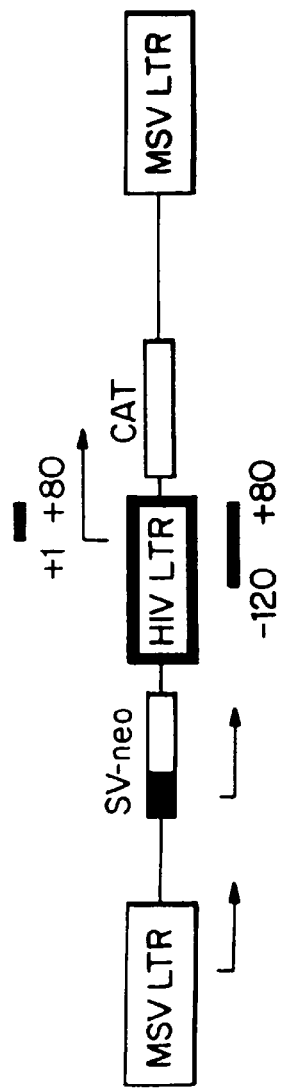
FIG. 5 schematically depicts the murine sarcoma virus (MSV) retroviral vector used to establish the H938 reporter cell line from H9 cells. The transcription start sites from the SV40 promoter, the HIV and MSV LTRs are indicated by arrows, and the location and size of the fragments protected in the RNase analysis are indicated by bars.

The time required to observe a response to exogenous tat was determined in H938 cells. H938 cells were derived from the H9 lymphoid cell line by infection with a murine sarcoma virus (MSV) retroviral vector. (Felber, B. K. and G. N. Pavlakis, *Science* 239:184 (1988)). The integrated MSV vector contains the CAT gene under the control of the HIV-1 LTR, and the neo gene under the control of an SV40 promoter (FIG. 5). H938 cells were maintained in RPMI 1640 medium supplemented with 10% fetal bovine serum, penicillin (250 U/ml), and streptomycin (250 µg/ml). The cells were treated with 10 µg/ml of tat protein (amino acids 1–72) in the presence of 100 µg/ml protamine, and RNA was prepared and analyzed by RNase protection. An $\alpha$-$^{32}$P UTP-labeled HIV-1 LTR probe corresponding to a 200 bp fragment from −120 to +80 of the viral LTR was prepared by in vitro transcription. These procedures are further described in Example V.

The results of the RNase protection assay revealed that two major fragments were protected. The 80 nucleotide fragment is derived from transcripts expressed from the HIV LTR and the 200 nucleotide fragment is derived from transcripts expressed from either the upstream MSV or SV40 promoters. Transcription from the HIV LTR increased after 15 minutes of exposure to tat, and reached a maximum by 2–6 hours. In contrast, transcription from the upstream MSV and SV40 promoters was not increased by tat addition, indicating that exogenously added tat retains specificity for the HIV promoter. When tat protein is added exogenously to cells, there is a significant increase in transcription in 15 minutes, indicating that tat can enter cells, become localized to the nucleus, bind to its target site TAR specifically, and promote transcription within 15 minutes. (The short transcripts, which may be degradation products from incompletely elongated RNAs, were not affected by tat.)

Figure 6:
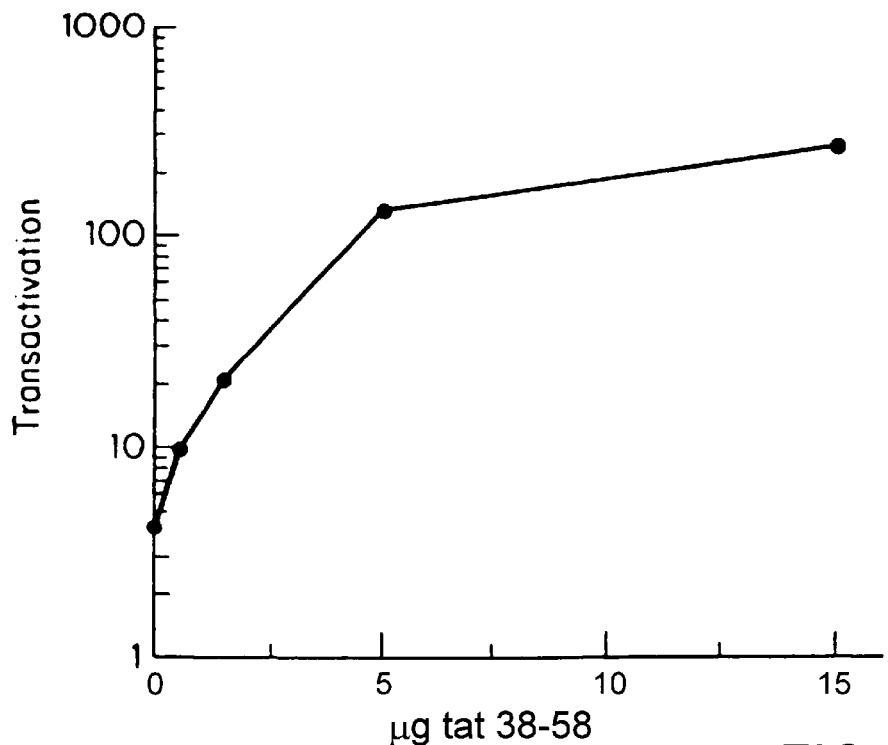
FIG. 6 summarizes data on the enhancement of transactivation in H938 cells upon addition of increasing amounts of the tat 38–58 peptide with 1 μg of tat protein as assayed by CAT activity after a 24 hour incubation with peptide and tat protein.

Several peptide fragments of tat were tested for their ability to compete for tat binding and uptake in HL3T1 and H938 cells. In these experiments, 0.5×10$^6$ H938 cells were pelleted and resuspended in 0.5 ml fresh RPMI 1640 medium. Cells were incubated at 37° C. with 1 µg tat (1-72) and increasing concentrations of peptide. Extracts were prepared after 24 hours and assayed for CAT activity. Surprisingly, tat 38-58, which contains the basic region of tat, actually enhanced the effect of exogenous tat and increased transactivation in a concentration dependent manner. FIG. 6 shows the results of this experiment in the H938 cell line. The data was quantitated by cutting the spots from the TLC plates and counting the associated radioactivity in a scintillation counter.

Protamine (protamine sulfate, Sigma), another basic peptide, was also observed to enhance transactivation by extracellular tat when present at a concentration of 100 µg/ml. However, a smaller tat peptide, containing only the basic region from 47-58, had no effect on transactivation under the conditions used. A mixture of two peptides, tat 38-47 and tat 48-58, the products of chymotryptic digestion of tat 38-58, also had no effect on transactivation under these conditions. No enhancement of activity by protamine was seen when HL3T1 cells were scrape-loaded with tat, suggesting that protamine directly affects the uptake process.

Other cell lines were also tested for tat uptake and transactivation activity. Jurkat T cells showed significant transactivation when tat was added to the medium and showed further transactivation in the presence of chloroquine. A Vero line (VNHIV-CAT; Mosca, J. D. et al., *Nature* 325:67–70 (1987)) also showed significant transactivation upon incubation of cells with tat and chloroquine; no activity was seen with tat alone. However, since the basal expression of CAT was low in this cell line, a several fold increase in CAT activity would still have been undetectable.

To directly follow the entry of tat into live cells, tat was labelled with rhodamine (TRITC-tat) and its movement was followed by fluorescence microscopy. Punctate staining was observed on the surface of HL3T1 and H938 cells immediately after incubation with TRITC-tat, similar to that seen in receptor-mediated endocytosis. After one hour, clear nuclear staining was observed in HL3T1 cells. Punctate cytoplasmic staining was also observed, suggesting that tat may be localized within endosomes. Incubation at low temperature, which blocks endocytosis, also blocked entry of rhodamine-labeled tat. After six hours, most of the tat was in the nucleus of HL3T1 cells, but was excluded from the nucleoli. Remarkably, every cell in the culture was labeled with TRITC-tat, indicating that the uptake of exogenous tat is efficient. (Cellular localization was also examined in H938 cells, however, since the nucleus constitutes most of the lymphocytic cell, it was difficult to distinguish nuclear from non-nuclear compartments). When tested for transactivation, TRITC-tat was found to have the same specific activity as unmodified tat.

Tat-mediated Uptake of a Heterologous Protein

A preliminary assessment of the ability of tat to mediate the uptake of a molecule of interest was carried out. Additional details of this analysis are provided in Example VII. The E2 open reading frame of the bovine papillomavirus-1 (BPV-1; Chen, E. Y. et al., *Nature* 299:529–534 (1982)) encodes both positive and negative acting transcriptional regulators (regulatory factors; Sousa, R. et al., *Biochim. Biophys. Acta* 1032:19–37 (1990); Lambert, P. F et al., *J. Virol.* 63(7):3151–3154 (1989); Lambert, P. F. et al., *Cell* 50:69–78 (1987)). A fusion gene was constructed in which the HIV-1 tat gene was linked to the carboxy-terminal region of the E2 open reading frame. The construct which encodes the fusion protein, pFTE103 (constructed by Dr. J. Barsoum, Biogen, Inc.), was designed to express a protein comprising amino acids 1 through 67 of tat at the amino terminus, followed by the C-terminal 105 amino acids of E2 (residues 306 through 410 of BPV-1 E2), which contain the DNA binding domain of the E2 open reading frame (EP 0,302, 758, Androphy et al., (Feb. 6, 1989); Giri, I. and Yaniv, M., *EMBO J.* 7(9):2823–2829 (1988); McBride, A. A. et al., *EMBO J.* 7(2):533–539 (1988); Androphy, E. J. et al., *Nature* 325:70–73 (1987)). pFTE103 was introduced into *E. coli* and the TatE2C fusion protein was expressed using the T7 RNA polymerase expression system as described by Studier et al. (Studier et al., *Methods in Enzymology* 185:60–89 (1990)). The purified tatE2C fusion protein migrated with an apparent molecular weight of 20,000 to 21,000 daltons on protein gels. Uptake of the TatE2C fusion protein was tested following introduction into the culture medium of animal cells.

Uptake of the tat portion of the fusion protein (molecule of interest-tat protein conjugate) was assayed by measuring transactivation of a tat-responsive reporter construct integrated into HeLa cells (HeLa.318 cells). The tat-responsive reporter construct (pXB318) present in HeLa.318 cells contains the human tissue plasminogen activator (tPA) cDNA reporter gene from pTPA114 (Fisher et al. *J. Biol. Chem.* 260:11223–11230 (1985)) under the control of the HIV-1 long terminal repeat (LTR) from pU3R-III (Sodroski et al. *Science* 227:171–173 (1985)). Tat protein (amino acids 1–72) or the TatE2C fusion protein were added to the culture medium of HeLa.318 cells in 24 well plates at concentrations ranging from 2.5 nM to 250 nM, in the presence of 100 µM chloroquine, essentially as described (Frankel, A. D. and Pabo, C. O., Cell 55:1189–1193 (1988)). The culture medium was harvested 24 hours later and assayed for tPA activity by the method of Granelli-Piperno and Reich (J. Exp. Med. 148:223–234 (1978)). Cell numbers were determined and tPA secretion was expressed as ng/$10^6$ cells per day. FIG. 7 shows the results obtained from a tPA assay of HeLa.318 media 24 hours after the addition of tat or TatE2C protein to culture medium. In the absence of tat or the TatE2C protein, tPA activity was undetectable (less than 0.1 ng/$10^6$ cells per day). However, addition of either tat or TatE2C protein led to an increase in tPA production (FIG. 7). Thus, it appears that tat (residues 1–67) can retain the ability to enter cells when linked to a heterologous protein.

Although transactivation upon addition of the TatE2C protein was somewhat less efficient than that observed upon addition of tat, the TatE2C fusion protein was also less active than tat in transactivation assays when the proteins were produced intracellularly after transfection of the genes into HeLa.318 cells. Thus, it is not clear whether the apparent reduction in activity is attributable to reduced uptake or reduced activity of the fusion protein produced by E. coli and added exogenously. It is possible that some tat activity may be lost during the denaturation and refolding of the TatE2C fusion protein during purification.

Uptake of the E2 portion of the conjugate was determined by indirect immunofluorescence using rabbit polyclonal serum raised against E2-C85 (the C-terminal 85 amino acids of the E2 protein produced in E. coli). For indirect immunofluorescence, mouse 3T3 cells were seeded into LAB-TEK four chamber tissue culture chamber/slides. The next day, TatE2C fusion protein was added at 250 nM to the culture medium, in the presence of 100 µM chloroquine. Six hours later, immunofluorescence was performed as described in Example VII.

While only very faint background fluorescence was seen when E2. C85 protein was added to cells (at the same concentration and in the presence of 100 µM chloroquine), addition of the TatE2C fusion protein led to very intense fluorescence in all cells observed. These cells displayed fluorescence on the plasma membrane, in the cytosol and in nuclei. The staining was present in bright patches rather than evenly dispersed throughout the cells. The amount of E2 fluorescence obtained following addition of TatE2C protein to culture medium was far greater than the immunofluorescence observed when a TatE2C gene was expressed in these same cells. These data indicate that the tat protein is capable of efficiently carrying a heterologous protein present as part of a molecule of interest-tat conjugate into cells.

In order that the invention described herein may be more fully understood, the following examples are set forth. It should be understood that these examples are for illustrative purposes only and are not to be construed as limiting this invention in any manner. Throughout these examples, all molecular cloning reactions were carried out according to methods in J. Sambrook et al., *Molecular Cloning: A Laboratory Manual*, 2nd Edition, Cold Spring Harbor Laboratory (1989), except where otherwise noted.

EXAMPLE I

Bacterial Expression and Purification of Tat

Two plasmids were constructed to produce the tat protein in E. coli; one expresses amino acids 1–86 (the entire coding sequence) and the other expresses the first coding exon of tat (residues 1–72). It is known that the second exon is not required for activity (Cullen, B. R., Cell 46:973–982 (1986); Muesing, M. A., et al., Cell 48:691–701 (1987); Sodroski, J., et al., Science 229:74–77 1985); Frankel, A. D., et al., Proc. Natl. Acad. Sci., USA 86:7397–7401 (1989)). Synthetic tat genes were constructed and ligated into the NdeI site of pET-3a, a plasmid that uses a strong bacteriophage T7 promoter to express cloned genes (Studier, F. W. and B. M. Moffat, J. Mol. Biol. 189:113–130 (1986); Rosenberg, A. H., et al., Gene 56: 125–135 (1987)). The resulting plasmids, ptat72 and ptat86, express tat (residues 1–72 or 1–86, respectively) as 1%–5% of total E. coli protein. Both proteins gave similar results in all experiments. BL21(DE3) cells were used for expression and these cells also contained a plasmid expressing the T7 lysozyme gene to inhibit any T7 RNA polymerase expressed prior to induction (F.W. Studier, personal communication). Tat was induced with isopropyl β-D-thiogalactopyranoside (IPTG) (Studier, F. W. and B. M. Moffat, J. Mol. Biol. 189:113–130 (1986)) and purified essentially as described (Frankel, A. D., et al., Science 240:70–73 (1988)) except that tat was extracted from the polyethyleneimine pellet with 10% ammonium sulfate instead of 700 mM KCl, and the S-Sepharose chromatography was eliminated.

EXAMPLE II

Synthetic Tat Peptides

Syntheses were performed using Fmoc chemistry on a Milligen/Biosearch model 9600 peptide synthesizer with a peptide amide linker-norleucine 4-methylbenzhydrylamine (PAL-NIe-MBHA) polystyrene resin (Milligen/Biosearch; 0.5 g). The benzotriazolyloxytris(dimethylamino) phosphonium hexafluorophosphate/1-hydroxybenzotriazole (BOP/HOBt) coupling method (Hudson, D., J. Org. Chem. 53:617–624 (1988)) was used with coupling times of 1–4 hours and with double coupling of His-33. Protecting groups were t-butyl ester (for Glu and Asp), 2,2,5,7,8-pentamethylchroman-6-sulfonyl (Arg), t-butyloxycarbonyl (Lys), trityl (His and Cys), t-butyl (Ser, Thr, and Tyr), and trimethoxybenzyl (Asn and Gin). All peptides were synthesized as their C-terminal amides. After synthesis was completed, protecting groups were removed and the peptide chains were cleaved from the resin with trifluoroacetic acid/ethanedithiol/thioanisole/anisole (90:3:5:2, vol/vol). The mixture was filtered and the products were obtained by addition of cold anhydrous diethyl ether to the filtrate. The precipitate was collected by filtration, thoroughly washed with ether and dried.

Peptides were treated with 0.5 M dithiothreitol at 37° C. for 30 minutes to ensure complete reduction of the cysteines and were purified on a $C_4$ HPLC column (Vydac) using an acetonitrile gradient in 0.1% trifluoroacetic acid. Amino acid composition was determined by hydrolysis in 6 M HCl containing 0.5% phenol at 100° C. and analysis on a LKB Alpha Plus analyzer. Peptide purity (>90%) was determined by HPLC using an acetonitrile gradient of <0.5% per minute.

EXAMPLE III

Uptake of $^{125}$I-Labeled Tat

Tat (residues 1–72) was labeled with $^{125}$I by treating 500 µg of protein with 0.5 mCi $^{125}$I and IODO-BEADS (Pierce) in 0.1 M Tris-HCl (pH 7.5) at room temperature for 5 minutes. The sample was dialyzed to remove unreacted $^{125}$I. The specific activity was approximately $10^6$ cpm/µg protein.

HL3T1 cells (2×10⁶ cells per dish) were treated with 5 μg radioactive tat in the presence or absence of 100 μM chloroquine. Medium was removed at various times, cells were washed with PBS and EDTA, and cells were trypsinized for 10 minutes. Pancreatic trypsin inhibitor was added (5 μg/ml), cells were chilled to 4° C., centrifuged at 100×g, and the supernatant was saved. The cell pellet was washed twice with serum-free DMEM, once with PBS and nuclei were isolated by lysis in 0.5% NP-40 as described (Ausubel, F. M. et al., *Current Protocols in Molecular Biology* (New York: John Wiley and Sons, 1987)). $^{125}$I was counted using an LKB gamma counter.

EXAMPLE IV

Chloroquine Stimulated Tat Uptake

Figure 3A:
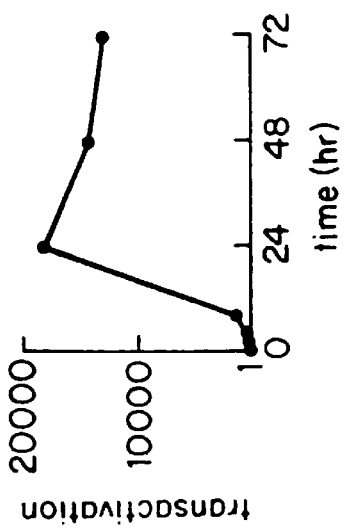
FIG. 3A graphically depicts the effect of chloroquine concentration on uptake and transactivation by 2 μg tat protein added to the medium.

The parameters of chloroquine-stimulated tat activity were studied in more detail. FIG. 3A shows that the concentration dependence of chloroquine is a rather sharp dose response with maximum transactivation observed at 100 μM chloroquine. This concentration is typically used to raise vacuolar pH (Mellman, I. et al., *Annu. Rev. Biochem.* 55:663–700 (1986)).

Figure 3B:
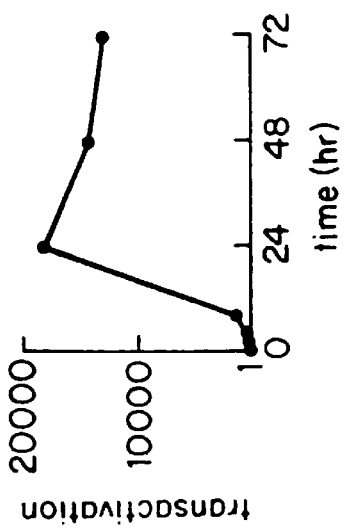
FIG. 3B graphically depicts the time course of uptake and transactivation by 2 μg of tat protein and 100 μM chloroquine.
Figure 3C:
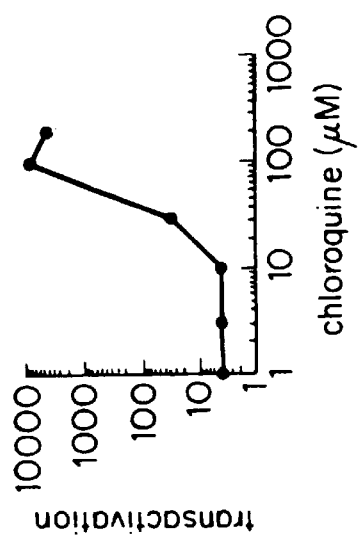
FIG. 3C graphically depicts the effect on uptake and transactivation by several concentrations of tat protein with 100 μM chloroquine.

The time course of tat transactivation in the presence of chloroquine showed a plateau after 24 hours (FIG. 3B), and transactivation in the presence of chloroquine increased with increasing tat concentration (FIG. 3C). Transactivation was detectable with tat concentrations as low as 1 nM.

Controls were done to determine whether transactivation was dependent on an intact TAR site, to determine whether a heterologous promoter could be stimulated by tat, and to determine whether any of the effects seen with chloroquine occurred when tat was produced intracellularly. After transient transfection of HeLa cells with an HIV-LTR plasmid (p-167/+80; Rosen, C. A. et al., *Cell* 41:813–823 (1985)), high levels of transactivation were seen when tat was introduced by cotransfection with a tat expression plasmid (pSV2tat72), by scrape-loading purified tat, or by treatment with tat and chloroquine. However, expression from the HIV-LTR containing a mutant TAR site (p-167/+21; Rosen, C. A. et al., *Cell* 41:813–823 (1985)) or from the SV40 early promoter (pSV2-CAT; Gorman, C. M. et al., *Mol. Cell. Biol.* 2:1044–1051 (1982)) was not stimulated when tat was introduced by these methods. Thus, introducing tat by scrape-loading or by uptake with chloroquine appears to transactivate the HIV-LTR by the same mechanism that occurs when tat is produced intracellularly. Chloroquine had no effect when tat was produced intracellularly; chloroquine treatment of HL3T1 cells transiently transfected with pSV2tat72 showed no additional transactivation.

EXAMPLE V

RNA Isolation and Analysis

For the RNase protection experiment, total RNA was isolated by the hot acidic phenol method (Queen, C. and D. Baltimore, *Cell* 33:741–748 (1983)). HIV-1-specific probes for all hybridizations were prepared by in vitro transcription (with α-$^{32}$P UTP) of an EcoRV-linearized plasmid containing the EcoRV (-120) to HindIII (+80) fragment of the viral LTR (cloned into the plasmid sp73; Promega). RNA probes were purified on Sephadex G-50 spin columns (Boehringer-Mannheim).

RNase protection experiments were performed as described (Ausubel, F. M. et al., *Current Protocols in Molecular Biology* (New York: John Wiley and Sons, 1987)). Twenty μg of cellular RNA were hybridized overnight with 5×10⁵ cpm of the RNA probe at 38° C. in 40 μl of 80% formamide, 40 mM PIPES (pH 6.7), 200 mM NaCl, 1 mM EDTA. Single-stranded RNA was digested with RNase A (10 μg/ml) and RNase Ti (45 U/ml) (Boehringer-Mannheim) in 400 μl of 10 mM Tris-HCl (pH 7.5), 300 mM NaCl, 5 mM EDTA for 1 hour at room temperature. Protected fragments were analyzed by electrophoresis on 6% polyacrylamide-7M urea sequencing gels. Protected RNAs were visualized by autoradiography with intensifying screens and were quantitated using a Betascope 603 (Betagen).

EXAMPLE VI

Localization of Tat by Fluorescence

Purified Tat protein was labeled at lysine residues with tetramethyl rhodamine isothiocyanate (TRITC) by incubating 200 μg of tat (amino acids 1–72) in 0.1 M Na$_2$CO$_3$ pH 9.0 with 5 μg of TRITC dissolved in 5 μl dimethylsulfoxide (DMSO), for 8 hours at 4° C. Unreacted TRITC was quenched with 50 mM NH$_4$Cl. The pH was lowered to 7.0 with HCl and rhodamine-labeled Tat was purified from free TRITC by dialysis against 50 mM Tris, pH 7, 1 mM DTT.

HL3T1 cells were grown on glass coverslips and incubated for various lengths of time with rhodamine-conjugated tat (TRITC-Tat) in DMEM. H938 cells in suspension were incubated with rhodamine-conjugated tat in RPMI. Cells were washed three times with phosphate buffered saline and viewed live on a Zeiss Axiophot fluorescence microscope.

EXAMPLE VII

Uptake of TatE2C Fusion Protein

Cell Lines

The mouse embryo fibroblast cell line Balb/c 3T3 (clone A31; Aaronson and Todaro, *J. Cell Physiol.* 72:141–148 (1968)) was obtained from the American Type Culture Collection. HeLa cells were obtained from Dr. Alan Frankel (Whitehead Institute, MIT). Both cell lines were propagated in Dulbecco's minimal essential medium (GIBCO) supplemented with 10% donor calf serum (Hazelton) and 4 mM glutamine (Whittaker). Cells were grown in a 5.5% CO$_2$ incubator at 37° C. Passaging of cells was performed by washing with phosphate-buffered saline and treating with trypsin (both GIBCO) to remove cells from plates followed by addition of culture medium and dilution of cells into plates containing fresh culture medium.

The HeLa cell line containing a tat-responsive reporter construct (HeLa.318) was generated by the introduction and stable selection of plasmid pXB318 (described below) by electroporation as described by Chu et al. (Chu et al., *Nucleic Acids Res.* 15:1311–1326 (1987)). pXB318 DNA was electroporated together with the selectable marker pSV2-neo (Southern, E. M. and Berg, P., *J. Mol. Appl. Genet.* 1:327–341 (1982)). Stable transfectants were selected in the presence of G418 (Southern, E. M. and Berg, P., *J. Mol. Appl. Genet.* 1:327–341 (1982)), and the presence of pXB318 DNA was confirmed by Southern blot hybridization analysis (Southern, E. M., *J. Mol. Biol.* 98:503–517 (1975)).

Vector Constructions

All molecular cloning reactions were carried out by methods described by Maniatis et al. (Maniatis, T., Fritsch, E. F., and Sambrook, J., *Molecular Cloning: A Laboratory Manual* (Cold Spring Harbor Laboratory, NY (1982)), using enzymes obtained from New England Biolabs (Beverly, Mass.).

The TatE2C fusion protein (protein TatE2C), in which HIV tat was fused to the carboxy terminal portion of BPV-1 E2, was expressed from the bacterial expression plasmid pFTE103. This plasmid was derived from ptat72 (see Example I) by insertion of a StyI-SpeI fragment which was isolated from vector pCO-E2 (Hawley-Nelson et al., *EMBO J.* 7:525–531 (1988)) and which encodes the C-terminal portion of the E2 protein. Four synthetic deoxyoligonucleotides were used in the construction described below in detail.

The plasmid ptat72 was cleaved with the restriction endonucleases NdeI and BamHI, releasing the tat encoding portion of the vector. The 4603 base pair (bp) vector fragment was purified by agarose gel electrophoresis, and a 169 base pair (bp) NdeI-AatII fragment of the tat encoding fragment was isolated. The 3' portion of the E2C coding sequence was isolated as a 375 bp StyI-SpeI fragment from pCO-E2 (Hawley-Nelson et al.,*EMBO J.* 7:525–531 (1988); obtained from Dr. Elliot Androphy, Tufts University/New England Medical Center Hospitals). The E2C fragment was connected to the tat fragment and to the expression vector by use of two pairs of complementary deoxyoligonucleotides (synthesized according to standard procedures using an Applied Biosystems 380A DNA Synthesizer). One complementary pair of oligonucleotides was designed to join the AatII overhang of the tat fragment to the StyI overhang of the E2C fragment. The complementary pair of oligonucleotides consisted of oligonucleotides 374-3 (SEQ ID NO:64) and 374-4 (SEQ ID NO:65). A second pair of complementary oligonucleotides was designed to link the SpeI overhang of the E2C fragment to the BamHI overhang of the 4603 bp vector backbone isolated from ptat72. The second pair of complementary oligonucleotides consisted of oligonucleotides 374-5 (SEQ ID NO:66) and 374-6 (SEQ ID NO:67). The tat fragment, the E2C fragment and the two pairs of oligos were inserted into the 4603 ptat72 vector backbone to create pFTE103. The resulting fusion gene is designed to express a protein comprising amino acids 1 through 67 of tat at the amino terminus followed by the C-terminal 105 amino acids of E2 (residues 306 through 410 of BPV-1 E2).

The tat-responsive reporter construct pXB318 was constructed in three steps. The starting plasmid was pBG312 (Cate et al., *Cell* 45:685–698 (1986)). Two oligodeoxynucleotides, with sequences consisting of (SEQ ID NO:68) and (SEQ ID NO:69), were synthesized, which when annealed have an AatII-compatible overhang at the 5' end and an EcoRI-compatible overhang at the 3' end, and form a polylinker with internal XhoI, HindIII and BamHI restriction sites. Plasmid pBG312 was cleaved with AatII and EcoRI to remove the promoter, and the above polylinker was inserted into the vector to form the promoterless vector pXB100. The HIV-1 long terminal repeat (LTR) from pU3R-III (Sodroski et al. *Science* 227:171–173 (1985)) was excised as a XhoI-HindIII fragment and was inserted into XhoI and HindIII sites of the polylinker of pXB100 to create pXB301. The human tissue plasminogen activator (tPA) cDNA reporter was excised as a BamHI fragment from pTPA114 (Fisher et al., *J. Biol. Chem.* 260:11223–11230 (1985)) and inserted into the BamHI site of pXB301 to create pXB318.

Expression and Purification of TatE2C

The TatE2C fusion protein was expressed in *E. coli* using the vector pFTE103 and the T7 RNA polymerase expression system precisely as described by Studier et al. (Studier et al., *Methods in Enzymology* 185:60–89 (1990)). Virtually all of the TatE2C protein was found in the insoluble fraction. The following purification was performed:

1. *E. coli* were pelleted, resuspended in ten packed cell volumes of 25 mM Tris-HCl pH 7.5, 1 mM EDTA, 10 mM DTT, and 1 mM PMSF and lysed with two passages through a French press.
2. The membrane fraction was pelleted by centrifugation at 10,000 rpm for 30 minutes.
3. This membrane fraction was resuspended in 6 M urea.
4. Solid guanidine-HCl was added to a final concentration of 6 M and DTT was added to a final concentration of 10 mM.
5. After 30 minutes at 37° C., the solution was clarified by centrifugation at 10,000 rpm for 30 minutes.
6. The sample was loaded onto an A.5 agarose gel filtration column in 6 M guanidine-HCl, 50 mM sodium phosphate pH 5.4, and 10 mM DTT.
7. TatE2C-containing fractions were loaded onto a $C_{18}$ reverse phase HPLC column and eluted with a gradient of 0–75% acetonitrile in 0.1% trifluoroacetic acid.

TatE2C protein appeared in a single peak. On protein gels, the TatE2C fusion protein migrated with an apparent molecular weight of 20,000 to 21,000 daltons.

Assay of TatE2C Uptake by Tat Activity

Uptake was detected either as tat activity (activation of a tat-dependent reporter in HeLa.318) or by indirect immunofluorescence using anti-E2 antibodies. Tat activity was determined by adding tat protein (amino acids 1–72) or TatE2C fusion protein at 2.5–250 nM along with chloroquine at 0.1 mM to the culture medium of HeLa.318 cells in 24 well plates essentially by the method of Frankel and Pabo (Frankel, A. D. and Pabo, C. O., *Cell* 55:1189–1193 (1988)). The culture medium was harvested 24 hours later and assayed for tPA activity by the method of Granelli-Piperno and Reich (*J. Exp. Med.* 148:223–234 (1978)). Cell numbers were determined and tPA secretion was expressed as $ng/10^6$ cells per day. tPA secretion was undetectable in the absence of added tat or TatE2C protein (less than 0.1 $ng/10^6$ cells per day).

Assay of TatE2C Uptake by E2-Specific Immunofluorescence For indirect immunofluorescence, mouse 3T3 cells were seeded into LAB-TEK four chamber tissue culture chamber/slides. On the next day, TatE2C protein and chloroquine were added to the culture medium to final concentrations of 250 nM and 0.1 mM, respectively. Six hours later, immunofluorescence was performed as follows:

1. Medium was removed and wells were washed twice with phosphate-buffered saline (PBS).
2. Cells were fixed by treatment with 3.5%. formaldehyde for 10 minutes at room temperature.
3. Cells were permeabilized in 0.2% Triton X-100/2% bovine serum albumin (BSA) in PBS with 1 mM $MgCl_2$/ 0.1 mM $CaCl_2$ (PBS+) for 5 minutes at room temperature.
4. Cells were blocked by treatment with whole goat serum (Cappel #5506-1380) at a 1:30 dilution in PBS+/2% BSA for one hour at 4° C.
5. The primary antibody was an affinity purified rabbit polyclonal which had been raised by injection of purified protein E2. C85 (in this case the carboxy terminal 85 amino acids expressed in bacteria using the T7 polymerase expression system) into a rabbit, followed by purification by passage of the bleed over an E2 affinity column. This antibody was added to the wells at a 1:100 dilution in PBS+/2% BSA for one hour at 4° C.
6. The secondary antibody was a rhodamine conjugated goat anti-rabbit IgG (Cappel #2212-0081). This antibody was added at a 1:100 dilution in PBS+/0.2% BSA for 30 minutes at 4° C.
7. Wells were washed three times with PBS+/0.2% Tween-20/2% BSA.

8. Slides were mounted in 50% glycerol in PBS and viewed with a fluorescent microscope with a rhodamine filter.

As a control, purified E2C protein (the carboxy terminal 85 amino acids which were found to be recognized by the polyclonal antibody preparation) was added to wells in the same manner as the TatE2C fusion protein.

EXAMPLE 1

Production and Purification of Transport Polypeptides

Recombinant DNA

Plasmid pTat72 was a starting clone for bacterial production of tat-derived transport polypeptides and construction of genes encoding transport polypeptide-cargo protein fusions. We obtained plasmid pTat72 (described in Frankel and Pabo, supra and in Example I, above) from Alan Frankel (The Whitehead Institute for Biomedical Research, Cambridge, Mass.). Plasmid pTat72, was derived from the pET-3a expression vector of F. W. Studier et al. ("Use of T7 RNA Polymerase to Direct Expression of Cloned Genes", *Methods Enzymol.*, 185, pp. 60–90 (1990)) by insertion of a synthetic gene encoding amino acids 1 to 72 of HIV-1 tat. The tat coding region employs *E.coli* codon usage and is driven by the bacteriophage T7 polymerase promoter inducible with isopropyl beta-D-thiogalactopyranoside ("IPTG"). Tat protein constituted 5% of total *E.coli* protein after IPTG induction.

Purification of Tat1-72 from Bacteria

We suspended *E.coli* expressing tat1-72 protein in 10 volumes of 25 mM Tris-HCl (pH 7.5), 1 mM EDTA. We lysed the cells in a French press and removed the insoluble debris by centrifugation at 10,000×g for 1 hour. We loaded the supernatant onto a Q Sepharose Fast Flow (Pharmacia LKB, Piscataway, N.J.) ion exchange column (20 ml resin/60 ml lysate). We treated the flow-through fraction with 0.5 M NaCl, which caused the tat protein to precipitate. We collected the salt-precipitated protein by centrifugation at 35,000 rpm, in a 50.2 rotor, for 1 hour. We dissolved the pelleted precipitate in 6 M guanidine-HCl and clarified the solution by centrifugation at 35,000 rpm, in a 50.2 rotor, for 1 hour. We loaded the clarified sample onto an A.5 agarose gel filtration column equilibrated with 6 M guanidine-HCl, 50 mM sodium phosphate (pH 5.4), 10 mM DTT, and then eluted the sample with the same buffer. We loaded the tat protein-containing gel filtration fractions onto a $C_4$ reverse phase HPLC column and eluted with a gradient of 0–75% acetonitrile, 0.1% trifluoroacetic acid. Using this procedure, we produced about 20 mg of tat1-72 protein per liter of *E.coli* culture (assuming 6 g of cells per liter). This represented an overall yield of about 50%.

Upon SDS-PAGE analysis, the tat1-72 polypeptide migrated as a single band of 10 kD. The purified tat1-72 polypeptide was active in an uptake/transactivation assay. We added the polypeptide to the culture medium of human hepatoma cells containing a tat-responsive tissue plasminogen activator ("tPA") reporter gene. In the presence of 0.1 mM chloroquine, the purified tat1-72 protein (100 ng/ml) induced tPA expression approximately 150-fold.

Chemical Synthesis of Transport Polypeptides

For chemical synthesis of the various transport polypeptides, we used a commercially-available, automated system (Applied Biosystems Model 430A synthesizer) and followed the system manufacturer's recommended procedures. We removed blocking groups by HF treatment and isolated the synthetic polypeptides by conventional reverse phase HPLC methods. The integrity of all synthetic polypeptides was confirmed by mass spectrometer analysis.

EXAMPLE 2

β-Galactosidase Conjugates

Chemical Cross-Linking with SMCC

For acetylation of β-galactosidase (to block cysteine sulfhydryl groups) we dissolved 6.4 mg of commercially obtained β-galactosidase (Pierce Chem. Co., cat. no. 32101G) in 200 μl of 50 mM phosphate buffer (pH 7.5). To the 200 μl of β-galactosidase solution, we added 10 μl of iodoacetic acid, prepared by dissolving 30 mg of iodoacetic acid in 4 ml of 50 mM phosphate buffer (pH 7.5). (In subsequent experiments we found iodoacetamide to be a preferable substitute for iodoacetic acid.) We allowed the reaction to proceed for 60 minutes at room temperature. We then separated the acetylated β-galactosidase from the unreacted iodoacetic acid by loading the reaction (Pharmacia) mixture on a small G-25 (Pharmacia LKB, Piscataway, N.J.) gel filtration column and collecting the void volume.

Prior to SMCC activation of the amine groups of the acetylated β-galactosidase, we concentrated 2 ml of the enzyme collected from the G-25 column to 0.3 ml in a Centricon 10 (Amicon, Danvers, Mass.) ultrafiltration apparatus. To the concentrated acetylated β-galactosidase, we added 19 μg of sulfo-SMCC (Pierce Chem. Co., cat. No. 22322G) dissolved in 15 μl of dimethylformamide ("DMF"). We allowed the reaction to proceed for 30 minutes at room temperature. We then separated the β-galactosidase-SMCC from the DMF and unreacted SMCC by passage over a small G-25 gel filtration column.

For chemical cross-linking of transport polypeptides to β-galactosidase, we mixed the solution of β-galactosidase-SMCC with 100 μg of transport polypeptide (tat1-72, tat37-72, tat38-58GGC, tat37-58, tat47-58GGC or tatCGG47-58) dissolved in 200 μl of 50 mM phosphate buffer (pH 7.5). We allowed the reaction to proceed for 60 minutes at room temperature. We then isolated the transport polypeptide-β-galactosidase conjugate by loading the reaction mixture on an S-200HR gel filtration column and collecting the void volume.

The transport polypeptide-β-galactosidase conjugate thus obtained yielded positive results when assayed for tat in conventional Western blot and ELISA analyses performed with rabbit anti-tat polyclonal antibodies. For a general discussion of Western blot and ELISA analysis, see E. Harlow and D. Lane, *Antibodies: A Laboratory Manual*, Cold Spring Harbor Laboratory (1988). Gel filtration analysis with Superose 6 (Pharmacia LKB, Piscataway, N.J.) indicated the transport polypeptide-β-galactosidase conjugate to have a molecular weight of about 540,000 daltons. Specific activity of the transport polypeptide-β-galactosidase conjugate was 52% of the specific activity of the β-galactosidase starting material, when assayed with o-nitrophenyl-β-D-galactopyranoside ("ONPG"). The ONPG assay procedure is described in detail at pages 16.66–16.67 of Sambrook et al. (supra).

Cellular Uptake of β-Galactosidase Conjugates

We added the conjugates to the medium of HeLa cells (ATCC no. CCL2) at 20 μg/ml, in the presence or absence of 100 μM chloroquine. We incubated the cells for 4–18 hours at 37° C./5.5% $CO_2$. We fixed the cells with 2% formaldehyde, 0.2% glutaraldehyde in phosphate-buffered saline ("PBS") for 5 minutes at 4° C. We then washed the cells three times with 2 mM $MgCl_2$ in PBS, and stained them with X-gal, at 37° C. X-gal is a colorless β-galactosidase substrate (5-bromo-4-chloro-3-indolyl D-galactoside) that yields a blue product upon cleavage by β-galactosidase. Our X-gal staining solution contained 1 mg of X-gal (Bio-Rad, Richmond, Calif., cat. No. 170-3455) per ml of PBS containing 5 mM potassium ferricyanide, 5 mM potassium ferrocyanide and 2 mM $MgCl_2$.

We subjected the stained cells to microscopic examination at magnifications up to 400×. Such microscopic examination revealed nuclear staining, as well as cytoplasmic staining.

The cells to which the tat37-72-β-galactosidase conjugate or tat1-72-β-galactosidase conjugate was added stained dark blue. β-galactosidase activity could be seen after a development time as short as 15 minutes. For comparison, it should be noted that stain development time of at least 6 hours is normally required when β-galactosidase activity is introduced into cells by means of transfection of the β-galactosidase gene. Nuclear staining was visible in the absence of chloroquine, although the nuclear staining intensity was slightly greater in chloroquine-treated cells. Control cells treated with unconjugated β-galactosidase showed no detectable staining.

Cleavable Conjugation by Direct Disulfide

Each β-galactosidase tetramer has 12 cysteine residues that may be used for direct disulfide linkage to a transport polypeptide cysteine residue. To reduce and then protect the sulfhydryl of tat37-72, we dissolved 1.8 mg (411 nmoles) of tat37-72 in 1 ml of 50 mM sodium phosphate (pH 8.0), 150 mM NaCl, 2 mM EDTA, and applied the solution to a Reduce-Imm column (Pierce Chem. Co., Rockford, Ill.). After 30 minutes at room temperature, we eluted the tat37-72 from the column with 1 ml aliquots of the same buffer, into tubes containing 0.1 ml of 10 mM 5,5'-dithio-bis(2-nitrobenzoic acid) ("DTNB"). We left the reduced tat37-72 polypeptide in the presence of the DTNB for 3 hours. We then removed the unreacted DTNB from the tat37-72-TNB by gel filtration on a 9 ml Sephadex G-10 column (Pharmacia LKB, Piscataway, N.J.). We dissolved 5 mg β-galactosidase in 0.5 ml of buffer and desalted it on a 9 ml Sephadex G-25 column (Pharmacia LKB, Piscataway, N.J.), to obtain 3.8 mg of β-galactosidase/ml buffer. We mixed 0.5 ml aliquots of desalted β-galactosidase solution with 0.25 or 0.5 ml of the tat37-72-TNB preparation, and allowed the direct disulfide cross-linking reaction to proceed at room temperature for 30 minutes. We removed the unreacted tat37-72-TNB from the β-galactosidase conjugate by gel filtration on a 9 ml Sephacryl S-200 column. We monitored the extent of the cross-linking reaction indirectly, by measuring absorbance at 412 nm due to the released TNB. The direct disulfide conjugates thus produced were taken up into cells (data not shown).

Cleavable Conjugation with SPDP

We used the heterobifunctional cross-linking reagent ("SPDP"), which contains a cleavable disulfide bond, to form a cross-link between: (1) the primary amine groups of β-galactosidase and the cysteine sulfhydryls of tat1-72 (metabolically labelled with $^{35}S$); or (2) the primary amine groups of rhodamine-labelled β-galactosidase and the amino terminal cysteine sulfhydryl of tat37–72.

For the tat1-72 conjugation, we dissolved 5 mg of β-galactosidase in 0.5 ml of 50 mM sodium phosphate (pH 7.5), 150 mM NaCl, 2 mM $MgCl_2$, and desalted the β-galactosidase on a 9 ml Sephadex G-25 column (Pharmacia LKB, Piscataway, N.J.). We treated the desalted β-galactosidase with an 88-fold molar excess of iodoacetamide at room temperature for 2 hours, to block free sulfhydryl groups. After removing the unreacted iodoacetamide by gel filtration, we treated the blocked β-galactosidase with a 10-fold molar excess of SPDP at room temperature. After 2 hours, we exchanged the buffer, by ultrafiltration (Ultrafree 30, Millipore, Bedford, Mass.). We then added a 4-fold molar excess of labelled tat1-72, and allowed the cross-linking reaction to proceed overnight, at room temperature. We removed the unreacted tat1-72 by gel filtration on a 9 ml Sephacryl S-200 column. Using the known specific activity of the labelled tat1-72, we calculated that there were 1.1 tat1-72 polypeptides cross-linked per β-galactosidase tetramer. Using the ONPG assay, we found that the conjugated β-galactosidase retained 100% of its enzymatic activity. Using measurement of cell-incorporated radioactivity and X-gal staining, we demonstrated uptake of the conjugate into cultured HeLa cells.

For the tat37-72 conjugation, our procedure was as described in the preceding paragraph, except that we labelled the β-galactosidase with a 5:1 molar ratio of rhodamine maleimide at room temperature for 1 hour, prior to the iodoacetamide treatment (100:1 iodoacetamide molar excess). In the cross-linking reaction, we used an SPDP ratio of 20:1, and a tat37-72 ratio of 10:1. We estimated the conjugated product to have about 5 rhodamine molecules (according to UV absorbance) and about 2 tat37-72 moieties (according to gel filtration) per β-galactosidase tetramer. The conjugate from this procedure retained about 35% of the initial β-galactosidase enzymatic activity. Using X-gal staining and rhodamine fluorescence, we demonstrated that the SPDP conjugate was taken up into cultured HeLa cells.

EXAMPLE 3

Animal Studies with β-Galactosidase Conjugates

For conjugate half-life determination and biodistribution analysis, we injected either 200 μg of SMCC-β-galactosidase (control) or tat1-72-β-galactosidase intravenously ("IV") into the tail veins of Balb/c mice (Jackson Laboratories), with and without chloroquine. We collected blood samples at intervals up to 30 minutes. After 30 minutes, we sacrificed the animals and removed organs and tissues for histochemical analysis.

We measured β-galactosidase activity in blood samples by the ONPG assay. The ONPG assay procedure is described in detail at pages 16.66–16.67 of Sambrook et al. (supra). β-galactosidase and tat1-72-β-galactosidase were rapidly cleared from the bloodstream. We estimated their half-lives at 3–6 minutes. These experimental comparisons indicated that attachment of the tat1-72 transport polypeptide has little or no effect on the clearance rate of β-galactosidase from the blood.

To detect cellular uptake of the transport polypeptide-β-galactosidase conjugates, we prepared thin frozen tissue sections from sacrificed animals (above), carried out fixation as described in Example 2 (above), and subjected them to a standard X-gal staining procedure. Liver, spleen and heart stained intensely. Lung, and skeletal muscle stained less intensely. Brain, pancreas and kidney showed no detectable staining. High power microscopic examination revealed strong cellular, and in some cases, nuclear staining of what appeared to be endothelial cells surrounding the blood supply to the tissues.

EXAMPLE 4

Cellular Uptake Tests with β-Galactosidase-Polyarginine and β-Galactosidase-Polylysine Conjugates To compare the effectiveness of simple basic amino acid polymers with the effectiveness of our tat-derived transport polypeptides, we conjugated commercially available polyarginine (Sigma Chem Co., St. Louis, Mo., cat. No.

P-4663) and polylysine (Sigma cat. No. P-2658) to β-galactosidase, as described in Example 2, above. We added the conjugates to the medium of HeLa cells at 1–30 μg/ml, with and without chloroquine. Following incubation with the conjugates, we fixed, stained and microscopically examined the cells as described in Example 2, above.

The polylysine-β-galactosidase conjugate gave low levels of surface staining and no nuclear staining. The polyarginine-β-galactosidase conjugate gave intense overall staining, but showed less nuclear stain than the tat1-72-β-galactosidase and tat37-72-β-galactosidase conjugates. To distinguish between cell surface binding and actual internalization of the polyarginine-β-galactosidase conjugate, we treated the cells with trypsin, a protease, prior to the fixing and staining procedures. Trypsin treatment eliminated most of the X-gal staining of polyarginine-β-galactosidase treated cells, indicating that the polyarginine-β-galactosidase conjugate was bound to the outside surfaces of the cells rather than actually internalized. In contrast, cells exposed to the tat1-72 or 37-72-β-galactosidase conjugates stained despite trypsin treatment, indicating that the β-galactosidase cargo was inside the cells and thus protected from trypsin digestion. Control cells treated with unconjugated β-galactosidase showed no detectable staining.

EXAMPLE 5

Horseradish Peroxidase Conjugates

Chemical Cross-Linking

To produce tat1-72-HRP and tat37-72-HRP conjugates, we used a commercially-available HRP coupling kit (Immunopure maleimide activated HRP, Pierce Chem. Co., cat. No. 31498G). The HRP supplied in the kit is in a form that is selectively reactive toward free —SH groups. (Cysteine is the only one of the 20 protein amino acids having a free —SH group.) In a transport polypeptide-HRP conjugation experiment involving tat1-72, we produced the tat1-72 starting material in E.coli and purified it by HPLC, as described in Example 1, above. We lyophilized 200 μg of the purified tat1-72 (which was dissolved in TFA/acetonitrile) and redissolved it in 100 μl of 100 mM HEPES buffer (pH7.5), 0.5 mM EDTA. We added 50 μl of the tat1-72 or tat37-72 solution to 50 μl of Immunopure HRP (750 μg of the enzyme) in 250 mM triethanolamine (pH 8.2). We allowed the reaction to proceed for 80 minutes, at room temperature. Under these conditions, approximately 70% of the HRP was chemically linked to tat1-72 molecules. We monitored the extent of the linking reaction by SDS-PAGE analysis.

Cellular Uptake of HRP Conjugates

We added the conjugates to the medium of HeLa cells at 20 μg/ml, in the presence or absence of 100 μM chloroquine. We incubated the cells for 4–18 hours at 37° C./5.5% $CO_2$. We developed the HRP stain using 4-chloro-1-naphthol (Bio-Rad, Richmond, Calif., cat. No. 170-6431) and hydrogen peroxide HRP substrate. In subsequent experiments, we substituted diaminobenzidine (Sigma Chem. Co., St. Louis, Mo.) for 4-chloro-1-naphthol.

Cells to which we added transport polypeptide-HRP conjugates displayed cell-associated HRP activity. Short time periods of conjugate exposure resulted in staining patterns which appeared punctate, probably reflecting HRP in endocytic vesicles. Following longer incubations, we observed diffuse nuclear and cytoplasmic staining. Control cells treated with unconjugated HRP showed no detectable staining.

EXAMPLE 6

PE ADP Ribosylation Domain Conjugates

We cloned and expressed in E.coli the Pseudomonas exotoxin ("PE") both in its full length form and in the form of its ADP ribosylation domain. We produced transport polypeptide-PE conjugates both by genetic fusion and chemical cross-linking.

Plasmid Construction

To construct plasmid pTat70(ApaI), we inserted a unique ApaI site into the tat open reading frame by digesting pTat72 with BamH1 and EcoR1, and inserting a double-stranded linker consisting of the following synthetic oligonucleotides:

GATCCCAGAC CCACCAGGTT TCTCTGTCGG GCCCTTAAG (SEQ ID NO:8)

AATTCTTAAG GGCCCGACAG AGAAACCTGG TGGGTCTGG (SEQ ID NO:9).

The linker replaced the C-terminus of tat, LysGlnStop, with GlyProStop. The linker also added a unique ApaI site suitable for in-frame fusion of the tat sequence with the PE ADP ribosylation domain-encoding sequences, by means of the naturally-occurring ApaI site in the PE sequence. To construct plasmid pTat70PE (SEQ ID NO:10), we removed an ApaI-EcoRI fragment encoding the PE ADP ribosylation domain, from plasmid CD4(181)-PE(392). The construction of CD4(181)-PE(392) is described by G. Winkler et al. ("CD4-Pseudomonas Exotoxin Hybrid Proteins: Modulation of Potency and Therapeutic Window Through Structural Design and Characterization of Cell Internalization", *AIDS Research and Human Retroviruses*, 7, pp. 393–401 (1991)). We inserted the ApaI-EcoRI fragment into pTat70(ApaI) digested with ApaI and EcoR1.

To construct plasmid pTat8PE (SEQ ID NO:11), we removed a 214-base pair NdeI-ApaI fragment from pTat70PE and replaced it with a double-stranded linker having NdeI and ApaI cohesive termini, encoding tat residues 1–4 and 67–70, and consisting of the following synthetic oligonucleotides:

TATGGAACCG GTCGTTTCTC TGTCGGGCC (SEQ ID NO:12)

CGACAGAGAA ACGACCGGTT CCA (SEQ ID NO:13).

Purification of TAT8-PE

Figure 8:
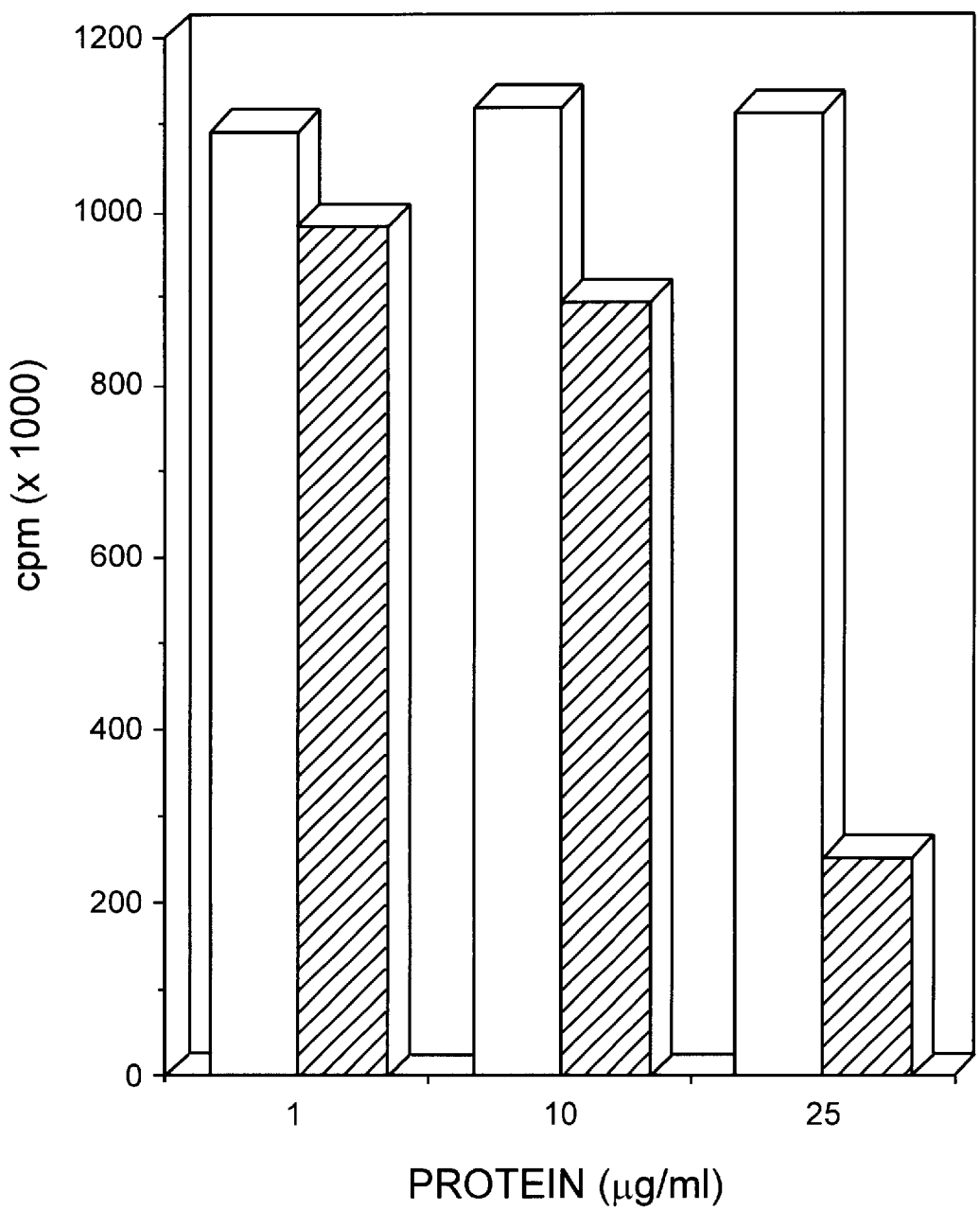
FIG. 8 summarizes the results of cellular uptake experiments with transport polypeptide-Pseudomonas exotoxin ribosylation domain conjugates (non-hatched bars, unconjugated; diagonally-hatched bars, conjugated).

Expression of the pTat8-PE construct yielded the PE ADP ribosylation domain polypeptide fused to amino acids 1–4 and 67–70 of tat protein. The pTat8-PE expression product ("tat8-PE") served as the PE ADP ribosylation domain moiety (and the unconjugated control) in chemical cross-linking experiments described below. Codons for the 8 tat amino acids were artifacts from a cloning procedure selected for convenience. The 8 tat amino acids fused to the PE ADP ribosylation domain had no transport activity (FIG. 8).

For purification of tat8-PE, we suspended 4.5 g of pTat8-PE-transformed E.coli in 20 ml of 50 mM Tris-HCl (pH 8.0), 2mM EDTA. We lysed the cells in a French press and removed insoluble debris by centrifugation at 10,000 rpm for 1 hour, in an SA600 rotor. Most of the tat8-PE was in the supernatant. We loaded the supernatant onto a 3 ml Q-Sepharose Fast Flow (Pharmacia LKB, Piscataway, N.J.) ion exchange column. After loading the sample, we washed the column with 50 mM Tris-HCl (pH 8.0), 2 mM EDTA. After washing the column, we carried out step gradient elution, using the same buffer with 100, 200 and 400 mM NaCl. The tat8-PE eluted with 200 mM NaCl. Following the ion exchange chromatography, we further purified the tat8-PE by gel filtration on a Superdex 75 FPLC column (Pharmacia LKB, Piscataway, N.J.). We equilibrated the gel filtration column with 50 mM HEPES (pH 7.5). We then loaded the sample and carried out elution with the equilibration buffer at 0.34 ml/min. We collected 1.5-minute fractions and stored the tat8-PE fractions at –70° C.

Crosslinking of TAT8-PE

Since the PE ADP ribosylation domain has no cysteine residues, we used sulfo-SMCC (Pierce Chem. Co., Rockford, Ill. cat No. 22322 G) for transport polypeptide-tat8-PE conjugation. We carried out the conjugation in a 2-step reaction procedure. In the first reaction step, we treated tat8-PE (3 mg/ml), in 50 mM HEPES (pH 7.5), with 10 mM sulfo-SMCC, at room temperature, for 40 minutes. (The sulfo-SMCC was added to the reaction as a 100 mM stock solution in 1 M HEPES, pH 7.5.) We separated the tat8-PE-sulfo-SMCC from the unreacted sulfo-SMCC by gel filtration on a P6DG column (Bio-Rad, Richmond, Calif.) equilibrated with 25 mM HEPES (pH 6.0), 25 mM NaCl. In the second reaction step, we allowed the tat8-PE-sulfo-SMCC (1.5 mg/ml 100 mM HEPES (pH 7.5), 1 mM EDTA) to react with purified tat37–72 (600 μM final conc.) at room temperature, for 1 hour. To stop the cross-linking reaction, we added cysteine. We analyzed the cross-linking reaction products by SDS-PAGE. About 90% of the tat8-PE became cross-linked to the tat37-72 transport polypeptide under these conditions. Approximately half of the conjugated product had one transport polypeptide moiety, and half had two transport polypeptide moieties.

Cell-Free Assay for PE ADP Ribosylation

To verify that the PE ribosylation domain retained its biological activity (i.e., destructive ribosome modification) following conjugation to transport polypeptides, we tested the effect of transport polypeptide-PE ADP ribosylation conjugates on in vitro (i.e., cell-free) translation. For each in vitro translation experiment, we made up a fresh translation cocktail and kept it on ice. The in vitro translation cocktail contained 200 μl rabbit reticulocyte lysate (Promega, Madison, Wis.), 2 μl 10 mM $ZnCl_2$ (optional), 4 μl of a mixture of the 20 protein amino acids except methionine, and 20 μl $^{35}$S-methionine. To 9 μl of translation cocktail we added from 1 to 1000 ng of transport polypeptide-PE conjugate (preferably in a volume of 1 μl) or control, and pre-incubated the mixture for 60 minutes at 30° C. We then added 0.5 μl BMV RNA to each sample and incubated for an additional 60 minutes at 30° C. We stored the samples at −70° C. after adding 5 μl of 50% glycerol per sample. We analyzed the in vitro translation reaction products by SDS-PAGE techniques. We loaded 2 μl of each translation reaction mixture (plus an appropriate volume of SDS-PAGE sample buffer) per lane on the SDS gels. After electrophoresis, we visualized the $^{35}$S-containing in vitro translation products by fluorography.

Using the procedure described in the preceding paragraph, we found that the PE ADP ribosylation domain genetically fused to the tat1-70 transport polypeptide had no biological activity, i.e., did not inhibit in vitro translation. In contrast, using the same procedure, we found that the PE ADP ribosylation domain chemically cross-linked to the tat37-72 transport polypeptide had retained full biological activity, i.e., inhibited in vitro translation as well as the non-conjugated PE ADP ribosylation domain controls.

Cytotoxicity Assay for PE ADP Ribosylation

In a further test involving the tat37-72-PE ADP ribosylation domain conjugate, we added it to cultured HeLa cells in the presence or absence of 100 μM chloroquine. We then assayed cytotoxicity by measuring in vivo protein synthesis, as indicated by trichloroacetic acid ("TCA")-precipitable radioactivity in cell extracts.

We performed the cytotoxicity assay as follows. We disrupted HeLa cell layers, centrifuged the cells and resuspended them at a density of $2.5\times10^4$/ml of medium. We used 0.5 ml of suspension/well when using 24 well plates, or 0.25 ml of suspension/well when using 48 well plates. We added conjugates or unconjugated controls, dissolved in 100 μl of PBS, to the wells after allowing the cells to settle for at least 4 hours. We incubated the cells in the presence of conjugates or controls for 60 minutes, at 37° C., then added 0.5 ml of fresh medium to each cell, and incubated the cells for an additional 5–24 hours. Following this incubation, we removed the medium from each well and washed the cells once with about 0.5 ml PBS. We then added 1 μCi of $^{35}$S-methionine (Amersham) per 100 μl per well in vivo cell labelling grade SJ.1015), and incubated the cells for 2 hours. After two hours, we removed the radioactive medium and washed the cells 3 times with cold 5% TCA and then once with PBS. We added 100 μl of 0.5 M NaOH to each well and allowed at least 45 minutes for cell lysis and protein dissolving to take place. We then added 50 μl 1 M HCl to each well and transferred the entire contents of each well into scintillation fluid for liquid scintillation measurement of radioactivity.

In the absence of chloroquine, there was a clear dose-dependent inhibition of cellular protein synthesis in response to treatment with the transport polypeptide-PE ADP ribosylation domain conjugate, but not in response to treatment with the unconjugated PE ADP ribosylation domain. When conjugated to tat37-72, the PE ADP ribosylation domain appeared to be transported 3 to 10-fold more efficiently than when conjugated to tat1-72. We also conjugated transport polypeptides tat38-58GGC, tat37-58, tat47-58GGC and tatCGG-47-58 to the PE ADP ribosylation domain. All of these conjugates resulted in cellular uptake of biologically active PE ADP ribosylation domain (data not shown).

EXAMPLE 7

Ribonuclease Conjugates

Chemical Cross-Linking

We dissolved 7.2 mg of bovine pancreatic ribonuclease A, Type 12A (Sigma Chem. Co., St. Louis, Mo., cat. No. R5500) in 200 μl PBS (pH 7.5). To the ribonuclease solution, we added 1.4 mg sulfo-SMCC (Pierce Chem. Co., Rockford, Ill., cat. No. 22322H). After vortex mixing, we allowed the reaction to proceed at room temperature for 1 hour. We removed unreacted SMCC from the ribonuclease-SMCC by passing the reaction mixture over a 9 ml P6DG column (Bio-Rad, Richmond, Calif.) and collecting 0.5 ml fractions. We identified the void volume peak fractions (containing the ribonuclease-SMCC conjugate) by monitoring UV absorbance at 280 nm. We divided the pooled ribonuclease-SMCC-containing fractions into 5 equal aliquots. To each of 4 ribonuclease-SMCC aliquots, we added a chemically-synthesized transport polypeptide corresponding to tat residues: 37-72 ("37-72"); 38-58 plus GGC at the carboxy terminal ("38-58GGC"); 37-58 ("CGG37-58"); or 47-58 plus CGG at the amino terminal ("CGG47-58"). We allowed the transport polypeptide-ribonuclease conjugation reactions to proceed for 2 hours at room temperature, and then overnight at 4° C. We analyzed the reaction products by SDS-PAGE on a 10–20% gradient gel. The cross-linking efficiency was approximately 60% for transport polypeptides tat38-58GGC, tat37-58 and tatCGG47-58, and 40% for tat37-72. of the modified species, 72% contained one, and 25% contained 2 transport polypeptide substitutions.

Cellular Uptake of Tat37-72-Ribonuclease Conjugates

We maintained cells at 37° C. in a tissue culture incubator in Dulbecco's Modified Eagle Medium supplemented with 10% donor calf serum and penicillium/streptomycin. For cellular uptake assays, we plated $10^5$ cells in a 24-well plate and cultured them overnight. We washed the cells with Dulbecco's PBS and added the ribonuclease conjugate dissolved in 300 μl of PBS containing 80 μM chloroquine, at concentrations of 0, 10, 20, 40 and 80 μg/ml. After a 1.25 hour incubation at 37° C., we added 750 μl of growth medium and further incubated the cell samples overnight. After the overnight incubation, we washed the cells once with PBS and incubated them for 1 hour in Minimal Essential Medium without methionine (Flow Labs) (250 μl/well) containing $^{35}$S methionine (1 μCi/well). After the 1 hour incubation with radioactive methionine, we removed the medium and washed the cells three times 5% TCA (1 ml/well/wash). We then added 250 μl of 0.5 M NaOH per well. After 1 hour at room temperature, we pipetted 200 μl of the contents of each well into a scintillation vial, added 100 μl of 1 M HCl and 4 ml of scintillation fluid. After thorough mixing of the contents of each vial, we measured radioactivity in each sample by liquid scintillation counting.

Figure 9:
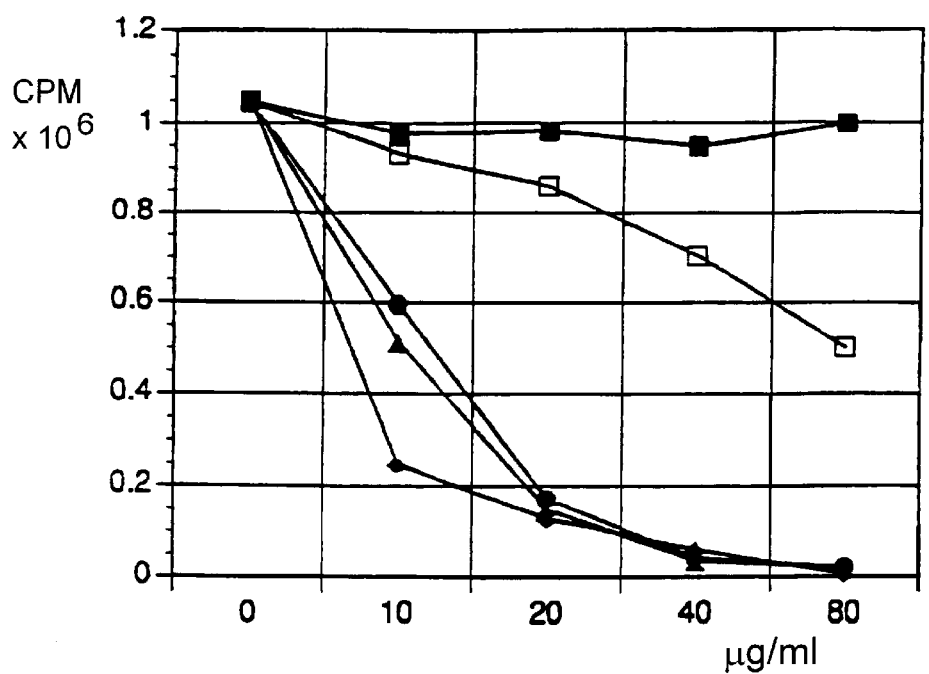
FIG. 9 summarizes the results of cellular uptake experiments with transport polypeptide-ribonuclease conjugates (closed squares, ribonuclease-SMCC without transport moiety; closed circles, tat37-72-ribonuclease; closed triangles tat38-58-GGC-ribonuclease; closed diamonds, tatCGG38-58-ribonuclease; open squares, tatCGG47-58-ribonuclease).

The cellular uptake results are summarized in FIG. 9. Transport polypeptide tat38-58GGC functioned as well as, or slightly better than tat37-72. Transport polypeptide tatCGG47-58 had reduced activity (data not shown). We do not know whether this polypeptide had reduced uptake activity or whether the proximity of the basic region to the ribonuclease interfered with enzyme activity.

We have used cation exchange chromatography (BioCAD perfusion chromatography system, PerSeptive Biosystems) to purify ribonuclease conjugates having one or two transport polypeptide moieties.

EXAMPLE 8

Protein Kinase A Inhibitor Conjugates
Chemical Cross-Linking

We purchased the protein kinase A inhibitor ("PKAI") peptide (20 amino acids) from Bachem California (Torrence, Calif.). For chemical cross-linking of PKAI to transport polypeptides, we used either sulfo-MBS (at 10 mM) or sulfo-SMPB (at 15 mM). Both of these cross-linking reagents are heterobifunctional for thiol groups and primary amine groups. Since PKAI lacks lysine and cysteine residues, both sulfo-MBS and sulfo-SMPB selectively target cross-linking to the amino terminus of PKAI. We reacted PKAI at a concentration of 2 mg/ml, in the presence of 50 mM HEPES (pH 7.5), 25 mM NaCl, at room temperature, for 50 minutes, with either cross-linking reagent. The sulfo-MBS reaction mixture contained 10 mM sulfo-MBS and 20% DMF. The sulfo-SMPB reaction mixture contained 15 mM sulfo-SMPB and 20% dimethylsulfoxide ("DMSO"). We purified the PKAI-cross-linker adducts by reverse phase HPLC, using a $C_4$ column. We eluted the samples from the $C_4$ column in a 20–75% acetonitrile gradient containing 0.1% trifluoroacetic acid. We removed the acetonitrile and trifluoroacetic acid from the adducts by lyophilization and redissolved them in 25 mM HEPES (pH 6.0), 25 mM NaCl. We added tat1-72 or tat37-72 and adjusted the pH of the reaction mixture to 7.5, by adding 1 M HEPES (pH 7.5) to 100 mM. We then allowed the cross-linking reaction to proceed at room temperature for 60 minutes.

We regulated the extent of cross-linking by altering the transport polypeptide:PKAI ratio. We analyzed the cross-linking reaction products by SDS-PAGE. With tat37-72, a single new electrophoretic band formed in the cross-linking reactions. This result was consistent with the addition of a single tat37-72 molecule to a single PKAI molecule. With tat1-72, six new products formed in the cross-linking reactions. This result is consistent with the addition of multiple PKAI molecules per tat1-72 polypeptide, as a result of the multiple cysteine residues in tat1-72. When we added PKAI to the cross-linking reaction in large molar excess, we obtained only conjugates containing 5 or 6 PKAI moieties per tat1-72.

In Vitro Phosphorylation Assay for PKAI Activity

To test the sulfo-MBS-cross-linked conjugates for retention of PKAI biological activity, we used an in vitro phosphorylation assay. In this assay, histone V served as the substrate for phosphorylation by protein kinase A in the presence or absence of PKAI (or a PKAI conjugate). We then used SDS-PAGE to monitor PKAI-dependent differences in the extent of phosphorylation. In each reaction, we incubated 5 units of the catalytic subunit of protein kinase A Sigma) with varying amounts of PKAI or PKAI conjugate, at 37° C., for 30 minutes. The assay reaction mixture contained 24 mM sodium acetate (pH 6.0), 25 mM $MgCl_2$, 100 mM DTT, 50 μCi of [γ-$^{32}$P]ATP and 2 μg of histone V, in a total reaction volume of 40 μl. Using this assay, we found that PKAI conjugated to tat1-72 or tat37-72 inhibited phosphorylation as well as unconjugated PKAI (data not shown).

Cellular Assay

To test for cellular uptake of PKAI and transport polypeptide-PKAI conjugates, we employed cultured cells containing a chloramphenicol acetyltransferase ("CAT") reporter gene under the control of a cAMP-responsive expression control sequence. We thus quantified protein kinase A activity indirectly, by measuring CAT activity. This assay has been described in detail by J. R. Grove et al. ("Probind cAMP-Related Gene Expression with a Recombinant Protein Kinase Inhibitor", *Molecular Aspects of Cellular Regulation*, Vol. 6, P. Cohen and J. G. Folkes, eds., Elsevier Scientific, Amsterdam, pp. 173–95 (1991)).

Using this assay, we found no activity by PKAI or any of the transport polypeptide-PKAI conjugates. This result suggested to us that the PKAI moiety might be undergoing rapid degradation upon entry into the cells.

Cross-Linking of PKAI to Tat37-72-β-Galactosidase

We had previously found cellular uptake of tat37-72-β-galactosidase to be chloroquine-independent (Example 2, above). Therefore, we cross-linked PKAI to tat37-72-β-galactosidase for possible protection of PKAI against rapid degradation.

We treated β-galactosidase with 20 mM DTT (a reducing agent) at room temperature for 30 minutes and then removed the DTT by gel filtration on a G50 column in MES buffer (pH 5). We allowed the reduced β-galactosidase to react with SMPB-activated PKAI (above), at pH 6.5, for 60 minutes. To block residual free sulfhydryl groups, we added N-ethylmaleimide or iodoacetamide. SDS-PAGE analysis showed that at least 95% of the β-galactosidase had been conjugated. About 90% of the conjugated beta-galactosidase product contained one PKAI moiety per subunit, and about 10% contained 2 PKAI moieties. We treated the PKAI-β-galactosidase conjugate with a 10-fold molar excess of sulfo-SMCC. We then reacted the PKAI-β-galactosidase-SMCC with tat1-72. According to SDS-PAGE analysis, the PKAI-β-galactosidase:tat1-72 ratio appeared to be 1:0.5. We have produced about 100 μg of the final product. Because of precipitation problems, the concentration of the final product in solution has been limited to 100 μg/ml.

EXAMPLE 9

E2 Repressor Conjugates

To test cellular uptake and E2 repressor activity of transport polypeptide-E2 repressor conjugates, we simultaneously transfected an E2-dependent reporter plasmid and an E2 expression plasmid into SV40-transformed African green monkey kidney ("COS7") cells. Then we exposed the transfected cells to transport polypeptide-E2 repressor conjugates (made by genetic fusion or chemical cross-linking) or to appropriate controls. The repression assay, described below, was essentially as described in Barsoum et al. (supra).

Repression Assay Cells

We obtained the COS7 cells from the American Type Culture Collection, Rockville, Md. (ATCC No. CRL 1651). We propagated the COS7 cells in Dulbecco's modified Eagle's medium (GIBCO, Grand Island, N.Y.,) with 10% fetal bovine serum (JRH Biosciences, Lenexa, Kans.) and 4 mM glutamine ("growth medium"). Cell incubation conditions were 5.5% $CO_2$ at 37° C.

Repression Assay Plasmids

Our E2-dependent reporter plasmid, pXB332hGH, contained a human growth hormone reporter gene driven by a truncated SV40 early promoter having 3 upstream E2 binding sites. We constructed the hGH reporter plasmid, pXB332hGH, as described in Barsoum et al. (supra).

Figure 10:
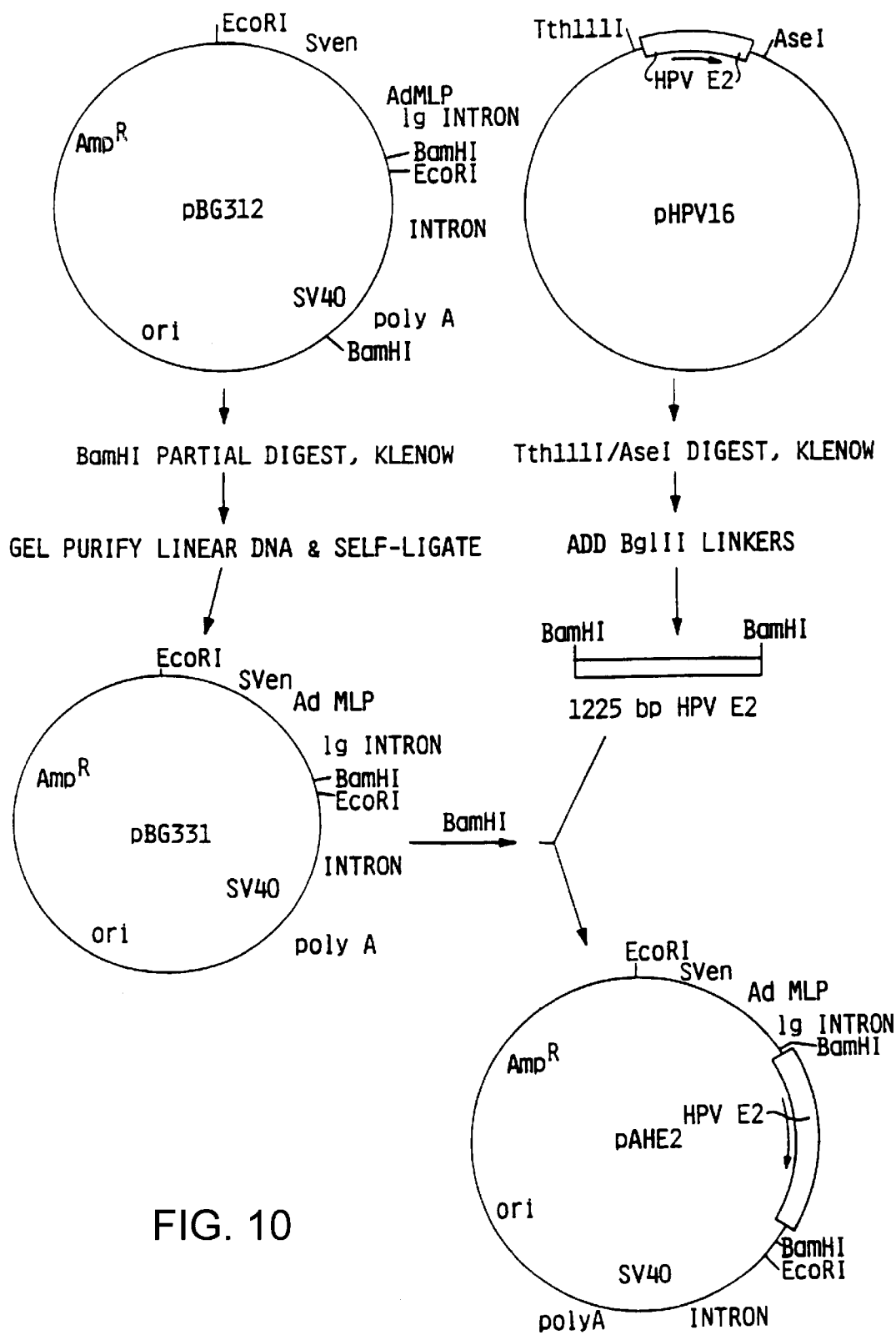
FIG. 10 schematically depicts the construction of plasmid pAHE2.

For expression of a full-length HPV E2 gene, we constructed plasmid pAHE2 (FIG. 10). Plasmid pAHE2 contains the E2 gene from HPV strain 16, operatively linked to the adenovirus major late promoter augmented by the SV40 enhancer, upstream of the promoter. We isolated the HPV E2 gene from plasmid pHPV16 (the full-length HPV16 genome cloned into pBR322), described in M. Durst et al., "A Papillomavirus DNA from Cervical Carcinoma and Its Prevalence in Cancer Biopsy Samples from Different Geographic Regions", *Proc. Natl. Acad. Sci. USA*, 80, pp. 3812–15 (1983), as a Tth111I-AseI fragment. Tth111I cleaves at nucleotLde 2711, and AseI cleaves at nucleotide 3929 in the HPV16 genome. We blunted the ends of the Tth111I-AseI fragment in a DNA polymerase I Klenow reaction, and ligated BamHI linkers (New England Biolabs, cat. No. 1021). We inserted this linker-bearing fragment into BamHI-cleaved plasmid pBG331, to create plasmid pAHE2.

Plasmid pBG331 is the same as pBG312 (R. L. Cate et al., "Isolation of the Bovine and Human Genes for Mullerian Inhibiting Substance and Expression of the Human Gene in Animal Cells", *Cell*, 45, pp. 685–98 (1986)) except that it lacks the BamHI site downstream of the SV40 polyadenylation signal, making the BamHI site between the promoter and the SV40 intron unique. We removed the unwanted BamHI site by partial BamHI digestion of pBG312, gel purification of the linearized plasmid, blunt end formation by DNA polymerase I Klenow treatment, self-ligation and screening for plasmids with the desired deletion of the BamHI site.

Bacterial Production of E2 Repressor Proteins

One of our E2 repressor proteins, E2.123, consisted of the carboxy-terminal 121 amino acids of HPV16 E2 with MetVal added at the amino terminus. We also used a variant of E2.123, called E2.123CCSS. E2.123 has cysteine residues at HPV16 E2 amino acid positions 251, 281, 300 and 309. In E2.123CCSS, the cysteine residues at positions 300 and 309 were changed to serine, and the lysine residue at position 299 was changed to arginine. We replaced the cysteine residues at positions 300 and 309, so that cysteine-dependent chemical cross-linking could take place in the amino terminal portion of the E2 repressor, but not in the E2 minimal DNA binding/dimerization domain. We considered crosslinks in the minimal DNA binding domain likely to interfere with the repressor's biological activity.

Figure 11:
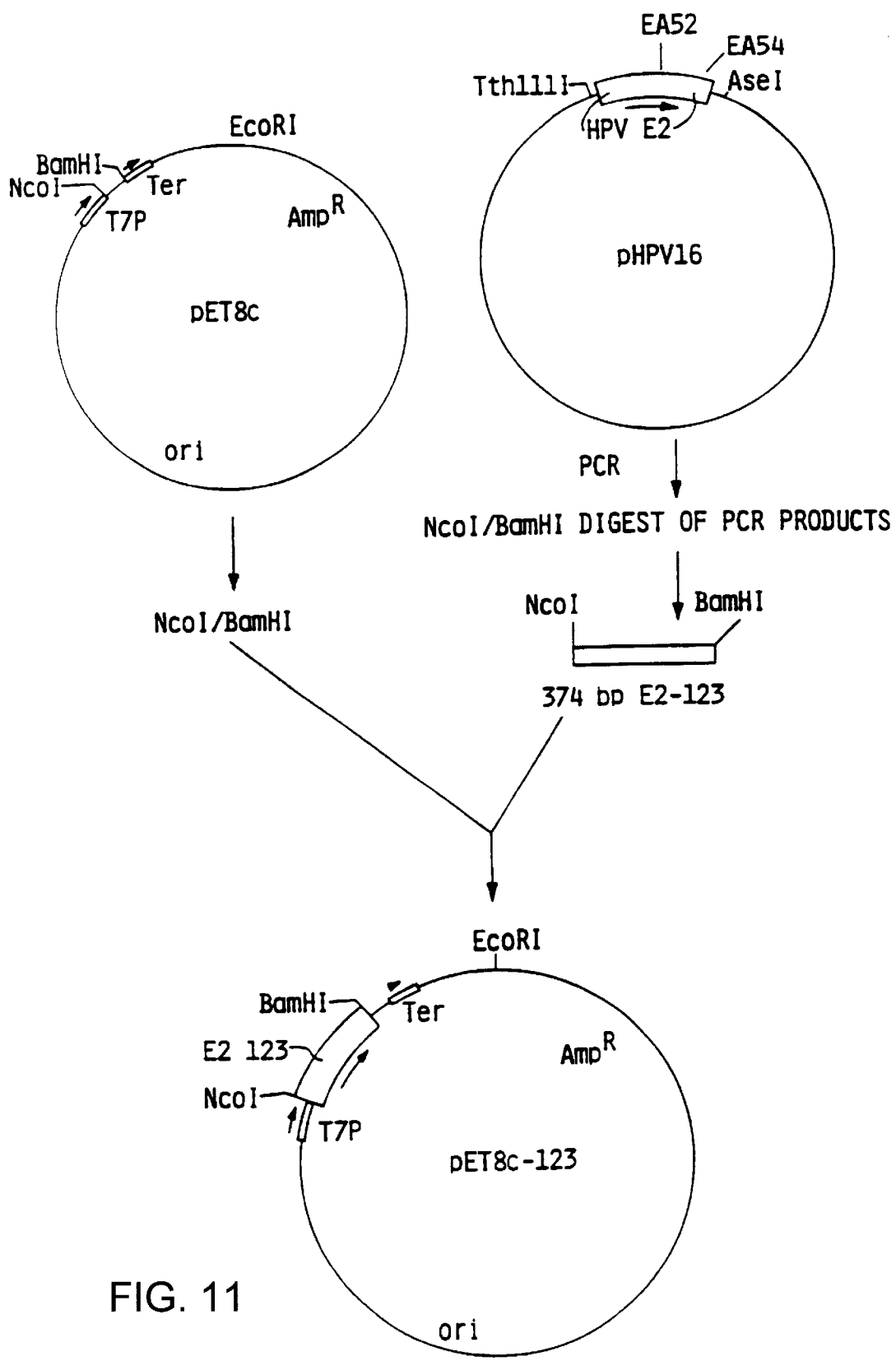
FIG. 11 schematically depicts the construction of plasmid pET8c123.

For construction of plasmid pET8c-123 (FIG. 11; SEQ ID NO:14), we produced the necessary DNA fragment by standard polymerase chain reaction ("PCR") techniques, with plasmid pHPV16 as the template. (For a general discussion of PCR techniques, see Chapter 14 of Sambrook et al., supra. Automated PCR equipment and chemicals are commercially available.) The nucleotide sequence of EA52, the PCR oligonucleotide primer for the 5' end of the 374 base pair E2-123 fragment, is set forth in the Sequence Listing under SEQ ID NO:15. The nucleotide sequence of EA54, the PCR oligonucleotide primer used for the 3' end of the E2-123 fragment is set forth in the Sequence Listing under SEQ ID NO:16. We digested the PCR products with NcoI and BamHI and cloned the resulting fragment into NcoI/BamHI-digested expression plasmid pET8c (Studier et al., supra), to create plasmid pET8c-123.

By using the same procedure with a different 5' oligonucleotide PCR primer, we obtained a 260 base pair fragment ("E2-85") containing a methionine codon and an alanine codon immediately followed by codons for the carboxy-terminal 83 amino acids of HPV16 E2. The nucleotide sequence of EA57, the PCR 5' primer for producing E2-85, is set forth in the Sequence Listing under SEQ ID NO:34.

Figure 12:
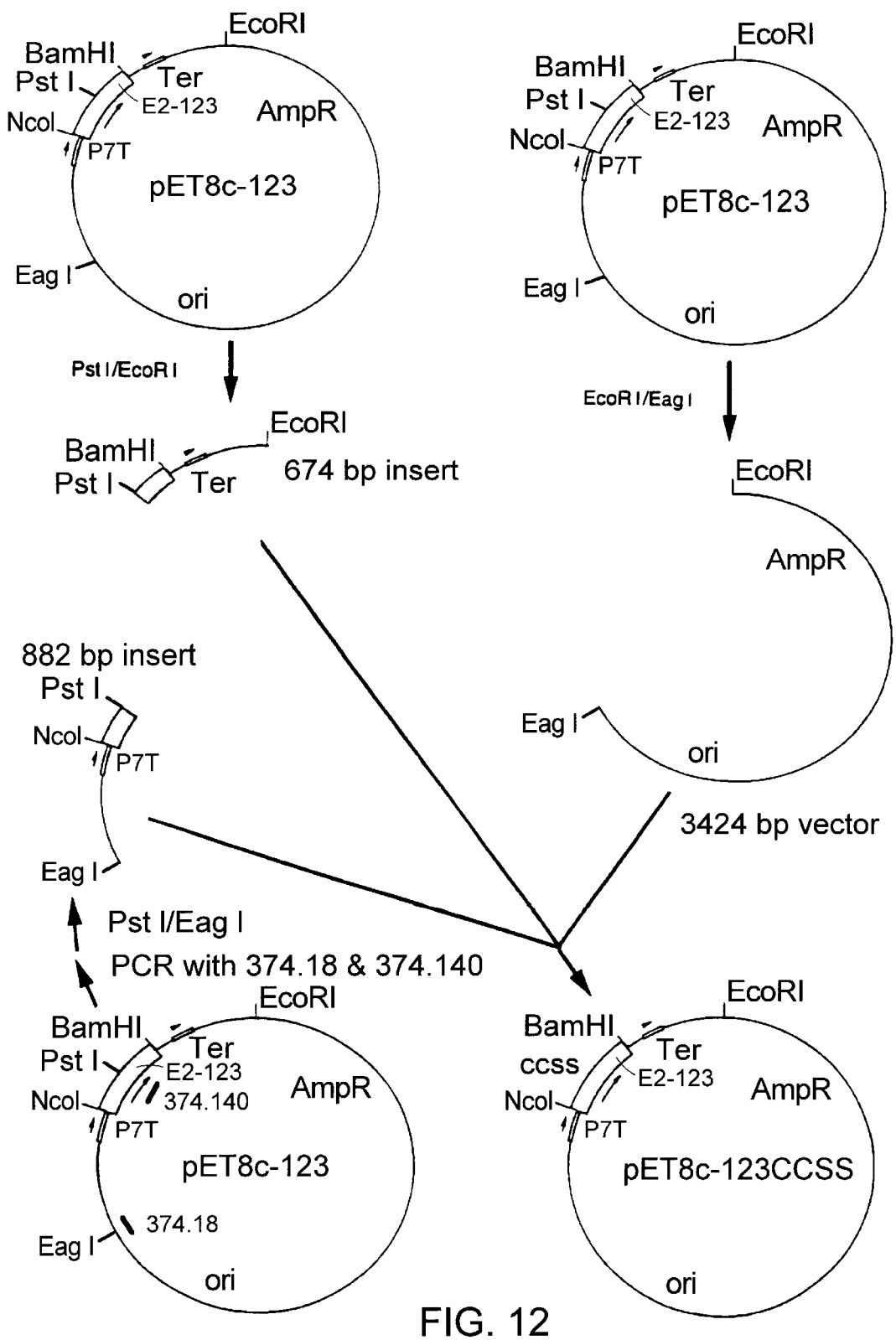
FIG. 12 schematically depicts the construction of plasmid pET8c123CCSS.
Figure 17:
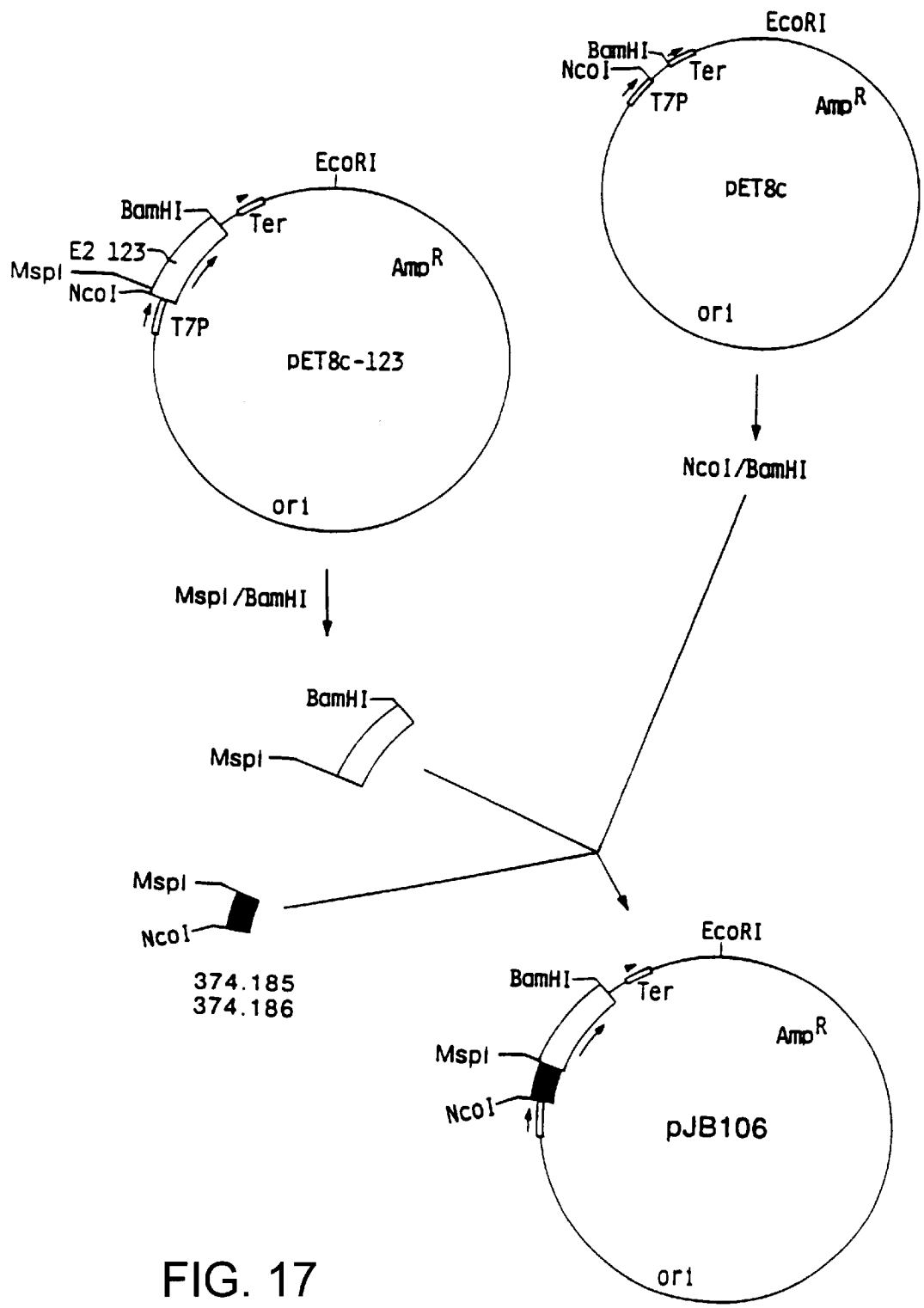
FIG. 17 schematically depicts the construction of plasmid pJB106.

To construct plasmid pET8c-123CCSS (FIG. 12; SEQ ID NO:17), for bacterial production of E2.123CCSS, we synthesized an 882 bp PstI-EagI DNA fragment by PCR techniques. The PCR template was pET8c-123. One of the PCR primers, called 374.140, encoded all three amino acid changes: CGACACTGCA GTATACAATG TAGAATGCTT TTTAAATCTA TATCTTAAAG ATCTTAAAG (SEQ ID NO:18). The other PCR primer, 374.18, had the following sequence: GCGTCGGCCG CCATGCCGGC GATAAT (SEQ ID NO:19). We digested the PCR reaction products with PstI plus EagI and isolated the 882 bp fragment by standard methods. The final step was production of pET8c-123CCSS in a 3-piece ligation joining a 3424 bp EcoRI-EagI fragment from pET8c-123 with the 882 bp PCR fragment and a 674-bp PstI-EcoRI pET8c-123 fragment, as shown in FIG. 17. We verified the construction by DNA sequence analysis. For production of E2.123 and E2.123CCSS proteins, we expressed plasmids pET8c-123 and pET8c-123CCSS in *E.coli* strain BL21(DE3)pLysS, as described by Studier (supra).

Purification of E2 Repressor Proteins

We thawed 3.6 grams of frozen, pET8c-123- transformed *E.coli* cells and suspended them in 35 ml of 25 mM Tris-HCl (pH 7.5), 0.5 mM EDTA, 2.5 mM DTT, plus protease inhibitors (1 mM PMSF, 3 mM benzamidine, 50 µg/ml pepstatin A, 10 µg/ml aprotinin). We lysed the cells by two passages through a French press at 10,000 psi. We centrifuged the lysate at 12,000 rpm, in an SA600 rotor, for 1 hour. The E2.123 protein was in the supernatant. To the supernatant, we added MES buffer (pH 6) up to 25 mM, MES buffer (pH 5) up to 10 mM, and NaCl up to 125 mM. We then applied the supernatant to a 2 ml S Sepharose Fast Flow column at 6 ml/hr. After loading, we washed the column with 50 mM Tris-HCl (pH 7.5), 1 mM DTT. We then carried out step gradient elution (2 ml/step) with 200, 300, 400, 500, 700 and 1000 mM NaCl in 50 mM Tris-HCl (pH 7.5), 1 mM DTT. The E2.123 repressor protein eluted in the 500 and 700 mM NaCl fractions. SDS-PAGE analysis indicated the E2.123 repressor purity exceeded 95%.

We thawed 3.0 grams of frozen, pET8c-123CCSS-ransformed *E.coli* and suspended the cells in 30 ml of the same buffer used for pET8c-123-transformed cells (above). Lysis, removal of insoluble cellular debris and addition of MES buffer and NaCl was also as described for purification of E2–123. The purification procedure for E2.123CCSS diverged after addition of the MES buffer and NaCl, because a precipitate formed, with E2.123CCSS, at that point in the procedure. We removed the precipitate by centrifugation, and found that it and the supernatant both contained substantial E2 repressor activity. Therefore, we subjected both to purification steps. We applied the supernatant to a 2 ml S Sepharose Fast Flow column (Pharmacia LKB, Piscataway, N.J.) at 6 ml/hr. After loading, we washed the column with 50 mM Tris-HCl (pH 7.5), 1 mM DTT. After washing the column, we carried out step gradient elution (2 ml/step), using 300, 400, 500, 700 and 1000 mM NaCl in 50 mM Tris-HCl (pH 7.5), 1 mM DTT. The E2.123CCSS protein eluted with 700 mM NaCl. SDS-PAGE analysis indicated its purity to exceed 95%. We dissolved the E2.123CCSS precipitate in 7.5 ml of 25 mM Tris-HCl (pH 7.5), 125 mM NaCl, 1 mM DTT and 0.5 mM EDTA. We loaded the dissolved material onto a 2 ml S Sepharose Fast Flow column and washed the column as described for E2.123 and non-precipitated E2.123CCSS. We carried out step gradient elution (2 ml/step), using 300, 500, 700 and 1000 mM NaCl. The E2 repressor eluted in the 500–700 mM NaCl fractions. SDS-PAGE analysis indicated its purity to exceed 98%. Immediately following purification of the E2.123 and E2.123CCSS proteins, we added glycerol to a final concentration of 15% (v/v), and stored flash-frozen (liquid $N_2$) aliquots at −70° C. We quantified the purified E2 repressor proteins by UV absorbance at 280 nm, using an extinction coefficient of 1.8 at 1 mg/ml.

Chemical Cross-Linking

We performed chemical synthesis of the transport polypeptide consisting of tat amino acids 37–72, as described in Example 1. We dissolved the polypeptide (5 mg/ml) in 10 mM MES buffer (pH 5.0), 50 mM NaCl, 0.5 mM EDTA, (extinction coefficient of 0.2 at 1 ml/ml). To the transport polypeptide solution, we added a bismaleimidohexane ("BMH") (Pierce Chemical Co., Rockford, Ill., cat. No. 22319G) stock solution (6.25 mg/ml DMF) to a final concentration of 1.25 mg/ml, and a pH 7.5 HEPES buffer stock solution (1 M) to a final concentration of 100 mM. We allowed the BMH to react with the protein for 30 minutes at room temperature. We then separated the protein-BMH from unreacted BMH by gel filtration on a G-10 column equilibrated in 10 mM MES (pH 5), 50 mM NaCl, 0.5 mM EDTA. We stored aliquots of the transport polypeptide-BMH conjugate at −70° C.

For cross-linking of the transport polypeptide-BMH conjugate to the E2 repressor, we removed the E2 repressor protein from its storage buffer. We diluted the E2 repressor protein with three volumes of 25 mM MES (pH 6.0), 0.5 mM EDTA and batch-loaded it onto S Sepharose Fast Flow (Pharmacia LKB, Piscataway, N.J.) at 5 mg protein per ml resin. After pouring the slurry of protein-loaded resin into a column, we washed the column with 25 mM MES (pH 6.0), 0.5 mM EDTA, 250 mM NaCl. We then eluted the bound E2 repressor protein from the column with the same buffer containing 800 mM NaCl. We diluted the E2 repressor-containing eluate to 1 mg/ml with 25 mM MES (pH 6.0), 0.5 mM EDTA. From trial cross-linking studies performed with each batch of E2 repressor protein and BMH-activated transport polypeptide, we determined that treating 1 mg of E2 repressor protein with 0.6 mg of BMH-activated transport polypeptide yields the desired incorporation of 1 transport molecule per E2 repressor homodimer. Typically, we mixed 2 ml of E2 repressor (1 mg/ml) with 300 μl of tat37-72-BMH (4 mg/ml) and 200 μl of 1 M HEPES (pH 7.5). We allowed the cross-linking reaction to proceed for 30 minutes at room temperature. We terminated the cross-linking reaction by adding 2-mercaptoethanol to a final concentration of 14 mM. We determined the extent of cross-linking by SDS-PAGE analysis. We stored aliquots of the tat37-72-E2 repressor conjugate at −70° C. We employed identical procedures to chemically cross-link the tat37-72 transport polypeptide to the HPVE2 123 repressor protein and the HPVE2 CCSS repressor protein.

Cellular Uptake of E2 Repressor Conjugates

For our E2 repression assays, we used transient expression of plasmids transfected into COS7 cells. Our E2 repression assay procedure was similar to that described in Barsoum et al. (supra). We transfected $4 \times 10^6$ COS7 cells (about 50% confluent at the time of harvest) by electroporation, in two separate transfections ("EP1" and "EP2"). In transfection EP1, we used 20 μg pXB332hGH (reporter plasmid) plus 380 μg sonicated salmon sperm carrier DNA (Pharmacia LKB, Piscataway, N.J.). In transfection EP2, we used 20 μg pXB332hGH plus 30 μg pAHE2 (E2 transactivator) and 350 μg salmon sperm carrier DNA. We carried out electroporations with a Bio-Rad Gene Pulser, at 270 volts, 960 μFD, with a pulse time of about 11 msec. Following the electroporations, we seeded the cells in 6-well dishes, at $2 \times 10^5$ cells per well. Five hours after the electroporations, we aspirated the growth medium, rinsed the cells with growth medium and added 1.5 ml of fresh growth medium to each well. At this time, we added chloroquine ("CQ") to a final concentration of 80 μM (or a blank solution to controls). Then we added tat37-72 cross-linked E2.123 ("TxHE2") or tat37-72 cross-linked to E2.123CCSS ("TxHE2CCSS"). The final concentration of these transport polypeptide-cargo conjugates was 6, 20 or 60 μg/ml of cell growth medium (Table I).

TABLE I

Identification of Samples

| well | CQ (μM) | protein (μg/ml) |
|------|---------|-----------------|
| EP1.1 | 0 | 0 |
| EP1.2 | 80 | 0 |
| EP2.1 | 0 | 0 |
| EP2.2 | 0 | 6 TxHE2 |
| EP2.3 | 0 | 20 TxHE2 |
| EP2.4 | 0 | 60 TxHE2 |
| EP2.5 | 0 | 6 TxHE2CCSS |
| EP2.6 | 0 | 20 TxHE2CCSS |
| EP2.7 | 0 | 60 TxHE2CCSS |
| EP2.8 | 80 | 0 |
| EP2.9 | 80 | 6 TxHE2 |
| EP2.10 | 80 | 20 TxHE2 |
| EP2.11 | 80 | 60 TxHE2 |
| EP2.12 | 80 | 6 TxHE2CCSS |
| EP2.13 | 80 | 20 TxHE2CCSS |
| EP2.14 | 80 | 60 TxHE2CCSS |

After an 18-hour incubation, we removed the medium, rinsed the cells with fresh medium, and added 1.5 ml of fresh medium containing the same concentrations of chloroquine and transport polypeptide-cargo conjugates as in the preceding 18-hour incubation. This medium change was to remove any hGH that may have been present before the repressor entered the cells. Twenty-four hours after the medium change, we harvested the cells and performed cell counts to check for viability. We then assayed for hGH on undiluted samples of growth medium according to the method of Seldon, described in *Protocols in Molecular Biology*, Green Publishing Associates, New York, pp. 9.7.1–9.7.2 (1987), using the Allegro Human Growth Hormone transient gene expression system kit (Nichols Institute, San Juan Capistrano, Calif.). We subtracted the assay background (i.e., assay components with non-conditioned medium added) from the hGH cpm, for all samples. We performed separate percentage repression calculations for a given protein treatment, according to whether chloroquine was present ("(+)CQ") or absent ("(−)CQ") in the protein uptake test. We calculated percentage repression according to the following formula:

$$\text{Repression} = \frac{(\text{ACT} - \text{BKG}) - (\text{REP} - \text{BKG})}{\text{ACT} - \text{BKG}}$$

where:  BKG = hGH cpm in the transfections of reporter alone (e.g., EP1.1 for (−)CQ and EP1.2 for (+)CQ);
ACT = hGH cpm in the transfection of reporter plus transactivator, but to which no repressor conjugate was added (e.g., EP2.1 for (−)CQ and EP2.8 for (+)CQ);
REP = hGH cpm in the transfection of reporter plus transactivator, to which a repressor conjugate was added (e.g., EP2.2–2.7 for (−)CQ and EP2.9–2.14 for (+)CQ).

Figure 13:
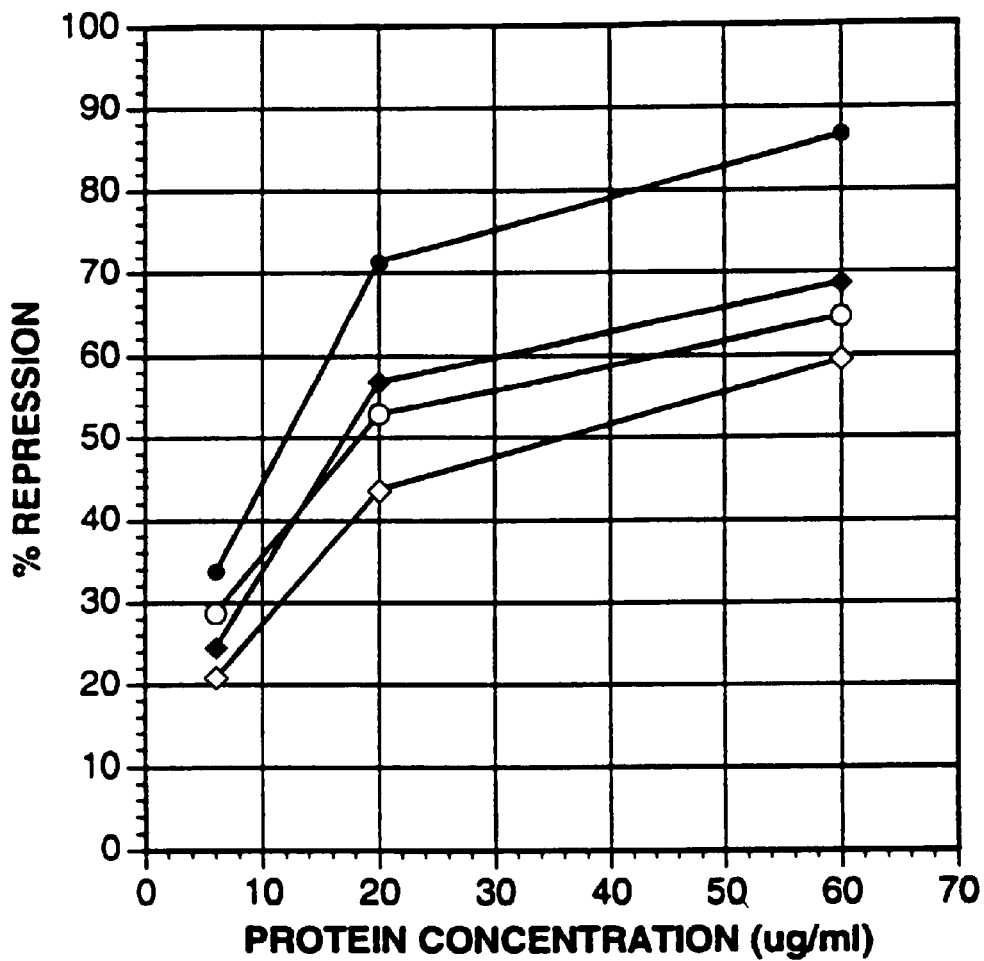
FIG. 13 summarizes the results of cellular uptake experiments with transport polypeptide-E2 repressor conjugates (open diamonds, E2.123 cross-linked to tat37-72, without chloroquine; closed diamonds, E2.123 cross-linked to tat37-72, with chloroquine; open circles, E2.123CCSS cross-linked to tat37-72, without chloroquine; closed circles, E2.123CCSS cross-linked to tat37-72, with chloroquine).

Data from a representative E2 repression assay are shown in Table II. Table I identifies the various samples represented in Table II. FIG. 13 graphically depicts the results presented in Table II.

TABLE II

E2 Repression Assay

| sample | hGH cpm | cpm-assay bkgd | cpm-BKG | % repression |
|---|---|---|---|---|
| EP1.1 | 3958 | 3808 | — | — |
| EP1.2 | 5401 | 5251 | — | — |
| EP2.1 | 15,161 | 15,011 | 11,203 | — |
| EP2.2 | 12,821 | 12,671 | 8863 | 20.9 |
| EP2.3 | 10,268 | 10,118 | 6310 | 43.7 |
| EP2.4 | 8496 | 8346 | 4538 | 59.5 |
| EP2.5 | 11,934 | 11,784 | 7976 | 28.8 |
| EP2.6 | 9240 | 9090 | 5282 | 52.9 |
| EP2.7 | 7926 | 7776 | 3968 | 64.6 |
| EP2.8 | 15,120 | 14,970 | 9719 | — |
| EP2.9 | 12,729 | 12,579 | 7328 | 24.6 |
| EP2.10 | 9590 | 9440 | 4189 | 56.9 |
| EP2.11 | 8440 | 8290 | 3039 | 68.7 |
| EP2.12 | 11,845 | 11,695 | 6444 | 33.7 |
| EP2.13 | 8175 | 8025 | 2774 | 71.5 |
| EP2.14 | 6697 | 6547 | 1296 | 86.7 |

Transport polypeptide tat37-72 cross-linked to either E2 repressor (E2.123 or E2.123CCSS) resulted in a dose-dependent inhibition of E2-dependent gene expression in the cultured mammalian cells (Table II; FIG. 13). We have repeated this experiment four times, with similar results. The effect was E2-specific, in that other tat37-72 conjugates had no effect on E2 induction of pXB332hGH (data not shown). Also, the tat37-72xHE2 conjugates had no effect on the hGH expression level of a reporter in which the expression of the hGH gene was driven by a constitutive promoter which did not respond to E2. The E2 repressor with the CCSS mutation repressed to a greater degree than the repressor with the wild-type amino acid sequence. This was as expected, because cross-linking of the transport polypeptide to either of the last two cysteines in the wild-type repressor would likely reduce or eliminate repressor activity. Chloroquine was not required for the repression activity. However, chloroquine did enhance repression in all of the tests. These results are summarized in Table II and FIG. 13.

EXAMPLE 10

TATΔCYS Conjugates

Production of TatΔcys

Figure 14:
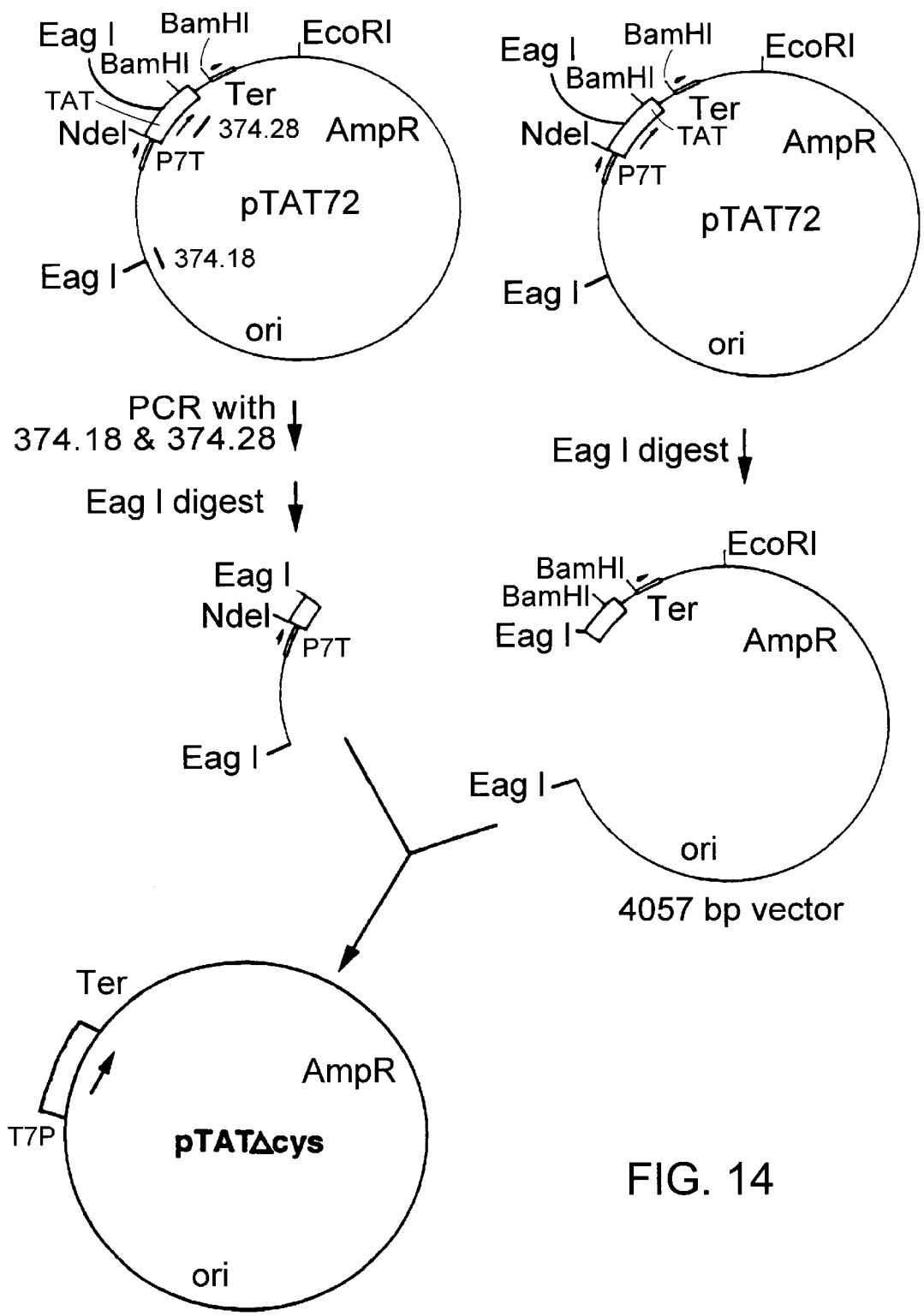
FIG. 14 schematically depicts the construction of plasmid pTATΔcys.

For bacterial production of a transport polypeptide consisting of tat amino acids 1–21 fused directly to tat amino acids 38–72, we constructed expression plasmid pTATAcys (FIG. 14; SEQ ID NO:20). To construct plasmid pTATAcys, we used conventional PCR techniques, with plasmid pTAT72 as the PCR template. One of the oligonucleotide primers used for the PCR was 374.18 (SEQ ID NO:19), which covers the EagI site upstream of the tat coding sequence. (We also used oligonucleotide 374.18 in the construction of plasmid pET8c-123CCSS. See Example 9.) The other oligonucleotide primer for the PCR, 374.28, covers the EagI site within the tat coding sequence and has a deletion of the tat DNA sequence encoding amino acids 22–37. The nucleotide sequence of 374.28 is: TTTACG-GCCG TAAGAGATAC CTAGGGCTTT GGTGATGAAC GCGGT (SEQ ID NO:21). We digested the PCR products with EagI and isolated the resulting 762-base pair fragment. We inserted that EagI fragment into the 4057 base pair vector produced by EagI cleavage of pTAT72. We verified the construction by DNA sequence analysis and expressed the tatΔcys polypeptide by the method of Studier et al. (supra). SDS-PAGE analysis showed the tatΔcys polypeptide to have the correct size.

For purification of tatAcys protein, we thawed 4.5 grams of pTATΔcys-transformed *E.coli* cells, resuspended the cells in 35 ml of 20 mM MES (pH 6.2), 0.5 mM EDTA. We lysed the cells by two passes through a French press, at 10,000 psi. We removed insoluble debris by centrifugation at 10,000 rpm in an SA600 rotor, for 1 hour. We applied the supernatant to a 5 ml S Sepharose Fast Flow column at 15 ml/hr. We washed the column with 50 mM Tris-HCl (pH 7.5), 0.3 mM DTT. We then carried out step gradient elution (2 ml/step) with the same buffer containing 300, 400, 500, 700 and 950 mM NaCl. The tatΔcys protein eluted in the 950 mM NaCl fraction.

We conjugated a tatΔcys transport polypeptide to rhodamine isothiocyanate and tested it by assaying directly for cellular uptake. The results were positive (similar to results in related experiments with tat1-72).

TATΔcys-249 Genetic Fusion

Figure 15:
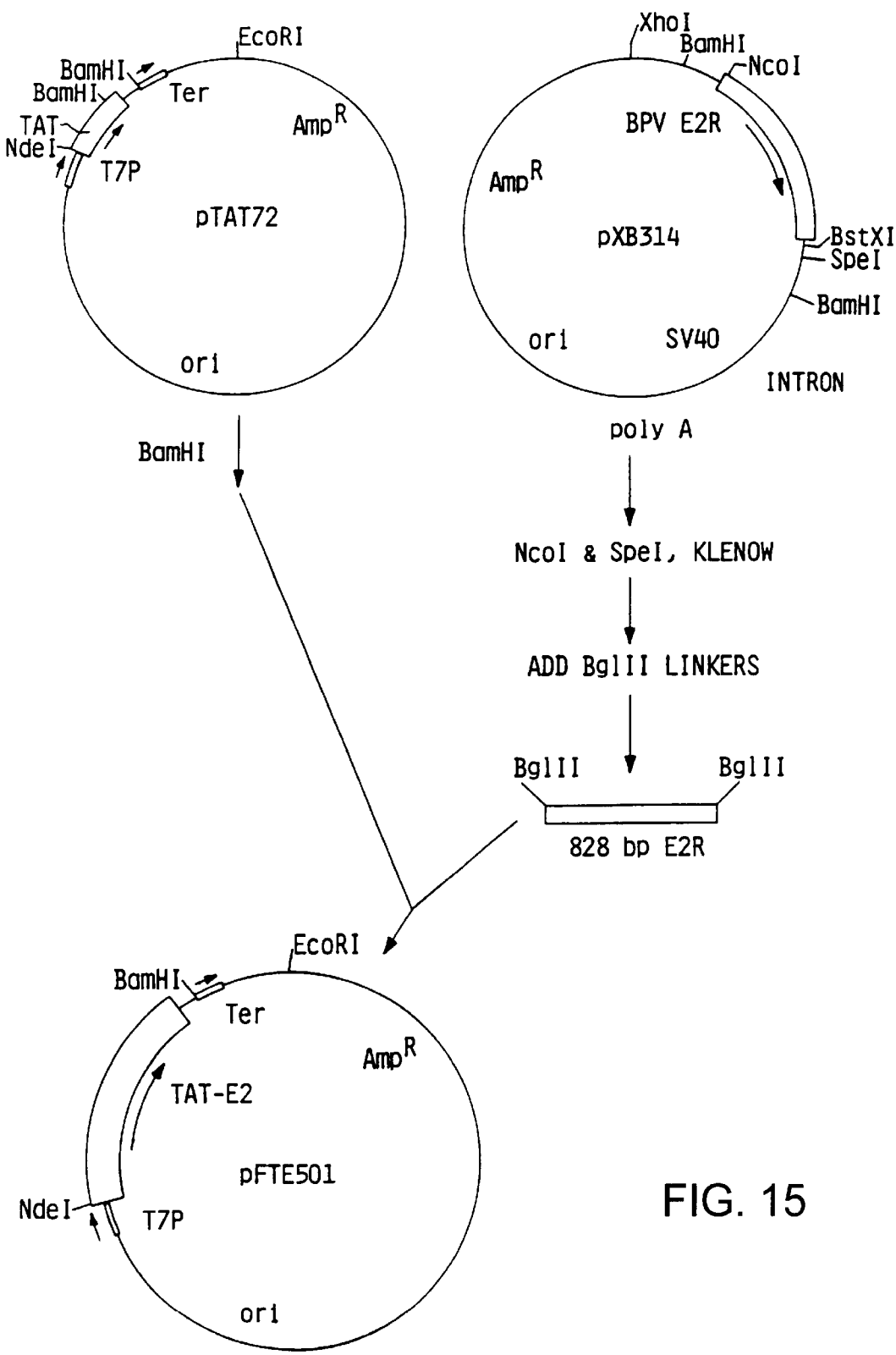
FIG. 15 schematically depicts the construction of plasmid pFTE501.
Figure 16:
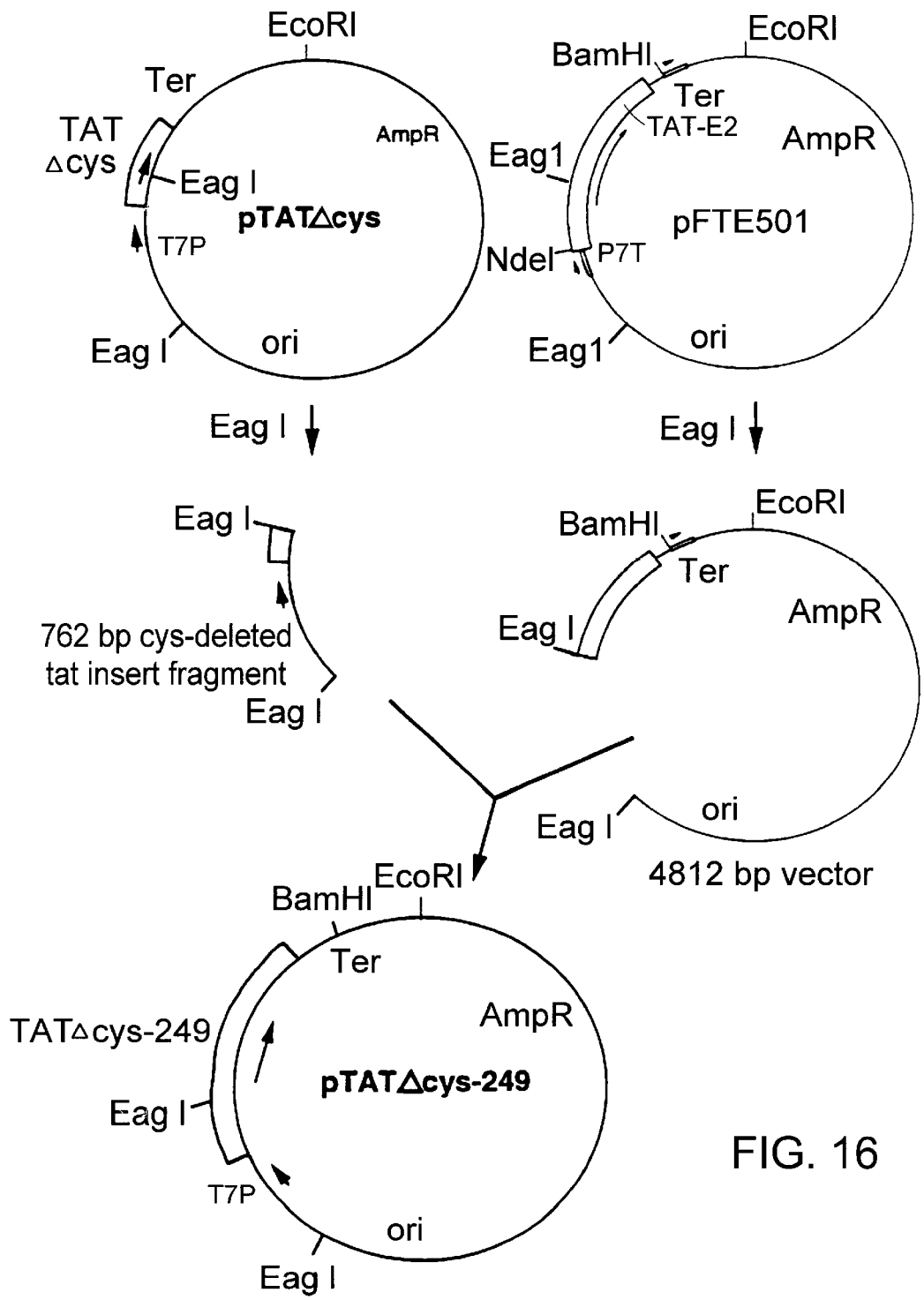
FIG. 16 schematically depicts the construction of plasmid pTATΔcys-249.

For bacterial expression of the tatΔcys transport polypeptide genetically fused to the amino terminus of the native E2 repressor protein (i.e., the carboxy-terminal 249 amino acids of BPV-1 E2), we constructed plasmid pTATΔcys-249 as follows. We constructed plasmid pFTE501 (FIG. 15) from plasmids pTAT72 (Frankel and Pabo, supra and Example I) and pXB314 (Barsoum et al., supra). From plasmid pXB314, we isolated the NcoI-SpeI DNA fragment encoding the 249 amino acid BPV-1 E2 repressor. (NcoI cleaves at nucleotide 296, and SpeI cleaves at nucleotide 1118 of pXB314.) We blunted the ends of this fragment by DNA polymerase I Klenow treatment and added a commercially available BglII linker (New England Biolabs, cat. No. 1090). We inserted this linker-bearing fragment into BamHI-cleaved (complete digestion) plasmid pTAT72. In pTAT72, there is a BamHI cleavage site within the tat coding region, near its 3′ end, and a second BamHI cleavage site slightly downstream of the tat gene. The BglII linker joined the tat and E2 coding sequences in frame to encode a fusion of the first 62 amino acids of tat protein followed by a serine residue and the last 249 amino acids of BPV-1 E2 protein. We designated this bacterial expression plasmid pFTE501 (FIG. 15). To construct plasmid pTATΔcys-249 (FIG. 16; SEQ ID NO:22), we inserted the 762 base pair EagI fragment from plasmid PTAT cys, which includes the portion of tat containing the cysteine deletion, into the 4812 base pair EagI fragment of plasmid pFTE501.

Purification of tatΔcys-249

We thawed 5 g of *E.coli* expressing tatΔcys-249 and suspended the cells in 40 ml of 25 mM Tris HCl (pH 7.5), 25 mM NaCl, 0.5 mM EDTA, 5 mM DTT, plus protease inhibitors (1.25 mM PMSF, 3 mM Benzamidine, 50 μg/ml pepstatin A, 50 μg/ml aprotinin, 4 μg/ml E64). We lysed the cells by two passages through a French pressure cell at 10,000 psi. We removed insoluble debris from the lysate by centrifugation at 12,000 rpm in an SA600 rotor, for 1 hour. We purified the tatΔcys-249 from the soluble fraction. The supernatant was loaded onto a 2 ml S Sepharose Fast Flow column (Pharmacia LKB, Piscataway, N.J.) at a flow rate of 6 ml/h. The column was washed with 25 mM Tris HCl pH (7.5), 25 mM NaCl, 0.5 mM EDTA, 1 mM DTT and treated with sequential salt steps in the same buffer containing 100, 200, 300, 400, 500, 600, and 800 mM NaCl. We recovered the TatΔcys-249 in the 600–800 mM salt fractions. We pooled the peak fractions, added glycerol to 15%, and stored aliquots at −70° C.

Immunofluorescence Assay

To analyze cellular uptake of the tatΔcys-E2 repressor fusion protein, we used indirect immunofluorescence techniques. We seeded HeLa cells onto cover slips in 6-well tissue culture dishes, to 50% confluence. After an overnight incubation, we added the tatΔcys-E2 repressor fusion protein (1 μg/ml final concentration) and chloroquine (0.1 mM final concentration). After six hours, we removed the fusion protein/chloroquine-containing growth medium and washed the cells twice with PBS. We fixed the washed cells in 3.5% formaldehyde at room temperature. We permeabilized the fixed cells with 0.2% Triton X-100/2% bovine serum albumin ("BSA") in PBS containing 1 mM $MgCl_2$/0.1 mM $CaCl_2$ ("PBS+") for 5 minutes at room temperature. To block the permeabilized cells, we treated them with PBS containing 2% BSA, for 1 hour at 4° C.

We incubated the cover slips with 20 μl of a primary antibody solution in each well, at a 1:100 dilution in PBS+ containing 2% BSA, for 1 hour at 4° C. The primary antibody was either a rabbit polyclonal antibody to the BPV-1 E2 repressor (generated by injecting the purified carboxy-terminal 85 amino acids of E2), or a rabbit polyclonal antibody to tat (generated by injecting the purified amino-terminal 72 amino acids of tat protein). We added a secondary antibody at a 1:100 dilution in 0.2% Tween-20/2% BSA in PBS+ for 30 minutes at 4° C.

The secondary antibody was a rhodamine-conjugated goat anti-rabbit IgG (Cappel No. 2212-0081). Following incubation of the cells with the secondary antibody, we washed the cells with 0.2% Tween 20/2% BSA in PBS+ and mounted the cover slips in 90% glycerol, 25 mM sodium phosphate (pH 7.2), 150 mM NaCl. We examined the cells with a fluorescent microscope having a rhodamine filter.

Cellular Uptake of TatΔCys Fusions

We observed significant cellular uptake of the tatΔcys-E2 repressor fusion protein, using either the tat antibody or the E2 antibody. In control cells exposed to the unconjugated tat protein, we observed intracellular fluorescence using the tat antibody, but not the E2 antibody. In control cells exposed to a mixture of the unconjugated E2 repressor and tat protein or tatΔcys, we observed fluorescence using the tat antibody, but not the E2 antibody. This verified that tat mediates E2 repressor uptake only when linked to the tat protein. As with unconjugated tat protein, we observed the tatΔcys-E2 repressor fusion protein throughout the cells, but it was concentrated in intracellular vesicles. These results show that a tat-derived polypeptide completely lacking cysteine residues can carry a heterologous protein (i.e., transport polypeptide-cargo protein genetic fusion) into animal cells.

In a procedure similar to that described above, we produced a genetic fusion of tatΔcys to the C-terminal 123 amino acids of HPV E2. When added to the growth medium, this fusion polypeptide exhibited repression of E2-dependent gene expression in COS7 cells (data not shown).

EXAMPLE 11

Antisense Oligodeoxynucleotide Conjugates

Using an automated DNA/RNA synthesizer (Applied Biosystems model 394), we synthesized DNA phosphorothionate analogs (4–18 nucleotides in length), with each containing a free amino group at the 5' end. The amine group was incorporated into the oligonucleotides using commercially modified nucleotides (aminolink 2, Applied Biosystems). The oligonucleotides corresponded to sense and antisense strands from regions of human growth hormone and CAT messenger RNA.

For each cross-linking reaction, we dissolved 200 μg of an oligonucleotide in 100 μl of 25 mM sodium phosphate buffer (pH 7.0). We then added 10 μl of a 50 mM stock solution of sulfo-SMCC and allowed the reaction to proceed at room temperature for 1 hour. We removed unreacted sulfo-SMCC by gel filtration of the reaction mixture on a P6DG column (Bio-Rad) in 25 mM HEPES (pH 6.0). We dried the oligonucleotide-sulfo-SMCC adduct under a vacuum. Recovery of the oligonucleotides in this procedure ranged from 58 to 95%. For reaction with a transport polypeptide, we redissolved each oligonucleotide-sulfo-SMCC adduct in 50 μl of 0.5 mM EDTA, transferred the solution to a test tube containing 50 μg of lyophilized transport polypeptide, and allowed the reaction to proceed at room temperature for 2 hours. We analyzed the reaction products by SDS-PAGE.

EXAMPLE 12

Antibody Conjugates

Anti-Tubulin Conjugate 1

We obtained commercial mouse IgG1 mAb anti-tubulin (Amersham) and purified it from ascites by conventional methods, using protein A. We labelled the purified antibody with rhodamine isothiocyanate, at 1.2 moles rhodamine/mole Ab. When we exposed fixed, permeabilized HeLa cells to the labelled antibody, microscopic examination revealed brightly stained microtubules. Although the rhodamine labelling was sufficient, we enhanced the antibody signal with anti-mouse FITC.

In a procedure essentially as described in Example 2, (above) we allowed 250 μg of the antibody to react with a 10:1 molar excess of sulfo-SMCC. We then added 48 μg of ($^{35}$S-labelled) tat1-72. The molar ratio of tat1-71: Ab was 2.7:1. According to incorporation of radioactivity, the tat1:72 was cross-linked to the antibody in a ratio of 0.6:1.

For analysis of uptake of the tat1-72-Ab conjugate, we added the conjugate to medium (10 μg/ml) bathing cells grown on coverslips. We observed a punctate pattern of fluorescence in the cell. The punctate pattern indicated vesicular location of the conjugate, and was therefore inconclusive as to cytoplasmic delivery.

To demonstrate immunoreactivity of the conjugated antibody, we tested its ability to bind tubulin. We coupled purified tubulin to cyanogen bromide-activated Sepharose 4B (Sigma Chem. Co., St. Louis, Mo.). We applied a samples of the radioactive conjugate to the tubulin column (and to a Sepharose 4B control column) and measured the amount of bound conjugate. More radioactivity bound to the affinity matrix than to the control column, indicating tubulin binding activity.

Anti-Tubulin Conjugate 2

In a separate cross-linking experiment, we obtained an anti-tubulin rat monoclonal antibody IgG2a (Serotec), and purified it from ascites by conventional procedures, using protein G. We eluted the antibody with Caps buffer (pH 10). The purified antibody was positive in a tubulin-binding assay. We allowed tat1-72 to react with rhodamine isothiocyanate at a molar ratio of 1:1. The reaction product exhibited an $A_{555}/A_{280}$ ratio of 0.63, which indicated a substitution of approximately 0.75 mole of dye per mole of tat1-72. Upon separation of the unreacted dye from the tat1-72-rhodamine, by G-25 gel filtration (Pharmacia LKB, Piscataway, N.J.), we recovered only 52 µg out of 150 µg of tat1-72 used in the reaction.

We saved an aliquot of the tat1-72-rhodamine for use (as a control) in cellular uptake experiments, and added the rest to 0.4 mg of antibody that had reacted with SMCC (20:1). The reaction mixture contained a tat1-72: Ab ratio of approximately 1:1, rather than the intended 5:1. (In a subsequent experiment, the 5:1 ratio turned out to be unsatisfactory, yielding a precipitate.) We allowed the cross-linking reaction to proceed overnight at 4° C. We then added a molar excess of cysteine to block the remaining maleimide groups and thus stop the cross-linking reaction. We centrifuged the reaction mixtures to remove any precipitate present.

We carried out electrophoresis using a 4–20% polyacrylamide gradient gel to analyze the supernatant under reducing and non-reducing conditions. We also analyzed the pellets by this procedure. In supernatants from antibody-tat1-72 (without rhodamine) conjugation experiments, we observed very little material on the 4–20% gel. However, in supernatants from the antibody-tat1-72-rhodamine conjugation experiments, we observed relatively heavy bands above the antibody, for the reduced sample. The antibody appeared to be conjugated to the tat1-72 in a ratio of approximately 1:1.

In cellular uptake experiments carried out with conjugate 2 (procedure as described above for conjugate 1), we obtained results similar to those obtained with conjugate 1. When visualizing the conjugate by rhodamine fluorescence or by fluorescein associated with a second antibody, we observed the conjugate in vesicles.

EXAMPLE 13

Additional Tat-E2 Conjugates

Chemically Cross-Linked Tat-E2 Conjugates

We chemically cross-linked transport polypeptide tat37-72 to four different repressor forms of E2. The four E2 repressor moieties used in these experiments were the carboxy-terminal 103 residues (i.e., 308–410) of BPV-1 ("E2.103"); the carboxy-terminal 249 residues (i.e., 162-410) of BPV-1 ("E2.249"); the carboxy-terminal 121 residues (i.e., 245-365) of HPV-16 ("HE2"); and the carboxy-terminal 121 residues of HPV-16, in which the cysteine residues at positions 300 and 309 were changed to serine, and the lysine residue at position 299 was changed to arginine ("HE2CCSS"). The recombinant production and purification of HE2 and HE2CCSS, followed by chemical cross-linking of HE2 and HE2CCSS to tat37-72, to form TxHE2 and TxHE2CCSS, respectively, are described in Example 9 (above). For the chemical cross-linking of E2.103 and E2.249 to tat37-72 (to yield the conjugates designated TxE2.103 and TxE2.249), we employed the same method used to make TxHE2 and TxHE2CCSS (Example 9, supra).

We expressed the protein E2.103 in *E.coli* from plasmid pET-E2.103. We obtained pET-E2.103 by a PCR cloning procedure analogous to that used to produce pET8c-123, described in Example 9 (above) and FIG. 11. As in the construction of pET8c-123, we ligated a PCR-produced NcoI-BamHI E2 fragment into NcoI-BamHI-cleaved pET8c. Our PCR template for the E2 fragment was plasmid pCO-E2 (Hawley-Nelson et al., *EMBO J.*, vol 7, pp. 525–31 (1988); U.S. Pat. No. 5,219,990). The oligonucleotide primers used to produce the E2 fragment from pCO-E2 were EA21 (SEQ ID NO:36) and EA22 (SEQ ID NO:37). Primer EA21 introduced an NcoI site that added a methionine codon followed by an alanine codon 5' adjacent to the coding region for the carboxy-terminal 101 residues of BPV-1 E2.

We expressed the protein E2.249 in *E.coli* from plasmid pET8c-249. We constructed pET8c-249 by inserting the 1362 bp NcoI-BamHI fragment of plasmid pXB314 (FIG. 15) into NcoI-BamHI-cleaved pET8c (FIG. 11).

TATΔcys-BPV E2 Genetic Fusions

In addition to TATΔcys-249, we tested several other TATΔcys-BPV-1 E2 repressor fusions. Plasmid pTATΔcys-105 encoded tat residues 1–21 and 38–67, followed by the carboxy-terminal 105 residues of BPV-1. Plasmid pTATΔcys-161 encoded tat residues 1–21 and 38–62, followed by the carboxy-terminal 161 residues of BPV-1. We constructed plasmids pTATΔcys-105 and pTATΔcys-161 from intermediate plasmids pFTE103 and pFTE403, respectively.

We produced pFTE103 and pFTE403 (as well as pFTE501) by ligating different inserts into BamHI-cleaved (complete digestion) vector pTAT72.

To obtain the insertion fragment for pFTE103, we isolated a 929 base pair PleI-BamHI fragment from pXB314 and ligated it to a double-stranded linker consisting of synthetic oligonucleotide FTE.3 (SEQ ID NO:23) and synthetic oligonucleotide FTE.4 (SEQ ID NO:24). The linker encoded tat residues 61–67 and had a BamHI overhang at the 5' end and a PleI overhang at the 3' end. We ligated the linker-bearing fragment from pXB3314 into BamHI-cleaved pTAT72, to obtain pFTE103. To obtain the insertion fragment for pFTE403, we digested pXB314 with NcoI and SpeI, generated blunt ends with Klenow treatment and ligated a BglII linker consisting of GAAGATCTTC (New England Biolabs, Beverly, Mass., Cat. No. 1090) (SEQ ID NO:35) duplexed with itself. We purified the resulting 822-base pair fragment by electrophoresis and then ligated it into BamHI-digested pTAT72 vector, to obtain pFTE403.

To delete tat residues 22–37, thereby obtaining plasmid pTATΔcys-105 from pFTE103 and pTATΔcys-161 from pFTE403, we employed the same method (described above) used to obtain plasmid pTATΔcys-249 from pFTE501.

TATΔcys-HPV E2 Genetic Fusions

We constructed plasmids pTATΔcys-HE2.85 and pTATΔcys-HE2.121 to encode a fusion protein consisting of the tatΔcys transport moiety (tat residues 1–21, 38–72) followed by the carboxy-terminal 85 or 121 residues of HPV-16, respectively.

Our starting plasmids in the construction of pTATΔcys-HE2.85 and pTATΔcys-HE2.121 were, respectively, pET8c-85 and pET8c-123 (both described above). We digested pET8c-85 and pET8c-123 with BglII and NcoI, and isolated the large fragment in each case (4769 base pairs from pET8c-85 or 4880 base pairs from pET8c-123) for use as a vector. In both vectors, the E2 coding regions begin at the NcoI site. Into both vectors, we inserted the 220 bp BglII-AatII fragment from plasmid pTATΔcys, and a synthetic fragment. The 5' end of the BglII-AatII fragment is upstream of the T7 promoter and encodes the first 40 residues of tatΔcys (i.e., residues 1–21, 38–56). The synthetic fragment consisting of annealed oligonucleotides 374.67 (SEQ ID NO:25) and 374.68 (SEQ ID NO:26), encoded tat residues 57–72, with an AatII overhang at the 5' end and an NcoI overhang at the 3' end.

JB Series of Genetic Fusions

Plasmid pJB106 encodes a fusion protein (FIG. 18) (SEQ ID NO:38) in which an amino-terminal methionine residue is followed by tat residues 47–58 and then HPV-16 E2 residues 245–365. To obtain pJB106, we carried out a three-way ligation, schematically depicted in FIG. 17. We generated a 4602 base pair vector fragment by digesting plasmid pET8c with NcoI and BamHI. One insert was a 359 base pair MspI-BamHI fragment from pET8c-123, encoding HPV-16 E2 residues 248–365. The other insert was a synthetic fragment consisting of the annealed oligonucleotide pair, 374.185 (SEQ ID NO:27) and 374.186 (SEQ ID NO:28). The synthetic fragment encoded the amino-terminal methionine and tat residues 47–58, plus HPV16 residues 245–247 (i.e., ProAspThr). The synthetic fragment had an NcoI overhang at the 5' end and an MspI overhang at the 3' end.

We obtained plasmids pJB117 (SEQ ID NO:59), pJB118 (SEQ ID NO:60), pJB119 (SEQ ID NO:61), pJB120 (SEQ ID NO:62) and pJB122 (SEQ ID NO:63) by PCR deletion cloning in a manner similar to that used for pTATΔcys (described above and in FIG. 14). We constructed plasmids pJB117 and pJB118 by deleting segments of pTATΔcys-HE2.121. We constructed plasmids pJB119 and pJB120 by deleting segments of pTATΔcys-161. In all four clonings, we used PCR primer 374.122 (SEQ ID NO:29) to cover the HindIII site downstream of the tat-E2 coding region. In each case, the other primer spanned the NdeI site at the start of the tatacys coding sequence, and deleted codons for residues at the beginning of tatΔcys (i.e., residues 2–21 and 38–46 for pJB117 and pJB119; and residues 2–21 for pJB118 and pJB120). For deletion of residues 2–21, we used primer 379.11 (SEQ ID NO:30). For deletion of residues 2–21 and 38–46, we used primer 379.12 (SEQ ID NO:31). Following the PCR reaction, we digested the PCR products with NdeI and HindIII. We then cloned the resulting restriction fragments into vector pTATΔcys-HE2.121, which had been previously digested with NdeI plus HindIII to yield a 4057 base pair receptor fragment. Thus, we constructed expression plasmids encoding fusion proteins consisting of amino acid residues as follows:

JB117=Tat47-72-HPV16 E2 245–365;
JB118=Tat38-72-HPV16 E2 245–365;
JB119=Tat47-62-BPV1 E2 250–410; and
JB120=Tat38-62-BPV1 E2 250–410.

We constructed pJB122, encoding tat residues 8–58 followed by HPV16 E2 residues 245–365 (i.e., the E2 carboxy-terminal 121 amino acids), by deleting from pJB118 codons for tat residues 59–72. We carried out this deletion by PCR, using primer 374.13 (SEQ ID NO:32), which covers the AatII site within the tat coding region, and primer 374.14 (SEQ ID NO:33), which covers the AatII site slightly downstream of the unique HindIII site downstream of the Tat-E2 gene. We digested the PCR product with AatII and isolated the resulting restriction fragment. In the final pJB122 construction step, we inserted the isolated AatII fragment into AatII-digested vector pJB118.

It should be noted that in all five of our pJB constructs described above, the tat coding sequence was preceded by a methionine codon for initiation of translation.

Purification of Tat-E2 Fusion Proteins

In all cases, we used *E.coli* to express our tat-E2 genetic fusions. Our general procedure for tat-E2 protein purification included the following initial steps: pelleting the cells; resuspending them in 8–10 volumes of lysis buffer (25 mM Tris (pH 7.5), 25 mM NaCl, 1 mM DTT, 0.5 mM EDTA) containing protease inhibitors—generally, 1 mM PMSF, 4 μg/ml E64, 50 μg/ml aprotinin, 50 μg/ml pepstatin A, and 3 mM benzamidine); lysing the cells in a French press (2 passes at 12,000 psi); and centrifuging the lysates at 10,000–12,000×g for 1 hour (except FTE proteins), at 4° C. Additional steps employed in purifying particular tat-E2 fusion proteins are described below.

E2.103 and E2.249—Following centrifugation of the lysate, we loaded the supernatant onto a Fast S Sepharose column and eluted the E2.103 or E2.249 protein with 1 M NaCl. We then further purified the E2.103 or E2.249 by chromatography on a P60 gel filtration column equilibrated with 100 mM HEPES (pH 7.5), 0.1 mM EDTA and 1 mM DTT.

FTE103—Following centrifugation of the lysate at 10,000×g for 10 min. at 4° C., we recovered the FTE103 protein (which precipitated) by resuspending the pellet in 6 M urea and adding solid guanidine-HCl to a final concentration of 7 M. After centrifuging the suspension, we purified the FTE103 protein from the supernatant by chromatography on an A.5M gel filtration column in 6 M guanidine, 50 mM sodium phosphate (pH 5.4), 10 mM DTT. We collected the FTE103-containing fractions from the gel filtration column according to the appearance of a band having an apparent molecular weight of 19 kDa on Coomassie-stained SDS polyacrylamide electrophoresis gels.

FTE403—Our purification procedure for FTE403 was essentially the same as that for FTE103, except that FTE403 migrated on the gel filtration column with an apparent molecular weight of 25 kDa.

FTE501—Following centrifugation of the lysate at 10,000×g, for 30 minutes, we resuspended the pellet in 6 M urea, added solid guanidine-HCl to a final concentration of 6 M, and DTT to a concentration of 10 mM. After 30 minutes at 37° C., we clarified the solution by centrifugation at 10,000×g for 30 minutes. We then loaded the sample onto an A.5 agarose gel filtration column in 6 M guanidine-HCl, 50 mM sodium phosphate (pH 5.4), 10 mM DTT and collected the FTE501-containing fractions from the gel filtration column, according to the appearance of a band having an apparent molecular weight of 40 kDa on Coomassie-stained SDS polyacrylamide electrophoresis gels. We loaded the gel filtration-purified FTE501 onto a $C_{18}$ reverse phase HPLC column and eluted with a gradient of 0–75% acetonitrile in 0.1% trifluoroacetic acid. We collected the FTE501 protein in a single peak with an apparent molecular weight of 40 kDa.

TatΔcys-105—Following centrifugation of the lysate, we loaded the supernatant onto a Q-Sepharose column equilibrated with 25 mM Tris (pH 7.5), 0.5 mM EDTA. We loaded the Q-Sepharose column flow-through onto an S-Sepharose column equilibrated with 25 mM MES (pH 6.0), after adjusting the Q-Sepharose column flow-through to about pH 6.0 by adding MES (pH 6.0) to a final concentration of 30 mM. We recovered the tatΔcys-105 protein from the S-Sepharose column by application of sequential NaCl concentration steps in 25 mM MES (pH 6.0). TatΔcys-105 eluted in the pH 6.0 buffer at 800–1000 mM NaCl.

TatΔcys-161—Following centrifugation of the lysate, we loaded the supernatant onto an S-Sepharose column equilibrated with 25 mM Tris (pH 7.5), 0.5 mM EDTA. We recovered the tatΔcys-161 from the S-Sepharose column by application of a NaCl step gradient in 25 mM Tris (pH 7.5). TatΔcys-161 eluted in the pH 7.5 buffer at 500–700 mM NaCl.

TatΔcys-249—Following centrifugation of the lysate, we loaded the supernatant onto a Q-Sepharose column equilibrated with 25 mM Tris (pH 7.5), 0.5 mM EDTA. We recovered the tatΔcys-249 from the S-Sepharose column by application of a NaCl step gradient in 25 mM Tris (pH 7.5). TatΔcys-249 eluted in the 600–800 mM portion of the NaCl step gradient.

TatΔcys-HE2.85 and TatΔcys-HE2.121—Following centrifugation of the lysate, we loaded the supernatant onto a Q-Sepharose column. We loaded the flow-through onto an S-Sepharose column. We recovered the tatΔcys-HE2.85 or tatΔcys-HE2.121 from the S-Sepharose column by application of a NaCl step gradient. Both proteins eluted with 1 M NaCl.

HPV E2 and HPV E2CCSS—See Example 9 (above).

JB106—Following centrifugation of the lysate, and collection of the supernatant, we added NaCl to 300 mM. We loaded the supernatant with added NaCl onto an S-Sepharose column equilibrated with 25 mM HEPES (pH 7.5). We treated the column with sequential salt concentration steps in 25 mM HEPES (pH 7.5), 1.5 mM EDTA, 1 mM DTT. We eluted the JB106 protein from the S-Sepharose column with 1 M NaCl.

JB117—Following centrifugation of the lysate, and collection of the supernatant, we added NaCl to 300 mM. Due to precipitation of JB117 at 300 mM NaCl, we diluted the JB117 supernatant to 100 mM NaCl and batch-loaded the protein onto the S-Sepharose column. We eluted JB117 from the S-Sepharose column with 1 M NaCl in 25 mM Tris (pH 7.5), 0.3 mM DTT.

JB118—Following centrifugation of the lysate, and collection of the supernatant, we added NaCl to 300 mM. We loaded the supernatant with added NaCl onto an S-Sepharose column equilibrated with 25 mM Tris (pH 7.5). We eluted the JB118 protein from the S-Sepharose column with 1 M NaCl in 25 mM Tris (pH 7.5), 0.3 mM DTT.

JB119, JB120, JB121 and JB122—Following centrifugation of the lysate, and collection of the supernatant, we added NaCl to 150 mM for JB119 and JB121, and 200 mM for JB120 and JB122. We loaded the supernatant with added NaCl onto an S-Sepharose column equilibrated with 25 mM Tris (pH 7.5). We eluted proteins JB119, JB120, JB121 and JB122 from the S-Sepharose column with 1 M NaCl in 25 mM Tris (pH 7.5), 0.3 mM DTT.

EXAMPLE 14

E2 Repression Assays—Additional Conjugates

We tested our tat-E2 fusion proteins for inhibition of transcriptional activation by the full-length papillomavirus E2 protein ("repression"). We measured E2 repression with a transient co-transfection assay in COS7 cells. The COS7 cells used in this assay were maintained in culture for only short periods of time. We thawed the COS7 cells at passage 13 and used them only through passage 25. Long periods of propagation led to low levels of E2 transcriptional activation and decreased repression and reproducibility. Our repression assay and method of computing repression activity are described in Example 9 (above). For the conjugates TxE2.103, TxE22.249, FTE103, FTE202, FTE403 and FTE501, we substituted the BPV-1 E2 transactivator, in equal amount, for the HPV-16 E2 transactivator. Accordingly, instead of transfecting with the HPV-16 E2 expression plasmid pAHE2, we transfected with the BPV-1 E2 expression plasmid pXB323, which is fully described in U.S. Pat. No. 5,219,990.

Figure 19:
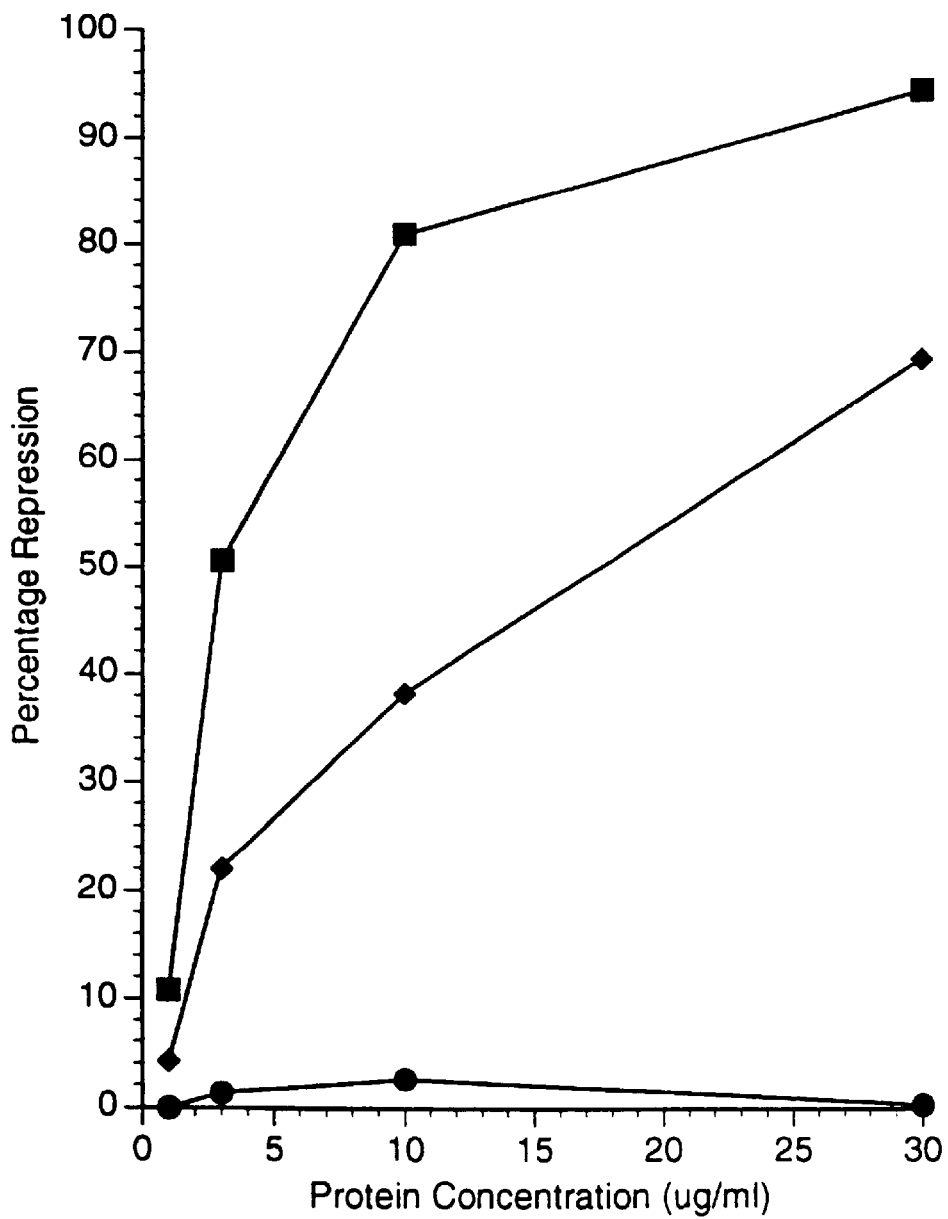
FIG. 19 summarizes the results of E2 repression assays involving JB106 (squares), TxHE2CCSS (diamonds) and HE2.123 (circles). The assays were carried out in COS7 cells, without chloroquine, as described in Example 14.

The genetic fusion protein JB106 has consistently been our most potent tat-E2 repressor conjugate. Data from a repression assay comparing JB106 and TxHE2CCSS are shown in Table III. FIG. 19 graphically depicts the results presented in Table III.

In addition to JB106, several other tat-E2 repressor conjugates have yielded significant repression. As shown in Table IV, TxHE2, TxHE2CCSS, JB117, JB118, JBll9, JB120 and JB122 displayed repression levels in the ++ range.

TABLE III

| Protein added (μg/ml) | cpm-bkgd* | average of duplicates | average cpm-bkgd | % repression |
|---|---|---|---|---|
| 0 | 3,872 | | | |
| 0 | 3,694 | 3783 | — | — |
| 0 | 17,896 | | | |
| 0 | 18,891 | 18,393 | 14,610 | — |
| 1 JB106 | 16,384 | | | |
| 1 JB106 | 17,249 | 16,816 | 13,033 | 10.8 |
| 3 JB106 | 11,456 | | | |
| 3 JB106 | 10,550 | 11,003 | 7,220 | 50.6 |
| 10 JB106 | 6,170 | | | |
| 10 JB106 | 7,006 | 6,588 | 2,805 | 81.0 |
| 30 JB106 | 4,733 | | | |
| 30 JB106 | 4,504 | 4,618 | 835 | 94.3 |
| 1 TxHE2CCSS | 17,478 | | | |
| 1 TxHE2CCSS | 18,047 | 17,762 | 13,979 | 4.3 |
| 3 TxHE2CCSS | 14,687 | | | |
| 3 TxHE2CCSS | 15,643 | 15,165 | 11,382 | 22.1 |
| 10 TxHE2CCSS | 12,914 | | | |
| 10 TxHE2CCSS | 12,669 | 12,791 | 9,008 | 38.3 |
| 30 TxHE2CCSS | 7,956 | | | |
| 30 TxHE2CCSS | 8,558 | 8,257 | 4,474 | 69.4 |
| 1 HE2.123 | 18,290 | | | |
| 1 HE2.123 | 18,744 | 18,517 | 14,734 | 0 |
| 3 HE2.123 | 17,666 | | | |
| 3 HE2.123 | 18,976 | 18,321 | 14,538 | 1.3 |
| 10 HE2.123 | 18,413 | | | |
| 10 HE2.123 | 17,862 | 18,137 | 14,354 | 2.6 |
| 30 HE2.123 | 18,255 | | | |
| 30 HE2.123 | 18,680 | 18,467 | 14,684 | 0.3 |

*Bkgd= 158 cpm.

Table IV summarizes our tat-E2 repressor assay results. Although we tested all of our tat-E2 repressor conjugates in similar assays, the conjugates were not all simultaneously tested in the same assay. Accordingly, we have expressed the level of repression activity, semi-quantitatively, as +++, ++, +, +/−, or −, with +++ being strong repression, and − being no detectable repression. FIG. 19 illustrates the repression activity rating system used in Table IV. JB106 exemplifies the +++ activity level. TxHE2CCSS exemplifies the ++ activity level. The negative control, HE2.123, exemplifies the − activity level. The + activity level is intermediate between the activity observed with TxHE2CCSS and HE2.123. The two conjugates whose activity is shown as +/− had weak (but detectable) activity in some assays and no detectable activity in other assays.

TABLE IV

| Protein | Tat residues | E2 residues | Repression Level |
|---|---|---|---|
| TxE2.103 | 37–72 | BPV-1 308–410 | + |
| TxE2.249 | 37–72 | BPV-1 162–410 | − |
| TxHE2 | 37–72 | HPV-16 245–365 | ++ |
| TxHE2CCSS | 37–72 | HPV-16 245–365 | ++ |
| FTE103 | 1–67 | BPV-1 306–410 | − |
| FTE208 | 1–62 | BPV-1 311–410 | − |
| FTE403 | 1–62 | BPV-1 250–410 | − |
| FTE501 | 1–62 | BPV-1 162–410 | − |
| TatΔcys-105 | 1–21, 38–67 | BPV-1 306–410 | − |
| TatΔcys-161 | 1–21, 38–62 | BPV-1 250–410 | +/− |
| TatΔcys-249 | 1–21, 38–62 | BPV-1 162–410 | +/− |
| TatΔcys-HE2.85 | 1–21, 38–72 | HPV-16 281–365 | + |
| TatΔcys-HE2.121 | 1–21, 38–72 | HPV-16 245–365 | + |
| JB106 | 47–58 | HPV-16 245–365 | +++ |
| JB117 | 47–72 | HPV-16 245–365 | ++ |
| JB118 | 38–72 | HPV-16 245–365 | ++ |
| JB119 | 47–62 | BPV-1 250–410 | ++ |
| JB120 | 38–62 | BPV-1 250–410 | ++ |
| JB122 | 38–58 | HPV-16 245–365 | ++ |

FTE103, FTE403, FTE208 and FTE501, the four conjugates having the tat amino-terminal region (i.e., residues 1–21) and the cysteine-rich region (i.e., residues 22–37) were completely defective for repression. Since we have shown, by indirect immunofluorescence, that FTE501 enters cells, we consider it likely that the E2 repressor activity has been lost in the FTE series as a result of the linkage to the tat transport polypeptide. Our data show that the absence of the cysteine-rich region of the tat moiety generally increased E2 repressor activity. In addition, the absence of the cysteine-rich region in tat-E2 conjugates appeared to increase protein production levels in *E.coli*, and increase protein solubility, without loss of transport into target cells. Deletion of the amino-terminal region of tat also increased E2 repressor activity. Fusion protein JB106, with only tat residues 47–58, was the most potent of our tat-E2 repressor conjugates. However, absence of the tat cysteine-rich region does not always result in preservation of E2 repressor activity in the conjugate. For example, the chemical conjugate TxE2.249 was insoluble and toxic to cells. Thus, linkage of even a cysteine-free portion of tat may lead to a non-functional E2 repressor conjugate.

EXAMPLE 15

Cleavable E2 Conjugates

Chemical conjugation of tat moieties to E2 protein resulted in at least a 20-fold reduction in binding of the E2 protein to E2 binding sites on DNA (data not shown). Therefore, we conducted experiments to evaluate cleavable cross-linking between the tat transport moiety and the E2 repressor moiety. We tested various cleavable cross-linking methods.

In one series of experiments, we activated the cysteine sulfhydryl groups of HPV E2-CCSS protein with aldrithiol in 100 mM HEPES (pH 7.5), 500 mM NaCl. We isolated the activated E2 repressor by gel filtration chromatography and treated it with tat37-72. We achieved low cross-linking efficiency because of rapid E2-CCSS dimer formation upon treatment with aldrithiol. To avoid this problem, we put the E2-CCSS into 8 M urea, at room temperature, and treated it with aldrithiol at 23° C. for 60 minutes under denaturing conditions. We then refolded the E2CCSS-aldrithiol adduct, isolated it by gel filtration chromatography, and then allowed it to react with tat37-72. This procedure resulted in excellent cross-linking. We also cross-linked E2CSSS and E2CCSC to tat37-72, using a modification of the urea method, wherein we used S-Sepharose chromatography instead of gel filtration to isolate the E2-aldrithiol adducts. This modification increased recovery of the adducts and resulted in cross-linkage of approximately 90% of the E2 starting material used in the reaction.

The cleavable tat-E2 conjugates exhibited activity in the repression assay. However, the repression activity of the cleavable conjugates was slightly lower than that of similar conjugates cross-linked irreversibly. The slightly lower activity of the cleavable conjugates may be a reflection of protein half-life in the cells. Tat is relatively stable in cells. E2 proteins generally have short half-lives in cells. Thus, irreversible cross-linkage between a tat moiety and an E2 moiety may stabilize the E2 moiety.

EXAMPLE 16

Herpes Simplex Virus Repressor Conjugate

Herpes simplex virus ("HSV") encodes a transcriptional activator, VP16, which induces expression of the immediate early HSV genes. Friedman et al. have produced an HSV VP16 repressor by deleting the carboxy-terminal transactivation domain of VP16 ("Expression of a Truncated Viral Trans-Activator Selectively Impedes Lytic Infection by Its Cognate Virus", *Nature*, 335, pp. 452–54 (1988)). We have produced an HSV-2 VP16 repressor in a similar manner.

To test cellular uptake and VP16 repressor activity of transport polypeptide-VP16 repressor conjugates, we simultaneously transfected a VP16-dependent reporter plasmid and a VP16 repressor plasmid into COS7 cells. Then we exposed the transfected cells to a transport polypeptide-VP16 repressor conjugate or to an appropriate control. The repression assay, described below, was analogous to the E2 repression assay described above, in Example 9.

VP16 Repression Assay Plasmids

Our reporter construct for the VP16 repression assay was plasmid p175kCAT, obtained from G. Hayward (see, P. O'Hare and G. S. Hayward, "Expression of Recombinant Genes Containing Herpes Simplex Virus Delayed-Early and Immediate-Early Regulatory Regions and Trans Activation by Herpes Virus Infection", *J. Virol.*, 52, pp. 522–31 (1984)). Plasmid p175kCAT contains the HSV-1 IE175 promoter driving a CAT reporter gene.

Our HSV-2 transactivator construct for the VP16 repression assay was plasmid pXB324, which contained the wild-type HSV-2 VP16 gene under the control of the chicken β-actin promoter. We constructed pXB324 by inserting into pXB100 (P. Han et al., "Transactivation of Heterologous Promoters by HIV-1 Tat", *Nuc. Acids Res.*, 19, pp. 7225–29 (1991)), between the XhoI site and BamHI site, a 280 base pair fragment containing the chicken β-actin promoter and a 2318 base pair BamHI-EcoRI fragment from plasmid pCA5 (O'Hare and Hayward, supra) encoding the entire wild type HSV-2 VP16 protein.

Tat-VP16 Repressor Fusion Protein

We produced in bacteria fusion protein tat-VP16R.GF (SEQ ID NO:58), consisting of amino acids 47–58 of HIV tat protein followed by amino acids 43–412 of HSV VP16 protein. For bacterial production of a tat-VP16 repressor fusion protein, we constructed plasmid pET/tat-VP16R.GF, in a three-piece ligation. The first fragment was the vector pET-3d (described above under the alternate desgnatiion "pET-8c") digested with NcoI and BglII (approximately 4600 base pairs). The second fragment consisted of synthetic oligonucleotides 374.219 (SEQ ID NO:39) and 374.220 (SEQ ID NO:40), annealed to form a double-stranded DNA molecule. The 5' end of the synthetic fragment had an NcoI overhang containing an ATG translation start codon. Following the start codon were codons for tat residues 47–58. Immediately following the tat codons, in frame, were codons for VP16 residues 43–47. The 3' terminus of the synthetic fragment was a blunt end for ligation to the third fragment, an 1134 base pair PvuII-BglII fragment from pXB324R4, containing codons 48–412 of HSV-2 VP16. We derived pXB324R4 from pXB324 (described above). Plasmid pXB324R2 was an intermediate in the construction of pXB324R4.

We constructed pXB324R2 by inserting into pXB100 a 1342 base pair BamHI-AatII fragment, from pXB324, encoding the N-terminal 419 amino acids of HSV-2 VP16. To provide an in-frame stop codon, we used a 73 base pair AatII-EcoRI fragment from pSV2-CAT (C. M. Gorman et al., *Molecular& Cellular Biology*, 2, pp. 1044–51 (1982)). Thus, pXB324R2 encoded the first 419 amino acids of HSV-2 VP16 and an additional seven non-VP16 amino acids preceding the stop codon. To construct pXB324R4, we carried out a 3-piece ligation involving a 5145 base pair MluI-EcoRI fragment from pXB324R2, and two insert fragments. One insert was a 115 base pair MluI-NspI fragment from pXB324R2, encoding the first 198 residues of VP16. The second insert fragment was a double-stranded synthetic DNA molecule consisting of the synthetic oligonucleotides 374.32 (SEQ ID NO:41) and 374.33 (SEQ ID NO:42). When annealed, these oligonucleotides formed a 5' NspI sticky end and a 3' EcoRI sticky end. This synthetic fragment encoded VP16 residues 399–412, followed by a termination codon. Thus, plasmid pXB324R4 differed from pXB324R2 by lacking codons for VP16 amino acids 413–419 and the seven extraneous amino acids preceding the stop codon.

Purification of tat-VP16R.GF Fusion Protein

We expressed our genetic construct for tat-VP16R.GF in *E.coli*. We harvested the transformed *E.coli* by centrifugation; resuspended the cells in 8–10 volumes of lysis buffer (25 mM Tris (pH 7.5), 25 mM NaCl, 1 mM DTT, 0.5 mM EDTA, 1 mM PMSF, 4 µg/ml E64, 50 µg/ml aprotinin, 50 µg/ml pepstatin A, and 3 mM benzamidine); lysed the cells in a French press (2 passes at 12,000 psi); and centrifuged the lysate at 10,000 to 12,000×g for 1 hour, at 4° C. Following centrifugation of the lysate, we loaded the supernatant onto a Fast Q-Sepharose column equilibrated with 25 mM Tris (pH 7.5), 0.5 mM EDTA. We loaded the Q-Sepharose flow-through onto a Fast S-Sepharose column equilibrated in 25 mM MES (pH 6.0), 0.1 mM EDTA, 2 mM DTT. We recovered the tat-VP16 fusion protein from the S-Sepharose column with sequential NaCl concentration steps in 25 mM MES (pH 6.0), 0.1 mM EDTA, 2 mM DTT. The tat-VP16 fusion protein eluted in the 600–1000 mM NaCl fractions.

VP16 Repression Assay

We seeded HeLa cells in 24-well culture plates at $10^5$ cells/well. The following day, we transfected the cells, using the DEAE-dextran method, as described by B. R. Cullen, "Use of Eukaryotic Expression Technology in the Functional Analysis of Cloned Genes", *Meth. Enzymol.*, vol. 152, p. 684 (1987). We precipitated the DNA for the transfections and redissolved it, at a concentration of approximately 100 µg/ml, in 100 mM NaCl, 10 mM Tris (pH 7.5). For each transfection, the DNA-DEAE mix consisted of: 200 ng p175kCAT (+/−1 ng pXB324) or 200 ng pSV-CAT (control), 1 mg/ml DEAE-dextran, and PBS, to a final volume of 100 µl. We exposed the cells to this mixture for 15–20 minutes, at 37° C., with occasional rocking of the culture plates. We then added to each well, 1 ml fresh DC medium (DMEM+ 10% serum) with 80 µM chloroquine. After incubating the cells at 37° C. for 2.5 hours, we aspirated the medium from each well and replaced it with fresh DC containing 10% DMSO. After 2.5 minutes at room temperature, we aspirated the DMSO-containing medium and replaced it with fresh DC containing 0, 10 or 50 µg/ml purified tat-VP16.GF. The following day, we replaced the medium in each well with fresh medium of the same composition. Twenty-four hours later, we lysed the HeLa cells with 0.65% NP-40 (detergent) in 10 mM Tris (pH 8.0), 1 mM EDTA, 150 mM NaCl. We measured the protein concentration in each extract, for sample normalization in the assay.

At a tat-VP16.GF concentration of 50 µg/ml, cellular toxicity interfered with the assay. At a concentration of 10 µg/ml, the tat-VP16.GF fusion protein yielded almost complete repression of VP16-dependent CAT expression, with no visible cell death and approximately 30% repression of non-VP16-dependent CAT expression in controls. Thus, we observed specific repression of VP16-dependent transactivation in addition to a lesser amount non-specific repression.

EXAMPLE 17

Transport Polypeptide—DNA Conjugates

Transcriptional activation by a DNA-binding transcription factor can be inhibited by introducing into cells DNA having the binding site for that transcription factor. The transcription factor becomes bound by the introduced DNA and is rendered unavailable to bind at the promoter site where it normally functions. This strategy has been employed to inhibit transcriptional activation by NF-κB (Bielinska et al., "Regulation of Gene Expression with Double-Stranded Phosphorothioate Oligonucleotides", *Science*, vol. 250, pp. 997–1000 (1990)). Bielinska et al. observed dose-dependent inhibition when the double stranded DNA was put in the cell culture medium. We conjugated the transport polypeptide tat 37-72 to the double stranded DNA molecule to determine whether such conjugation would enhance the inhibition by increasing the cellular uptake of the DNA.

We purchased four custom-synthesized 39-mer phosphorothioate oligonucleotides designated NF1, NF2, NF3 and NF4, having nucleotide sequences (SEQ ID NO:43), (SEQ ID NO:44), (SEQ ID NO:45) and (SEQ ID NO:46), respectively. NF1 and NF2 form a duplex corresponding to the wild type NF-κB binding site. NF3 and NF4 form a duplex corresponding to a mutant NF-κB binding site.

We dissolved NF1 and NF3 in water, at a concentration of approximately 4 mg/ml. We then put 800 µg of NF1 and NF3 separately into 400 µl of 50 mM triethanolamine (pH 8.2), 50 mM NaCl, 10 mM Traut's reagent. We allowed the reaction to proceed for 50 minutes at room temperature. We stopped the reaction by gel filtration on a P6DG column (BioRad, Richmond, Calif.) equilibrated with 50 mM HEPES (pH 6.0), 50 mM NaCl, to remove excess Traut's reagent. We monitored 260 nm absorbance to identify the oligonucleotide-containing fractions. Our recovery of the oligonucleotides was approximately 75%. We then annealed Traut-modified NF1 with NF2 (0.55 mg/ml final concentration) and annealed Traut-modified NF3 with NF4 0.50 mg/ml final concentration). Finally, we allowed 0.4 mg of each Traut-modified DNA to react with 0.6 mg of tat37-72-BMH (prepared as described in Example 9, above), in 1 ml of 100 mM HEPES (pH 7.5), for 60 minutes at room temperature. We monitored the extent of the cross-linking reaction by polyacrylamide gel electrophoresis followed by ethidium bromide staining of the gel. In general, we observed that about 50% of the DNA was modified under these conditions.

These double-stranded DNA molecules were tested, essentially according to the methods of Bielinska et al. (supra), with and without tat linkage, for inhibition of NF-κB transcriptional activation. Tat linkage significantly enhanced the inhibition of transactivation by NF-κB.

Recombinant DNA sequences prepared by the processes described herein are exemplified by a culture deposited in the American Type Culture Collection, Rockville, Md. The *Escherichia coli* culture identified as pJB106 was deposited on Jul. 28, 1993 and assigned ATCC accession number 69368.

While we have described a number of embodiments of this invention, it is apparent that our basic constructions can be altered to provide other embodiments that utilize the processes and products of this invention. Therefore, it will be appreciated that the scope of this invention is to be defined by the appended claims rather than by the specific embodiments that have been presented by way of example.

We claim:

1. A method for delivering a molecule of interest cargo moiety to a cell, the method comprising presenting to the cell an extracellular fusion protein consisting of a cargo moiety and a transport moiety, wherein the transport moiety is characterized by (a) the presence of amino acids 49–57 of HIV tat protein; (b) an absence of amino acids 22–36 of HIV tat protein; and (c) an absence of amino acids 73–86 of HIV tat protein and allowing transport moiety-dependent intracellular delivery of the fusion protein.

2. A method for delivering a molecule of interest cargo moiety to a cell, the method comprising presenting to the cell a covalently linked conjugate consisting of a cargo moiety and a transport polypeptide moiety, wherein the transport polypeptide moiety of the conjugate is characterized by (a) the presence of amino acids 49–57 of HIV tat protein; (b) the absence of amino acids 22–36 of HIV tat protein; and (c) the absence of amino acids 73–86 of HIV tat protein and allowing transport moiety-dependent intracellular delivery of the conjugate.

3. The method of claim 1, wherein the step of presenting comprises presenting a pharmaceutically effective amount of the extracellular fusion protein.

4. The method of claim 2, wherein the step of presenting comprises presenting a pharmaceutically effective amount of the conjugate.

5. The process according to claim 1, wherein the molecule of interest is an antigen.

6. The process according to claim 1, wherein the molecule of interest is a monoclonal antibody.

7. The process according to claim 1, wherein the molecule of interest is selected from the group consisting of: (a) a single stranded nucleic acid and (b) a double stranded nucleic acid.

8. The process according to claim 1, wherein the tat protein is from an HIV-2 virus.

9. A method for delivering an HIV tat protein to a cell, the method comprising the steps of (I) presenting extracellularly to the cell an HIV tat protein and (II) allowing HIV tat protein moiety-dependent intracellular delivery thereof, wherein the HIV tat protein is characterized by (a) the presence of amino acids 49–57 of HIV tat protein; (b) the absence of amino acids 22–36 of HIV tat protein; and (c) the absence of amino acids 73–86 of HIV tat protein.

10. The process according to claim 2, wherein the molecule of interest is selected from the group consisting of therapeutic molecules, prophylactic molecules and diagnostic molecules.

11. The process according to claim 2, wherein the molecule of interest is selected from the group consisting of polypeptides and nucleic acids.

* * * * *

```
SEQUENCE LISTING (1) GENERAL INFORMATION:

(iii) NUMBER OF SEQUENCES: 69

(2) INFORMATION FOR SEQ ID NO:1:

(i) SEQUENCE CHARACTERISTICS:
        (A) LENGTH: 86 amino acids
        (B) TYPE: amino acid
        (D) TOPOLOGY: linear (ii) MOLECULE TYPE: protein (vi) ORIGINAL SOURCE:
        (A) ORGANISM: human immunodeficiency virus
        (B) STRAIN: type 1

(xi) SEQUENCE DESCRIPTION: SEQ ID NO:1:

Met Glu Pro Val Asp Pro Arg Leu Glu Pro Trp Lys His Pro Gly Ser
1               5                  10                  15

Gln Pro Lys Thr Ala Cys Thr Asn Cys Tyr Cys Lys Lys Cys Cys Phe
            20                  25                  30

His Cys Gln Val Cys Phe Ile Thr Lys Ala Leu Gly Ile Ser Tyr Gly
        35                  40                  45

Arg Lys Lys Arg Arg Gln Arg Arg Pro Pro Gln Gly Ser Gln Thr
50                  55                  60

His Gln Val Ser Leu Ser Lys Gln Pro Thr Ser Gln Ser Arg Gly Asp
65                  70                  75                  80

Pro Thr Gly Pro Lys Glu
            85

(2) INFORMATION FOR SEQ ID NO:2:

(i) SEQUENCE CHARACTERISTICS:
        (A) LENGTH: 36 amino acids
        (B) TYPE: amino acid
        (D) TOPOLOGY: linear (ii) MOLECULE TYPE: peptide (xi) SEQUENCE DESCRIPTION: SEQ ID NO:2:

Cys Phe Ile Thr Lys Ala Leu Gly Ile Ser Tyr Gly Arg Lys Lys Arg
1               5                  10                  15

Arg Gln Arg Arg Arg Pro Pro Gln Gly Ser Gln Thr His Gln Val Ser
            20                  25                  30

Leu Ser Lys Gln
        35
```

(2) INFORMATION FOR SEQ ID NO:3:

(i) SEQUENCE CHARACTERISTICS:
        (A) LENGTH: 22 amino acids
        (B) TYPE: amino acid
        (D) TOPOLOGY: linear (ii) MOLECULE TYPE: peptide (xi) SEQUENCE DESCRIPTION: SEQ ID NO:3:

```
Cys Phe Ile Thr Lys Ala Leu Gly Ile Ser Tyr Gly Arg Lys Lys Arg
1               5                   10                  15
Arg Gln Arg Arg Arg Pro
            20
```

(2) INFORMATION FOR SEQ ID NO:4:

(i) SEQUENCE CHARACTERISTICS:
        (A) LENGTH: 24 amino acids
        (B) TYPE: amino acid
        (D) TOPOLOGY: linear (ii) MOLECULE TYPE: peptide (xi) SEQUENCE DESCRIPTION: SEQ ID NO:4:

```
Phe Ile Thr Lys Ala Leu Gly Ile Ser Tyr Gly Arg Lys Lys Arg Arg
1               5                   10                  15
Gln Arg Arg Arg Pro Gly Gly Cys
            20
```

(2) INFORMATION FOR SEQ ID NO:5:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:5:

```
Cys Gly Gly Tyr Gly Arg Lys Lys Arg Arg Gln Arg Arg Arg Pro
1               5                   10                  15
```

(2) INFORMATION FOR SEQ ID NO:6:

(i) SEQUENCE CHARACTERISTICS:
        (A) LENGTH: 15 amino acids
        (B) TYPE: amino acid
        (D) TOPOLOGY: linear (ii) MOLECULE TYPE: peptide (xi) SEQUENCE DESCRIPTION: SEQ ID NO:6:

```
Tyr Gly Arg Lys Lys Arg Arg Gln Arg Arg Arg Pro Gly Gly Cys
1               5                   10                  15
```

(2) INFORMATION FOR SEQ ID NO:7:

(i) SEQUENCE CHARACTERISTICS:
        (A) LENGTH: 56 amino acids
        (B) TYPE: amino acid
        (D) TOPOLOGY: linear (ii) MOLECULE TYPE: peptide (xi) SEQUENCE DESCRIPTION: SEQ ID NO:7:

```
Met Glu Pro Val Asp Pro Arg Leu Glu Pro Trp Lys His Pro Gly Ser
1               5                   10                  15

Gln Pro Lys Thr Ala Phe Ile Thr Lys Ala Leu Gly Ile Ser Tyr Gly
                20                  25                  30

Arg Lys Lys Arg Arg Gln Arg Arg Pro Pro Gln Gly Ser Gln Thr
                35                  40                  45

His Gln Val Ser Leu Ser Lys Gln
    50                  55
```

(2) INFORMATION FOR SEQ ID NO:8:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:8:

```
GATCCCAGAC CACCAGGTT TCTCTGTCGG GCCCTTAAG                    39
```

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:9:

```
AATTCTTAAG GGCCCGACAG AGAAACCTGG TGGGTCTGG                   39
```

(2) INFORMATION FOR SEQ ID NO:10:

(i) SEQUENCE CHARACTERISTICS:
        (A) LENGTH: 5098 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:10:

```
TTGAAGACGA AAGGGCCTCG TGATACGCCT ATTTTTATAG GTTAATGTCA TGATAATAAT    60

GGTTTCTTAG ACGTCAGGTG GCACTTTTCG GGGAAATGTG CGCGGAACCC CTATTTGTTT   120

ATTTTTCTAA ATACATTCAA ATATGTATCC GCTCATGAGA CAATAACCCT GATAAATGCT   180

TCAATAATAT TGAAAAAGGA AGAGTATGAG TATTCAACAT TTCCGTGTCG CCCTTATTCC   240

CTTTTTTGCG GCATTTTGCC TTCCTGTTTT TGCTCACCCA GAAACGCTGG TGAAAGTAAA   300

AGATGCTGAA GATCAGTTGG GTGCACGAGT GGGTTACATC GAACTGGATC TCAACAGCGG   360

TAAGATCCTT GAGAGTTTTC GCCCCGAAGA ACGTTTTCCA ATGATGAGCA CTTTTAAAGT   420

TCTGCTATGT GGCGCGGTAT TATCCCGTGT TGACGCCGGG CAAGAGCAAC TCGGTCGCCG   480

CATACACTAT TCTCAGAATG ACTTGGTTGA GTACTCACCA GTCACAGAAA AGCATCTTAC   540

GGATGGCATG ACAGTAAGAG AATTATGCAG TGCTGCCATA ACCATGAGTG ATAACACTGC   600

GGCCAACTTA CTTCTGACAA CGATCGGAGG ACCGAAGGAG CTAACCGCTT TTTTGCACAA   660

CATGGGGGAT CATGTAACTC GCCTTGATCG TTGGGAACCG GAGCTGAATG AAGCCATACC   720
```

-continued

| | |
|---|---|
| AAACGACGAG CGTGACACCA CGATGCCTGC AGCAATGGCA ACAACGTTGC GCAAACTATT | 780 |
| AACTGGCGAA CTACTTACTC TAGCTTCCCG GCAACAATTA ATAGACTGGA TGGAGGCGGA | 840 |
| TAAAGTTGCA GGACCACTTC TGCGCTCGGC CCTTCCGGCT GGCTGGTTTA TTGCTGATAA | 900 |
| ATCTGGAGCC GGTGAGCGTG GGTCTCGCGG TATCATTGCA GCACTGGGGC CAGATGGTAA | 960 |
| GCCCTCCCGT ATCGTAGTTA TCTACACGAC GGGGAGTCAG GCAACTATGG ATGAACGAAA | 1020 |
| TAGACAGATC GCTGAGATAG GTGCCTCACT GATTAAGCAT TGGTAACTGT CAGACCAAGT | 1080 |
| TTACTCATAT ATACTTTAGA TTGATTTAAA ACTTCATTTT TAATTTAAAA GGATCTAGGT | 1140 |
| GAAGATCCTT TTTGATAATC TCATGACCAA AATCCCTTAA CGTGAGTTTT CGTTCCACTG | 1200 |
| AGCGTCAGAC CCCGTAGAAA AGATCAAAGG ATCTTCTTGA GATCCTTTTT TTCTGCGCGT | 1260 |
| AATCTGCTGC TTGCAAACAA AAAAACCACC GCTACCAGCG GTGGTTTGTT TGCCGGATCA | 1320 |
| AGAGCTACCA ACTCTTTTTC CGAAGGTAAC TGGCTTCAGC AGAGCGCAGA TACCAAATAC | 1380 |
| TGTCCTTCTA GTGTAGCCGT AGTTAGGCCA CCACTTCAAG AACTCTGTAG CACCGCCTAC | 1440 |
| ATACCTCGCT CTGCTAATCC TGTTACCAGT GGCTGCTGCC AGTGGCGATA AGTCGTGTCT | 1500 |
| TACCGGGTTG GACTCAAGAC GATAGTTACC GGATAAGGCG CAGCGGTCGG GCTGAACGGG | 1560 |
| GGGTTCGTGC ACACAGCCCA GCTTGGAGCG AACGACCTAC ACCGAACTGA GATACCTACA | 1620 |
| GCGTGAGCAT TGAGAAAGCG CCACGCTTCC CGAAGGGAGA AAGGCGGACA GGTATCCGGT | 1680 |
| AAGCGGCAGG GTCGGAACAG GAGAGCGCAC GAGGGAGCTT CCAGGGGGAA ACGCCTGGTA | 1740 |
| TCTTTATAGT CCTGTCGGGT TTCGCCACCT CTGACTTGAG CGTCGATTTT TGTGATGCTC | 1800 |
| GTCAGGGGGG CGGAGCCTAT GGAAAAACGC CAGCAACGCG GCCTTTTTAC GGTTCCTGGC | 1860 |
| CTTTTGCTGG CCTTTTGCTC ACATGTTCTT TCCTGCGTTA TCCCCTGATT CTGTGGATAA | 1920 |
| CCGTATTACC GCCTTTGAGT GAGCTGATAC CGCTCGCCGC AGCCGAACGA CCGAGCGCAG | 1980 |
| CGAGTCAGTG AGCGAGGAAG CGGAAGAGCG CCTGATGCGG TATTTTCTCC TTACGCATCT | 2040 |
| GTGCGGTATT TCACACCGCA TATATGGTGC ACTCTCAGTA CAATCTGCTC TGATGCCGCA | 2100 |
| TAGTTAAGCC AGTATACACT CCGCTATCGC TACGTGACTG GGTCATGGCT GCGCCCCGAC | 2160 |
| ACCCGCCAAC ACCCGCTGAC GCGCCCTGAC GGGCTTGTCT GCTCCCGGCA TCCGCTTACA | 2220 |
| GACAAGCTGT GACCGTCTCC GGGAGCTGCA TGTGTCAGAG GTTTTCACCG TCATCACCGA | 2280 |
| AACGCGCGAG GCAGCTGCGG TAAAGCTCAT CAGCGTGGTC GTGAAGCGAT TCACAGATGT | 2340 |
| CTGCCTGTTC ATCCGCGTCC AGCTCGTTGA GTTTCTCCAG AAGCGTTAAT GTCTGGCTTC | 2400 |
| TGATAAAGCG GGCCATGTTA AGGGCGGTTT TTTCCTGTTT GGTCACTTGA TGCCTCCGTG | 2460 |
| TAAGGGGGAA TTTCTGTTCA TGGGGGTAAT GATACCGATG AAACGAGAGA GGATGCTCAC | 2520 |
| GATACGGGTT ACTGATGATG AACATGCCCG GTTACTGGAA CGTTGTGAGG GTAAACAACT | 2580 |
| GGCGGTATGG ATGCGGCGGG ACCAGAGAAA AATCACTCAG GGTCAATGCC AGCGCTTCGT | 2640 |
| TAATACAGAT GTAGGTGTTC CACAGGGTAG CCAGCAGCAT CCTGCGATGC AGATCCGGAA | 2700 |
| CATAATGGTG CAGGGCGCTG ACTTCCGCGT TTCCAGACTT TACGAAACAC GGAAACCGAA | 2760 |
| GACCATTCAT GTTGTTGCTC AGGTCGCAGA CGTTTTGCAG CAGCAGTCGC TTCACGTTCG | 2820 |
| CTCGCGTATC GGTGATTCAT TCTGCTAACC AGTAAGGCAA CCCCGCCAGC CTAGCCGGGT | 2880 |
| CCTCAACGAC AGGAGCACGA TCATGCGCAC CCGTGGCCAG GACCCAACGC TGCCCGAGAT | 2940 |
| GCGCCGCGTG CGGCTGCTGG AGATGGCGGA CGCGATGGAT ATGTTCTGCC AAGGGTTGGT | 3000 |
| TTGCGCATTC ACAGTTCTCC GCAAGAATTG ATTGGCTCCA ATTCTTGGAG TGGTGAATCC | 3060 |
| GTTAGCGAGG TGCCGCCGGC TTCCATTCAG GTCGAGGTGG CCCGGCTCCA TGCACCGCGA | 3120 |

```
CGCAACGCGG GGAGGCAGAC AAGGTATAGG GCGGCGCCTA CAATCCATGC CAACCCGTTC    3180

CATGTGCTCG CCGAGGCGGC ATAAATCGCC GTGACGATCA GCGGTCCAGT GATCGAAGTT    3240

AGGCTGGTAA GAGCCGCGAG CGATCCTTGA AGCTGTCCCT GATGGTCGTC ATCTACCTGC    3300

CTGGACAGCA TGGCCTGCAA CGCGGGCATC CCGATGCCGC CGGAAGCGAG AAGAATCATA    3360

ATGGGGAAGG CCATCCAGCC TCGCGTCGCG AACGCCAGCA AGACGTAGCC CAGCGCGTCG    3420

GCCGCCATGC CGGCGATAAT GGCCTGCTTC TCGCCGAAAC GTTTGGTGGC GGGACCAGTG    3480

ACGAAGGCTT GAGCGAGGGC GTGCAAGATT CCGAATACCG CAAGCGACAG GCCGATCATC    3540

GTCGCGCTCC AGCGAAAGCG GTCCTCGCCG AAAATGACCC AGAGCGCTGC CGGCACCTGT    3600

CCTACGAGTT GCATGATAAA GAAGACAGTC ATAAGTGCGG CGACGATAGT CATGCCCCGC    3660

GCCCACCGGA AGGAGCTGAC TGGGTTGAAG GCTCTCAAGG GCATCGGTCG ACGCTCTCCC    3720

TTATGCGACT CCTGCATTAG GAAGCAGCCC AGTAGTAGGT TGAGGCCGTT GAGCACCGCC    3780

GCCGCAAGGA ATGGTGCATG CAAGGAGATG GCGCCCAACA GTCCCCCGGC CACGGGGCCT    3840

GCCACCATAC CCACGCCGAA ACAAGCGCTC ATGAGCCCGA AGTGGCGAGC CCGATCTTCC    3900

CCATCGGTGA TGTCGGCGAT ATAGGCGCCA GCAACCGCAC CTGTGGCGCC GGTGATGCCG    3960

GCCACGATGC GTCCGGCGTA GAGGATCGAG ATCTCGATCC CGCGAAATTA ATACGACTCA    4020

CTATAGGGAG ACCACAACGG TTTCCCTCTA GAAATAATTT TGTTTAACTT TAAGAAGGAG    4080

ATATACATAT GGAACCGGTC GACCCGCGTC TGGAACCATG GAAACACCCC GGGTCCCAGC    4140

CGAAAACCGC GTGCACCAAC TGCTACTGCA AAAAATGCTG CTTCCACTGC CAGGTTTGCT    4200

TCATCACCAA AGCCCTAGGT ATCTCTTACG GCCGTAAAAA ACGTCGTCAG CGACGTCGTC    4260

CGCCGCAGGG ATCCCAGACC CACCAGGTTT CTCTGTCGGG CCCGGCGGAC AGCGGCGACG    4320

CCCTGCTGGA GCGCAACTAT CCCACTGGCC GGAGTTCCT CGGCGACGGC GGCGACGTCA     4380

GCTTCAGCAC CCGCGGCACG CAGAACTGGA CGGTGGAGCG GCTGCTCCAG GCGCACCGCC    4440

AACTGGAGGA GCGCGGCTAT GTGTTCGTCG GCTACCACGG CACCTTCCTC GAAGCGGCGC    4500

AAAGCATCGT CTTCGGCGGG GTGCGCGCGC GCAGCCAGGA CCTCGACGCG ATCTGGCGCG    4560

GTTTCTATAT CGCCGGCGAT CCGGCGCTGG CCTACGGCTA CGCCCAGGAC CAGGAACCCG    4620

ACGCACGCGG CCGGATCCGC AACGGTGCCC TGCTGCGGGT CTATGTGCCG CGCTCGAGCC    4680

TGCCGGGCTT CTACCGCACC AGCCTGACCC TGGCCGCGCC GGAGGCGGCG GGCGAGGTCG    4740

AACGGCTGAT CGGCCATCCG CTGCCGCTGC GCCTGGACGC CATCACCGGC CCCGAGGAGG    4800

AAGGCGGGCG CCTGGAGACC ATTCTCGGCT GGCCGCTGGC CGAGCGCACC GTGGTGATTC    4860

CCTCGGCGAT CCCCACCGAC CCGCGCAACG TCGGCGGCGA CCTCGACCCG TCCAGCATCC    4920

CCGACAAGGA ACAGGCGATC AGCGCCCTGC CGGACTACGC CAGCCAGCCC GGCAAACCGC    4980

CGCGCGAGGA CCTGAAGTAA CTGCCGCGAC CGGCCGGCTC CCTTCGCAGG AGCCGGCCTT    5040

CTCGGGGCCT GGCCATACAT CAGGTTTTCC TGATGCCAGC CCAATCGAAT ATGAATTC      5098
```

(2) INFORMATION FOR SEQ ID NO:11:

(i) SEQUENCE CHARACTERISTICS:
        (A) LENGTH: 4910 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:11:

-continued

```
TTGAAGACGA AAGGGCCTCG TGATACGCCT ATTTTTATAG GTTAATGTCA TGATAATAAT      60
GGTTTCTTAG ACGTCAGGTG GCACTTTTCG GGGAAATGTG CGCGGAACCC CTATTTGTTT     120
ATTTTTCTAA ATACATTCAA ATATGTATCC GCTCATGAGA CAATAACCCT GATAAATGCT     180
TCAATAATAT TGAAAAAGGA AGAGTATGAG TATTCAACAT TTCCGTGTCG CCCTTATTCC     240
CTTTTTTGCG GCATTTTGCC TTCCTGTTTT TGCTCACCCA GAAACGCTGG TGAAAGTAAA     300
AGATGCTGAA GATCAGTTGG GTGCACGAGT GGGTTACATC GAACTGGATC TCAACAGCGG     360
TAAGATCCTT GAGAGTTTTC GCCCCGAAGA ACGTTTTCCA ATGATGAGCA CTTTTAAAGT     420
TCTGCTATGT GGCGCGGTAT TATCCCGTGT TGACGCCGGG CAAGAGCAAC TCGGTCGCCG     480
CATACACTAT TCTCAGAATG ACTTGGTTGA GTACTCACCA GTCACAGAAA AGCATCTTAC     540
GGATGGCATG ACAGTAAGAG AATTATGCAG TGCTGCCATA ACCATGAGTG ATAACACTGC     600
GGCCAACTTA CTTCTGACAA CGATCGGAGG ACCGAAGGAG CTAACCGCTT TTTTGCACAA     660
CATGGGGGAT CATGTAACTC GCCTTGATCG TTGGGAACCG GAGCTGAATG AAGCCATACC     720
AAACGACGAG CGTGACACCA CGATGCCTGC AGCAATGGCA ACAACGTTGC GCAAACTATT     780
AACTGGCGAA CTACTTACTC TAGCTTCCCG GCAACAATTA ATAGACTGGA TGGAGGCGGA     840
TAAAGTTGCA GGACCACTTC TGCGCTCGGC CCTTCCGGCT GGCTGGTTTA TTGCTGATAA     900
ATCTGGAGCC GGTGAGCGTG GGTCTCGCGG TATCATTGCA GCACTGGGGC CAGATGGTAA     960
GCCCTCCCGT ATCGTAGTTA TCTACACGAC GGGGAGTCAG GCAACTATGG ATGAACGAAA    1020
TAGACAGATC GCTGAGATAG GTGCCTCACT GATTAAGCAT TGGTAACTGT CAGACCAAGT    1080
TTACTCATAT ATACTTTAGA TTGATTTAAA ACTTCATTTT TAATTTAAAA GGATCTAGGT    1140
GAAGATCCTT TTTGATAATC TCATGACCAA AATCCCTTAA CGTGAGTTTT CGTTCCACTG    1200
AGCGTCAGAC CCCGTAGAAA AGATCAAAGG ATCTTCTTGA GATCCTTTTT TTCTGCGCGT    1260
AATCTGCTGC TTGCAAACAA AAAAACCACC GCTACCAGCG GTGGTTTGTT TGCCGGATCA    1320
AGAGCTACCA ACTCTTTTTC CGAAGGTAAC TGGCTTCAGC AGAGCGCAGA TACCAAATAC    1380
TGTCCTTCTA GTGTAGCCGT AGTTAGGCCA CCACTTCAAG AACTCTGTAG CACCGCCTAC    1440
ATACCTCGCT CTGCTAATCC TGTTACCAGT GGCTGCTGCC AGTGGCGATA AGTCGTGTCT    1500
TACCGGGTTG GACTCAAGAC GATAGTTACC GGATAAGGCG CAGCGGTCGG GCTGAACGGG    1560
GGGTTCGTGC ACACAGCCCA GCTTGGAGCG AACGACCTAC ACCGAACTGA GATACCTACA    1620
GCGTGAGCAT TGAGAAAGCG CCACGCTTCC CGAAGGGAGA AAGGCGGACA GGTATCCGGT    1680
AAGCGGCAGG GTCGGAACAG GAGAGCGCAC GAGGGAGCTT CCAGGGGGAA ACGCCTGGTA    1740
TCTTTATAGT CCTGTCGGGT TTCGCCACCT CTGACTTGAG CGTCGATTTT TGTGATGCTC    1800
GTCAGGGGGG CGGAGCCTAT GGAAAAACGC CAGCAACGCG GCCTTTTTAC GGTTCCTGGC    1860
CTTTTGCTGG CCTTTTGCTC ACATGTTCTT TCCTGCGTTA TCCCCTGATT CTGTGGATAA    1920
CCGTATTACC GCCTTTGAGT GAGCTGATAC CGCTCGCCGC AGCCGAACGA CCGAGCGCAG    1980
CGAGTCAGTG AGCGAGGAAG CGGAAGAGCG CCTGATGCGG TATTTTCTCC TTACGCATCT    2040
GTGCGGTATT TCACACCGCA TATATGGTGC ACTCTCAGTA CAATCTGCTC TGATGCCGCA    2100
TAGTTAAGCC AGTATACACT CCGCTATCGC TACGTGACTG GGTCATGGCT GCGCCCCGAC    2160
ACCCGCCAAC ACCCGCTGAC GCGCCCTGAC GGGCTTGTCT GCTCCCGGCA TCCGCTTACA    2220
GACAAGCTGT GACCGTCTCC GGGAGCTGCA TGTGTCAGAG GTTTTCACCG TCATCACCGA    2280
AACGCGCGAG GCAGCTGCGG TAAAGCTCAT CAGCGTGGTC GTGAAGCGAT TCACAGATGT    2340
```

```
CTGCCTGTTC ATCCGCGTCC AGCTCGTTGA GTTTCTCCAG AAGCGTTAAT GTCTGGCTTC    2400

TGATAAAGCG GGCCATGTTA AGGGCGGTTT TTTCCTGTTT GGTCACTTGA TGCCTCCGTG    2460

TAAGGGGGAA TTTCTGTTCA TGGGGGTAAT GATACCGATG AAACGAGAGA GGATGCTCAC    2520

GATACGGGTT ACTGATGATG AACATGCCCG GTTACTGGAA CGTTGTGAGG GTAAACAACT    2580

GGCGGTATGG ATGCGGCGGG ACCAGAGAAA AATCACTCAG GGTCAATGCC AGCGCTTCGT    2640

TAATACAGAT GTAGGTGTTC CACAGGGTAG CCAGCAGCAT CCTGCGATGC AGATCCGGAA    2700

CATAATGGTG CAGGGCGCTG ACTTCCGCGT TTCCAGACTT TACGAAACAC GGAAACCGAA    2760

GACCATTCAT GTTGTTGCTC AGGTCGCAGA CGTTTTGCAG CAGCAGTCGC TTCACGTTCG    2820

CTCGCGTATC GGTGATTCAT TCTGCTAACC AGTAAGGCAA CCCCGCCAGC CTAGCCGGGT    2880

CCTCAACGAC AGGAGCACGA TCATGCGCAC CCGTGGCCAG GACCCAACGC TGCCCGAGAT    2940

GCGCCGCGTG CGGCTGCTGG AGATGGCGGA CGCGATGGAT ATGTTCTGCC AAGGGTTGGT    3000

TTGCGCATTC ACAGTTCTCC GCAAGAATTG ATTGGCTCCA ATTCTTGGAG TGGTGAATCC    3060

GTTAGCGAGG TGCCGCCGGC TTCCATTCAG GTCGAGGTGG CCCGGCTCCA TGCACCGCGA    3120

CGCAACGCGG GGAGGCAGAC AAGGTATAGG GCGGCGCCTA CAATCCATGC CAACCCGTTC    3180

CATGTGCTCG CCGAGGCGGC ATAAATCGCC GTGACGATCA GCGGTCCAGT GATCGAAGTT    3240

AGGCTGGTAA GAGCCGCGAG CGATCCTTGA AGCTGTCCCT GATGGTCGTC ATCTACCTGC    3300

CTGGACAGCA TGGCCTGCAA CGCGGGCATC CCGATGCCGC CGGAAGCGAG AAGAATCATA    3360

ATGGGGAAGG CCATCCAGCC TCGCGTCGCG AACGCCAGCA AGACGTAGCC CAGCGCGTCG    3420

GCCGCCATGC CGGCGATAAT GGCCTGCTTC TCGCCGAAAC GTTTGGTGGC GGGACCAGTG    3480

ACGAAGGCTT GAGCGAGGGC GTGCAAGATT CCGAATACCG CAAGCGACAG GCCGATCATC    3540

GTCGCGCTCC AGCGAAAGCG GTCCTCGCCG AAAATGACCC AGAGCGCTGC CGGCACCTGT    3600

CCTACGAGTT GCATGATAAA GAAGACAGTC ATAAGTGCGG CGACGATAGT CATGCCCCGC    3660

GCCCACCGGA AGGAGCTGAC TGGGTTGAAG GCTCTCAAGG GCATCGGTCG ACGCTCTCCC    3720

TTATGCGACT CCTGCATTAG GAAGCAGCCC AGTAGTAGGT TGAGGCCGTT GAGCACCGCC    3780

GCCGCAAGGA ATGGTGCATG CAAGGAGATG CGCCCAACA GTCCCCCGGC ACGGGGCCT    3840

GCCACCATAC CCACGCCGAA ACAAGCGCTC ATGAGCCCGA AGTGGCGAGC CGATCTTCC    3900

CCATCGGTGA TGTCGGCGAT ATAGGCGCCA GCAACCGCAC CTGTGGCGCC GGTGATGCCG    3960

GCCACGATGC GTCCGGCGTA GAGGATCGAG ATCTCGATCC CGCGAAATTA ATACGACTCA    4020

CTATAGGGAG ACCACAACGG TTTCCCTCTA GAAATAATTT TGTTTAACTT TAAGAAGGAG    4080

ATATATATGG AACCGGTCGT TTCTCTGTCG GGCCCGGCGG ACAGCGGCGA CGCCCTGCTG    4140

GAGCGCAACT ATCCCACTGG CGCGGAGTTC CTCGGCGACG GCGGCGACGT CAGCTTCAGC    4200

ACCCGCGGCA CGCAGAACTG GACGGTGGAG CGGCTGCTCC AGGCGCACCG CCAACTGGAG    4260

GAGCGCGGCT ATGTGTTCGT CGGCTACCAC GGCACCTTCC TCGAAGCGGC GCAAAGCATC    4320

GTCTTCGGCG GGGTGCGCGC GCGCAGCCAG GACCTCGACG CGATCTGGCG CGGTTTCTAT    4380

ATCGCCGGCG ATCCGGCGCT GGCCTACGGC TACGCCCAGG ACCAGGAACC CGACGCACGC    4440

GGCCGGATCC GCAACGGTGC CCTGCTGCGG GTCTATGTGC CGCGCTCGAG CCTGCCGGGC    4500

TTCTACCGCA CCAGCCTGAC CCTGGCCGCG CCGGAGGCGG CGGGCGAGGT CGAACGGCTG    4560

ATCGGCCATC CGCTGCCGCT GCGCCTGGAC GCCATCACCG CCCCGAGGA GGAAGGCGGG    4620

CGCCTGGAGA CCATTCTCGG CTGGCCGCTG GCCGAGCGCA CCGTGGTGAT TCCCTCGGCG    4680

ATCCCCACCG ACCCGCGCAA CGTCGGCGGC GACCTCGACC CGTCCAGCAT CCCCGACAAG    4740
```

```
GAACAGGCGA TCAGCGCCCT GCCGGACTAC GCCAGCCAGC CCGGCAAACC GCCGCGCGAG   4800

GACCTGAAGT AACTGCCGCG ACCGGCCGGC TCCCTTCGCA GGAGCCGGCC TTCTCGGGGC   4860

CTGGCCATAC ATCAGGTTTT CCTGATGCCA GCCCAATCGA ATATGAATTC              4910
```

(2) INFORMATION FOR SEQ ID NO:12:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:12:

```
TATGGAACCG GTCGTTTCTC TGTCGGGCC                                       29
```

(2) INFORMATION FOR SEQ ID NO:13:

(i) SEQUENCE CHARACTERISTICS:
        (A) LENGTH: 23 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:13:

```
CGACAGAGAA ACGACCGGTT CCA                                             23
```

(2) INFORMATION FOR SEQ ID NO:14:

(i) SEQUENCE CHARACTERISTICS:
        (A) LENGTH: 4977 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:14:

```
TTCTTGAAGA CGAAAGGGCC TCGTGATACG CCTATTTTTA TAGGTTAATG TCATGATAAT     60

AATGGTTTCT TAGACGTCAG GTGGCACTTT TCGGGGAAAT GTGCGCGGAA CCCCTATTTG    120

TTTATTTTTC TAAATACATT CAAATATGTA TCCGCTCATG AGACAATAAC CCTGATAAAT    180

GCTTCAATAA TATTGAAAAA GGAAGAGTAT GAGTATTCAA CATTTCCGTG TCGCCCTTAT    240

TCCCTTTTTT GCGGCATTTT GCCTTCCTGT TTTTGCTCAC CCAGAAACGC TGGTGAAAGT    300

AAAAGATGCT GAAGATCAGT TGGGTGCACG AGTGGGTTAC ATCGAACTGG ATCTCAACAG    360

CGGTAAGATC CTTGAGAGTT TTCGCCCCGA AGAACGTTTT CCAATGATGA GCACTTTTAA    420

AGTTCTGCTA TGTGGCGCGG TATTATCCCG TGTTGACGCC GGGCAAGAGC AACTCGGTCG    480

CCGCATACAC TATTCTCAGA ATGACTTGGT TGAGTACTCA CCAGTCACAG AAAAGCATCT    540

TACGGATGGC ATGACAGTAA GAGAATTATG CAGTGCTGCC ATAACCATGA GTGATAACAC    600

TGCGGCCAAC TTACTTCTGA CAACGATCGG AGGACCGAAG GAGCTAACCG CTTTTTTGCA    660

CAACATGGGG GATCATGTAA CTCGCCTTGA TCGTTGGGAA CCGGAGCTGA ATGAAGCCAT    720

ACCAAACGAC GAGCGTGACA CCACGATGCC TGCAGCAATG GCAACAACGT TGCGCAAACT    780

ATTAACTGGC GAACTACTTA CTCTAGCTTC CCGGCAACAA TTAATAGACT GGATGGAGGC    840

GGATAAAGTT GCAGGACCAC TTCTGCGCTC GGCCCTTCCG GCTGGCTGGT TTATTGCTGA    900
```

```
TAAATCTGGA GCCGGTGAGC GTGGGTCTCG CGGTATCATT GCAGCACTGG GGCCAGATGG    960

TAAGCCCTCC CGTATCGTAG TTATCTACAC GACGGGGAGT CAGGCAACTA TGGATGAACG   1020

AAATAGACAG ATCGCTGAGA TAGGTGCCTC ACTGATTAAG CATTGGTAAC TGTCAGACCA   1080

AGTTTACTCA TATATACTTT AGATTGATTT AAAACTTCAT TTTTAATTTA AAAGGATCTA   1140

GGTGAAGATC CTTTTTGATA ATCTCATGAC CAAAATCCCT TAACGTGAGT TTTCGTTCCA   1200

CTGAGCGTCA GACCCCGTAG AAAAGATCAA AGGATCTTCT TGAGATCCTT TTTTTCTGCG   1260

CGTAATCTGC TGCTTGCAAA CAAAAAAACC ACCGCTACCA GCGGTGGTTT GTTTGCCGGA   1320

TCAAGAGCTA CCAACTCTTT TTCCGAAGGT AACTGGCTTC AGCAGAGCGC AGATACCAAA   1380

TACTGTCCTT CTAGTGTAGC CGTAGTTAGG CCACCACTTC AAGAACTCTG TAGCACCGCC   1440

TACATACCTC GCTCTGCTAA TCCTGTTACC AGTGGCTGCT GCCAGTGGCG ATAAGTCGTG   1500

TCTTACCGGG TTGGACTCAA GACGATAGTT ACCGGATAAG GCGCAGCGGT CGGGCTGAAC   1560

GGGGGGTTCG TGCACACAGC CCAGCTTGGA GCGAACGACC TACACCGAAC TGAGATACCT   1620

ACAGCGTGAG CATTGAGAAA GCGCCACGCT TCCCGAAGGG AGAAAGGCGG ACAGGTATCC   1680

GGTAAGCGGC AGGGTCGGAA CAGGAGAGCG CACGAGGGAG CTTCCAGGGG GAAACGCCTG   1740

GTATCTTTAT AGTCCTGTCG GGTTTCGCCA CCTCTGACTT GAGCGTCGAT TTTTGTGATG   1800

CTCGTCAGGG GGGCGGAGCC TATGGAAAAA CGCCAGCAAC GCGGCCTTTT TACGGTTCCT   1860

GGCCTTTTGC TGGCCTTTTG CTCACATGTT CTTTCCTGCG TTATCCCCTG ATTCTGTGGA   1920

TAACCGTATT ACCGCCTTTG AGTGAGCTGA TACCGCTCGC CGCAGCCGAA CGACCGAGCG   1980

CAGCGAGTCA GTGAGCGAGG AAGCGGAAGA GCGCCTGATG CGGTATTTTC TCCTTACGCA   2040

TCTGTGCGGT ATTTCACACC GCATATATGG TGCACTCTCA GTACAATCTG CTCTGATGCC   2100

GCATAGTTAA GCCAGTATAC ACTCCGCTAT CGCTACGTGA CTGGGTCATG GCTGCGCCCC   2160

GACACCCGCC AACACCCGCT GACGCGCCCT GACGGGCTTG TCTGCTCCCG GCATCCGCTT   2220

ACAGACAAGC TGTGACCGTC TCCGGGAGCT GCATGTGTCA GAGGTTTTCA CCGTCATCAC   2280

CGAAACGCGC GAGGCAGCTG CGGTAAAGCT CATCAGCGTG GTCGTGAAGC GATTCACAGA   2340

TGTCTGCCTG TTCATCCGCG TCCAGCTCGT TGAGTTTCTC CAGAAGCGTT AATGTCTGGC   2400

TTCTGATAAA GCGGGCCATG TTAAGGGCGG TTTTTTCCTG TTTGGTCACT TGATGCCTCC   2460

GTGTAAGGGG GAATTTCTGT TCATGGGGGT AATGATACCG ATGAAACGAG AGAGGATGCT   2520

CACGATACGG GTTACTGATG ATGAACATGC CCGGTTACTG GAACGTTGTG AGGGTAAACA   2580

ACTGGCGGTA TGGATGCGGC GGGACCAGAG AAAAATCACT CAGGGTCAAT GCCAGCGCTT   2640

CGTTAATACA GATGTAGGTG TTCCACAGGG TAGCCAGCAG CATCCTGCGA TGCAGATCCG   2700

GAACATAATG GTGCAGGGCG CTGACTTCCG CGTTTCCAGA CTTTACGAAA CACGGAAACC   2760

GAAGACCATT CATGTTGTTG CTCAGGTCGC AGACGTTTTG CAGCAGCAGT CGCTTCACGT   2820

TCGCTCGCGT ATCGGTGATT CATTCTGCTA ACCAGTAAGG CAACCCCGCC AGCCTAGCCG   2880

GGTCCTCAAC GACAGGAGCA CGATCATGCG CACCCGTGGC CAGGACCCAA CGCTGCCCGA   2940

GATGCGCCGC GTGCGGCTGC TGGAGATGGC GGACGCGATG GATATGTTCT GCCAAGGGTT   3000

GGTTTGCGCA TTCACAGTTC TCCGCAAGAA TTGATTGGCT CCAATTCTTG GAGTGGTGAA   3060

TCCGTTAGCG AGGTGCCGCC GGCTTCCATT CAGGTCGAGG TGGCCCGGCT CCATGCACCG   3120

CGACGCAACG CGGGGAGGCA GACAAGGTAT AGGGCGGCGC CTACAATCCA TGCCAACCCG   3180

TTCCATGTGC TCGCCGAGGC GGCATAAATC GCCGTGACGA TCAGCGGTCC AGTGATCGAA   3240
```

```
GTTAGGCTGG TAAGAGCCGC GAGCGATCCT TGAAGCTGTC CCTGATGGTC GTCATCTACC    3300

TGCCTGGACA GCATGGCCTG CAACGCGGGC ATCCCGATGC CGCCGGAAGC GAGAAGAATC    3360

ATAATGGGGA AGGCCATCCA GCCTCGCGTC GCGAACGCCA GCAAGACGTA GCCCAGCGCG    3420

TCGGCCGCCA TGCCGGCGAT AATGGCCTGC TTCTCGCCGA AACGTTTGGT GGCGGGACCA    3480

GTGACGAAGG CTTGAGCGAG GGCGTGCAAG ATTCCGAATA CCGCAAGCGA CAGGCCGATC    3540

ATCGTCGCGC TCCAGCGAAA GCGGTCCTCG CCGAAAATGA CCCAGAGCGC TGCCGGCACC    3600

TGTCCTACGA GTTGCATGAT AAAGAAGACA GTCATAAGTG CGGCGACGAT AGTCATGCCC    3660

CGCGCCCACC GGAAGGAGCT GACTGGGTTG AAGGCTCTCA AGGGCATCGG TCGACGCTCT    3720

CCCTTATGCG ACTCCTGCAT TAGGAAGCAG CCCAGTAGTA GGTTGAGGCC GTTGAGCACC    3780

GCCGCCGCAA GGAATGGTGC ATGCAAGGAG ATGGCGCCCA ACAGTCCCCC GGCCACGGGG    3840

CCTGCCACCA TACCCACGCC GAAACAAGCG CTCATGAGCC CGAAGTGGCG AGCCCGATCT    3900

TCCCCATCGG TGATGTCGGC GATATAGGCG CCAGCAACCG CACCTGTGGC GCCGGTGATG    3960

CCGGCCACGA TGCGTCCGGC GTAGAGGATC GAGATCTCGA TCCCGCGAAA TTAATACGAC    4020

TCACTATAGG GAGACCACAA CGGTTTCCCT CTAGAAATAA TTTTGTTTAA CTTTAAGAAG    4080

GAGATATACC ATGGTACCAG ACACCGGAAA CCCCTGCCAC ACCACTAAGT TGTTGCACAG    4140

AGACTCAGTG GACAGTGCTC CAATCCTCAC TGCATTTAAC AGCTCACACA AAGGACGGAT    4200

TAACTGTAAT AGTAACACTA CACCCATAGT ACATTTAAAA GGTGATGCTA ATACTTTAAA    4260

ATGTTTAAGA TATAGATTTA AAAAGCATTG TACATTGTAT ACTGCAGTGT CGTCTACATG    4320

GCATTGGACA GGACATAATG TAAAACATAA AAGTGCAATT GTTACACTTA CATATGATAG    4380

TGAATGGCAA CGTGACCAAT TTTTGTCTCA AGTTAAAATA CCAAAAACTA TTACAGTGTC    4440

TACTGGATTT ATGTCTATAT GAGGATCCGG CTGCTAACAA AGCCCGAAAG GAAGCTGAGT    4500

TGGCTGCTGC CACCGCTGAG CAATAACTAG CATAACCCCT TGGGGCCTCT AAACGGGTCT    4560

TGAGGGGTTT TTTGCTGAAA GGAGGAACTA TATCCGGATA TCCACAGGAC GGGTGTGGTC    4620

GCCATGATCG CGTAGTCGAT AGTGGCTCCA AGTAGCGAAG CGAGCAGGAC TGGGCGGCGG    4680

CCAAAGCGGT CGGACAGTGC TCCGAGAACG GGTGCGCATA GAAATTGCAT CAACGCATAT    4740

AGCGCTAGCA GCACGCCATA GTGACTGGCG ATGCTGTCGG AATGGACGAT ATCCCGCAAG    4800

AGGCCCGGCA GTACCGGCAT AACCAAGCCT ATGCCTACAG CATCCAGGGT GACGGTGCCG    4860

AGGATGACGA TGAGCGCATT GTTAGATTTC ATACACGGTG CCTGACTGCG TTAGCAATTT    4920

AACTGTGATA AACTACCGCA TTAAAGCTTA TCGATGATAA GCTGTCAAAC ATGAGAA      4977
```

(2) INFORMATION FOR SEQ ID NO:15:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:15:

```
CTCCCATGGT ACCAGACACC GGAAACC                                         27
```

(2) INFORMATION FOR SEQ ID NO:16:

(i) SEQUENCE CHARACTERISTICS:
        (A) LENGTH: 27 base pairs
        (B) TYPE: nucleic acid (C) STRANDEDNESS: single
        (D) TOPOLOGY: linear (ii) MOLECULE TYPE: DNA (genomic)

(xi) SEQUENCE DESCRIPTION: SEQ ID NO:16:

GGGGGATCCT CATATAGACA TAAATCC                                          27

(2) INFORMATION FOR SEQ ID NO:17:

(i) SEQUENCE CHARACTERISTICS:
        (A) LENGTH: 4977 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:17:

TTCTTGAAGA CGAAAGGGCC TCGTGATACG CCTATTTTTA TAGGTTAATG TCATGATAAT        60

AATGGTTTCT TAGACGTCAG GTGGCACTTT TCGGGGAAAT GTGCGCGGAA CCCCTATTTG       120

TTTATTTTTC TAAATACATT CAAATATGTA TCCGCTCATG AGACAATAAC CCTGATAAAT      180

GCTTCAATAA TATTGAAAAA GGAAGAGTAT GAGTATTCAA CATTTCCGTG TCGCCCTTAT       240

TCCCTTTTTT GCGGCATTTT GCCTTCCTGT TTTTGCTCAC CCAGAAACGC TGGTGAAAGT       300

AAAAGATGCT GAAGATCAGT TGGGTGCACG AGTGGGTTAC ATCGAACTGG ATCTCAACAG       360

CGGTAAGATC CTTGAGAGTT TTCGCCCCGA AGAACGTTTT CCAATGATGA GCACTTTTAA       420

AGTTCTGCTA TGTGGCGCGG TATTATCCCG TGTTGACGCC GGGCAAGAGC AACTCGGTCG       480

CCGCATACAC TATTCTCAGA ATGACTTGGT TGAGTACTCA CCAGTCACAG AAAAGCATCT       540

TACGGATGGC ATGACAGTAA GAGAATTATG CAGTGCTGCC ATAACCATGA GTGATAACAC       600

TGCGGCCAAC TTACTTCTGA CAACGATCGG AGGACCGAAG GAGCTAACCG CTTTTTTGCA       660

CAACATGGGG GATCATGTAA CTCGCCTTGA TCGTTGGGAA CCGGAGCTGA ATGAAGCCAT       720

ACCAAACGAC GAGCGTGACA CCACGATGCC TGCAGCAATG GCAACAACGT TGCGCAAACT       780

ATTAACTGGC GAACTACTTA CTCTAGCTTC CCGGCAACAA TTAATAGACT GGATGGAGGC       840

GGATAAAGTT GCAGGACCAC TTCTGCGCTC GGCCCTTCCG GCTGGCTGGT TTATTGCTGA       900

TAAATCTGGA GCCGGTGAGC GTGGGTCTCG CGGTATCATT GCAGCACTGG GGCCAGATGG       960

TAAGCCCTCC CGTATCGTAG TTATCTACAC GACGGGGAGT CAGGCAACTA TGGATGAACG      1020

AAATAGACAG ATCGCTGAGA TAGGTGCCTC ACTGATTAAG CATTGGTAAC TGTCAGACCA      1080

AGTTTACTCA TATATACTTT AGATTGATTT AAAACTTCAT TTTTAATTTA AAAGGATCTA      1140

GGTGAAGATC CTTTTTGATA ATCTCATGAC CAAAATCCCT TAACGTGAGT TTTCGTTCCA      1200

CTGAGCGTCA GACCCCGTAG AAAAGATCAA AGGATCTTCT TGAGATCCTT TTTTTCTGCG      1260

CGTAATCTGC TGCTTGCAAA CAAAAAAACC ACCGCTACCA GCGGTGGTTT GTTTGCCGGA      1320

TCAAGAGCTA CCAACTCTTT TTCCGAAGGT AACTGGCTTC AGCAGAGCGC AGATACCAAA      1380

TACTGTCCTT CTAGTGTAGC CGTAGTTAGG CCACCACTTC AAGAACTCTG TAGCACCGCC      1440

TACATACCTC GCTCTGCTAA TCCTGTTACC AGTGGCTGCT GCCAGTGGCG ATAAGTCGTG      1500

TCTTACCGGG TTGGACTCAA GACGATAGTT ACCGGATAAG GCGCAGCGGT CGGGCTGAAC      1560

GGGGGGTTCG TGCACACAGC CCAGCTTGGA GCGAACGACC TACACCGAAC TGAGATACCT      1620

ACAGCGTGAG CATTGAGAAA GCGCCACGCT TCCCGAAGGG AGAAAGGCGG ACAGGTATCC      1680

GGTAAGCGGC AGGGTCGGAA CAGGAGAGCG CACGAGGGAG CTTCCAGGGG GAAACGCCTG      1740

```
GTATCTTTAT AGTCCTGTCG GGTTTCGCCA CCTCTGACTT GAGCGTCGAT TTTTGTGATG      1800

CTCGTCAGGG GGGCGGAGCC TATGGAAAAA CGCCAGCAAC GCGGCCTTTT TACGGTTCCT      1860

GGCCTTTTGC TGGCCTTTTG CTCACATGTT CTTTCCTGCG TTATCCCCTG ATTCTGTGGA      1920

TAACCGTATT ACCGCTTTG AGTGAGCTGA TACCGCTCGC CGCAGCCGAA CGACCGAGCG       1980

CAGCGAGTCA GTGAGCGAGG AAGCGGAAGA GCGCCTGATG CGGTATTTTC TCCTTACGCA      2040

TCTGTGCGGT ATTTCACACC GCATATATGG TGCACTCTCA GTACAATCTG CTCTGATGCC     2100

GCATAGTTAA GCCAGTATAC ACTCCGCTAT CGCTACGTGA CTGGGTCATG GCTGCGCCCC     2160

GACACCCGCC AACACCCGCT GACGCGCCCT GACGGGCTTG TCTGCTCCCG GCATCCGCTT     2220

ACAGACAAGC TGTGACCGTC TCCGGGAGCT GCATGTGTCA GAGGTTTTCA CCGTCATCAC     2280

CGAAACGCGC GAGGCAGCTG CGGTAAAGCT CATCAGCGTG GTCGTGAAGC GATTCACAGA     2340

TGTCTGCCTG TTCATCCGCG TCCAGCTCGT TGAGTTTCTC CAGAAGCGTT AATGTCTGGC     2400

TTCTGATAAA GCGGGCCATG TTAAGGGCGG TTTTTTCCTG TTTGGTCACT TGATGCCTCC     2460

GTGTAAGGGG AATTTCTGT TCATGGGGGT AATGATACCG ATGAAACGAG AGAGGATGCT     2520

CACGATACGG GTTACTGATG ATGAACATGC CCGGTTACTG AACGTTGTG AGGGTAAACA     2580

ACTGGCGGTA TGGATGCGGC GGGACCAGAG AAAAATCACT CAGGGTCAAT GCCAGCGCTT     2640

CGTTAATACA GATGTAGGTG TTCCACAGGG TAGCCAGCAG CATCCTGCGA TGCAGATCCG     2700

GAACATAATG GTGCAGGGCG CTGACTTCCG CGTTTCCAGA CTTTACGAAA CACGGAAACC     2760

GAAGACCATT CATGTTGTTG CTCAGGTCGC AGACGTTTTG CAGCAGCAGT CGCTTCACGT     2820

TCGCTCGCGT ATCGGTGATT CATTCTGCTA ACCAGTAAGG CAACCCCGCC AGCCTAGCCG     2880

GGTCCTCAAC GACAGGAGCA CGATCATGCG CACCCGTGGC CAGGACCCAA CGCTGCCCGA     2940

GATGCGCCGC GTGCGGCTGC TGGAGATGGC GGACGCGATG GATATGTTCT GCCAAGGGTT     3000

GGTTTGCGCA TTCACAGTTC TCCGCAAGAA TTGATTGGCT CCAATTCTTG GAGTGGTGAA     3060

TCCGTTAGCG AGGTGCCGCC GGCTTCCATT CAGGTCGAGG TGGCCCGGCT CCATGCACCG     3120

CGACGCAACG CGGGGAGGCA GACAAGGTAT AGGGCGGCGC CTACAATCCA TGCCAACCCG     3180

TTCCATGTGC TCGCCGAGGC GGCATAAATC GCCGTGACGA TCAGCGGTCC AGTGATCGAA     3240

GTTAGGCTGG TAAGAGCCGC GAGCGATCCT TGAAGCTGTC CCTGATGGTC GTCATCTACC     3300

TGCCTGGACA GCATGGCCTG CAACGCGGGC ATCCCGATGC CGCCGGAAGC GAGAAGAATC     3360

ATAATGGGA AGGCCATCCA GCCTCGCGTC GCGAACGCCA GCAAGACGTA GCCCAGCGCG     3420

TCGGCCGCCA TGCCGGCGAT AATGGCCTGC TTCTCGCCGA AACGTTTGGT GGCGGGACCA    3480

GTGACGAAGG CTTGAGCGAG GGCGTGCAAG ATTCCGAATA CCGCAAGCGA CAGGCCGATC    3540

ATCGTCGCGC TCCAGCGAAA GCGGTCCTCG CCGAAAATGA CCCAGAGCGC TGCCGGCACC    3600

TGTCCTACGA GTTGCATGAT AAAGAAGACA GTCATAAGTG CGGCGACGAT AGTCATGCCC    3660

CGCGCCCACC GGAAGGAGCT GACTGGGTTG AAGGCTCTCA AGGGCATCGG TCGACGCTCT    3720

CCCTTATGCG ACTCCTGCAT TAGGAAGCAG CCCAGTAGTA GGTTGAGGCC GTTGAGCACC    3780

GCCGCCGCAA GGAATGGTGC ATGCAAGGAG ATGGCGCCCA ACAGTCCCCC GGCCACGGGG    3840

CCTGCCACCA TACCCACGCC GAAACAAGCG CTCATGAGCC CGAAGTGGCG AGCCCGATCT    3900

TCCCCATCGG TGATGTCGGC GATATAGGCG CCAGCAACCG CACCTGTGGC GCCGGTGATG    3960

CCGGCCACGA TGCGTCCGGC GTAGAGGATC GAGATCTCGA TCCCGCGAAA TTAATACGAC    4020

TCACTATAGG GAGACCACAA CGGTTTCCCT CTAGAAATAA TTTTGTTTAA CTTTAAGAAG    4080
```

-continued

| | | | | |
|---|---|---|---|---|
| GAGATATACC | ATGGTACCAG | ACACCGGAAA | CCCCTGCCAC | ACCACTAAGT TGTTGCACAG | 4140 |
| AGACTCAGTG | GACAGTGCTC | CAATCCTCAC | TGCATTTAAC | AGCTCACACA AAGGACGGAT | 4200 |
| TAACTGTAAT | AGTAACACTA | CACCCATAGT | ACATTTAAAA | GGTGATGCTA ATACTTTAAG | 4260 |
| ATCTTTAAGA | TATAGATTTA | AAAAGCATTC | TACATTGTAT | ACTGCAGTGT CGTCTACATG | 4320 |
| GCATTGGACA | GGACATAATG | TAAAACATAA | AAGTGCAATT | GTTACACTTA CATATGATAG | 4380 |
| TGAATGGCAA | CGTGACCAAT | TTTTGTCTCA | AGTTAAAATA | CCAAAAACTA TTACAGTGTC | 4440 |
| TACTGGATTT | ATGTCTATAT | GAGGATCCGG | CTGCTAACAA | AGCCCGAAAG GAAGCTGAGT | 4500 |
| TGGCTGCTGC | CACCGCTGAG | CAATAACTAG | CATAACCCCT | TGGGGCCTCT AAACGGGTCT | 4560 |
| TGAGGGGTTT | TTTGCTGAAA | GGAGGAACTA | TATCCGGATA | TCCACAGGAC GGGTGTGGTC | 4620 |
| GCCATGATCG | CGTAGTCGAT | AGTGGCTCCA | AGTAGCGAAG | CGAGCAGGAC TGGGCGGCGG | 4680 |
| CCAAAGCGGT | CGGACAGTGC | TCCGAGAACG | GGTGCGCATA | GAAATTGCAT CAACGCATAT | 4740 |
| AGCGCTAGCA | GCACGCCATA | GTGACTGGCG | ATGCTGTCGG | AATGGACGAT ATCCCGCAAG | 4800 |
| AGGCCCGGCA | GTACCGGCAT | AACCAAGCCT | ATGCCTACAG | CATCCAGGGT GACGGTGCCG | 4860 |
| AGGATGACGA | TGAGCGCATT | GTTAGATTTC | ATACACGGTG | CCTGACTGCG TTAGCAATTT | 4920 |
| AACTGTGATA | AACTACCGCA | TTAAAGCTTA | TCGATGATAA | GCTGTCAAAC ATGAGAA | 4977 |

(2) INFORMATION FOR SEQ ID NO:18:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:18:

CGACACTGCA GTATACAATG TAGAATGCTT TTTAAATCTA TATCTTAAAG ATCTTAAAG     59

(2) INFORMATION FOR SEQ ID NO:19:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:19:

GCGTCGGCCG CCATGCCGGC GATAAT     26

(2) INFORMATION FOR SEQ ID NO:20:

(i) SEQUENCE CHARACTERISTICS:
        (A) LENGTH: 4819 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:20:

| | | | | |
|---|---|---|---|---|
| TTCTTGAAGA | CGAAAGGGCC | TCGTGATACG | CCTATTTTTA | TAGGTTAATG TCATGATAAT | 60 |
| AATGGTTTCT | TAGACGTCAG | GTGGCACTTT | TCGGGGAAAT | GTGCGCGGAA CCCCTATTTG | 120 |
| TTTATTTTTC | TAAATACATT | CAAATATGTA | TCCGCTCATG | AGACAATAAC CCTGATAAAT | 180 |

-continued

```
GCTTCAATAA TATTGAAAAA GGAAGAGTAT GAGTATTCAA CATTTCCGTG TCGCCCTTAT    240

TCCCTTTTTT GCGGCATTTT GCCTTCCTGT TTTTGCTCAC CCAGAAACGC TGGTGAAAGT    300

AAAAGATGCT GAAGATCAGT TGGGTGCACG AGTGGGTTAC ATCGAACTGG ATCTCAACAG    360

CGGTAAGATC CTTGAGAGTT TTCGCCCCGA AGAACGTTTT CCAATGATGA GCACTTTTAA    420

AGTTCTGCTA TGTGGCGCGG TATTATCCCG TGTTGACGCC GGGCAAGAGC AACTCGGTCG    480

CCGCATACAC TATTCTCAGA ATGACTTGGT TGAGTACTCA CCAGTCACAG AAAAGCATCT    540

TACGGATGGC ATGACAGTAA GAGAATTATG CAGTGCTGCC ATAACCATGA GTGATAACAC    600

TGCGGCCAAC TTACTTCTGA CAACGATCGG AGGACCGAAG GAGCTAACCG CTTTTTTGCA    660

CAACATGGGG GATCATGTAA CTCGCCTTGA TCGTTGGGAA CCGGAGCTGA ATGAAGCCAT    720

ACCAAACGAC GAGCGTGACA CCACGATGCC TGCAGCAATG GCAACAACGT TGCGCAAACT    780

ATTAACTGGC GAACTACTTA CTCTAGCTTC CCGGCAACAA TTAATAGACT GGATGGAGGC    840

GGATAAAGTT GCAGGACCAC TTCTGCGCTC GGCCCTTCCG GCTGGCTGGT TTATTGCTGA    900

TAAATCTGGA GCCGGTGAGC GTGGGTCTCG CGGTATCATT GCAGCACTGG GGCCAGATGG    960

TAAGCCCTCC CGTATCGTAG TTATCTACAC GACGGGGAGT CAGGCAACTA TGGATGAACG   1020

AAATAGACAG ATCGCTGAGA TAGGTGCCTC ACTGATTAAG CATTGGTAAC TGTCAGACCA   1080

AGTTTACTCA TATATACTTT AGATTGATTT AAAACTTCAT TTTTAATTTA AAAGGATCTA   1140

GGTGAAGATC CTTTTTGATA ATCTCATGAC CAAAATCCCT TAACGTGAGT TTTCGTTCCA   1200

CTGAGCGTCA GACCCCGTAG AAAAGATCAA AGGATCTTCT TGAGATCCTT TTTTTCTGCG   1260

CGTAATCTGC TGCTTGCAAA CAAAAAAACC ACCGCTACCA GCGGTGGTTT GTTTGCCGGA   1320

TCAAGAGCTA CCAACTCTTT TTCCGAAGGT AACTGGCTTC AGCAGAGCGC AGATACCAAA   1380

TACTGTCCTT CTAGTGTAGC CGTAGTTAGG CCACCACTTC AAGAACTCTG TAGCACCGCC   1440

TACATACCTC GCTCTGCTAA TCCTGTTACC AGTGGCTGCT GCCAGTGGCG ATAAGTCGTG   1500

TCTTACCGGG TTGGACTCAA GACGATAGTT ACCGGATAAG GCGCAGCGGT CGGGCTGAAC   1560

GGGGGGTTCG TGCACACAGC CCAGCTTGGA GCGAACGACC TACACCGAAC TGAGATACCT   1620

ACAGCGTGAG CATTGAGAAA GCGCCACGCT TCCCGAAGGG AGAAAGGCGG ACAGGTATCC   1680

GGTAAGCGGC AGGGTCGGAA CAGGAGAGCG CACGAGGGAG CTTCCAGGGG GAAACGCCTG   1740

GTATCTTTAT AGTCCTGTCG GGTTTCGCCA CCTCTGACTT GAGCGTCGAT TTTTGTGATG   1800

CTCGTCAGGG GGGCGGAGCC TATGGAAAAA CGCCAGCAAC GCGGCCTTTT TACGGTTCCT   1860

GGCCTTTTGC TGGCCTTTTG CTCACATGTT CTTTCCTGCG TTATCCCCTG ATTCTGTGGA   1920

TAACCGTATT ACCGCCTTTG AGTGAGCTGA TACCGCTCGC CGCAGCCGAA CGACCGAGCG   1980

CAGCGAGTCA GTGAGCGAGG AAGCGGAAGA GCGCCTGATG CGGTATTTTC TCCTTACGCA   2040

TCTGTGCGGT ATTTCACACC GCATATATGG TGCACTCTCA GTACAATCTG CTCTGATGCC   2100

GCATAGTTAA GCCAGTATAC ACTCCGCTAT CGCTACGTGA CTGGGTCATG GCTGCGCCCC   2160

GACACCCGCC AACACCCGCT GACGCGCCCT GACGGGCTTG TCTGCTCCCG GCATCCGCTT   2220

ACAGACAAGC TGTGACCGTC TCCGGGAGCT GCATGTGTCA GAGGTTTTCA CCGTCATCAC   2280

CGAAACGCGC GAGGCAGCTG CGGTAAAGCT CATCAGCGTG GTCGTGAAGC GATTCACAGA   2340

TGTCTGCCTG TTCATCCGCG TCCAGCTCGT TGAGTTTCTC CAGAAGCGTT AATGTCTGGC   2400

TTCTGATAAA GCGGGCCATG TTAAGGGCGG TTTTTTCCTG TTTGGTCACT TGATGCCTCC   2460

GTGTAAGGGG GAATTTCTGT TCATGGGGGT AATGATACCG ATGAAACGAG AGAGGATGCT   2520

CACGATACGG GTTACTGATG ATGAACATGC CCGGTTACTG GAACGTTGTG AGGGTAAACA   2580
```

-continued

```
ACTGGCGGTA TGGATGCGGC GGGACCAGAG AAAAATCACT CAGGGTCAAT GCCAGCGCTT    2640

CGTTAATACA GATGTAGGTG TTCCACAGGG TAGCCAGCAG CATCCTGCGA TGCAGATCCG    2700

GAACATAATG GTGCAGGGCG CTGACTTCCG CGTTTCCAGA CTTTACGAAA CACGGAAACC    2760

GAAGACCATT CATGTTGTTG CTCAGGTCGC AGACGTTTTG CAGCAGCAGT CGCTTCACGT    2820

TCGCTCGCGT ATCGGTGATT CATTCTGCTA ACCAGTAAGG CAACCCCGCC AGCCTAGCCG    2880

GGTCCTCAAC GACAGGAGCA CGATCATGCG CACCCGTGGC CAGGACCCAA CGCTGCCCGA    2940

GATGCGCCGC GTGCGGCTGC TGGAGATGGC GGACGCGATG GATATGTTCT GCCAAGGGTT    3000

GGTTTGCGCA TTCACAGTTC TCCGCAAGAA TTGATTGGCT CCAATTCTTG GAGTGGTGAA    3060

TCCGTTAGCG AGGTGCCGCC GGCTTCCATT CAGGTCGAGG TGGCCCGGCT CCATGCACCG    3120

CGACGCAACG CGGGGAGGCA GACAAGGTAT AGGGCGGCGC CTACAATCCA TGCCAACCCG    3180

TTCCATGTGC TCGCCGAGGC GGCATAAATC GCCGTGACGA TCAGCGGTCC AGTGATCGAA    3240

GTTAGGCTGG TAAGAGCCGC GAGCGATCCT TGAAGCTGTC CCTGATGGTC GTCATCTACC    3300

TGCCTGGACA GCATGGCCTG CAACGCGGGC ATCCCGATGC CGCCGGAAGC GAGAAGAATC    3360

ATAATGGGGA AGGCCATCCA GCCTCGCGTC GCGAACGCCA GCAAGACGTA GCCCAGCGCG    3420

TCGGCCGCCA TGCCGGCGAT AATGGCCTGC TTCTCGCCGA AACGTTTGGT GGCGGGACCA    3480

GTGACGAAGG CTTGAGCGAG GGCGTGCAAG ATTCCGAATA CCGCAAGCGA CAGGCCGATC    3540

ATCGTCGCGC TCCAGCGAAA GCGGTCCTCG CCGAAAATGA CCCAGAGCGC TGCCGGCACC    3600

TGTCCTACGA GTTGCATGAT AAAGAAGACA GTCATAAGTG CGGCGACGAT AGTCATGCCC    3660

CGCGCCCACC GGAAGGAGCT GACTGGGTTG AAGGCTCTCA AGGGCATCGG TCGACGCTCT    3720

CCCTTATGCG ACTCCTGCAT TAGGAAGCAG CCCAGTAGTA GGTTGAGGCC GTTGAGCACC    3780

GCCGCCGCAA GGAATGGTGC ATGCAAGGAG ATGGCGCCCA ACAGTCCCCC GGCCACGGGG    3840

CCTGCCACCA TACCCACGCC GAAACAAGCG CTCATGAGCC CGAAGTGGCG AGCCCGATCT    3900

TCCCCATCGG TGATGTCGGC GATATAGGCG CCAGCAACCG CACCTGTGGC GCCGGTGATG    3960

CCGGCCACGA TGCGTCCGGC GTAGAGGATC GAGATCTCGA TCCCGCGAAA TTAATACGAC    4020

TCACTATAGG GAGACCACAA CGGTTTCCCT CTAGAAATAA TTTTGTTTAA CTTTAAGAAG    4080

GAGATATACA TATGGAACCG GTCGACCCGC GTCTGGAACC ATGGAAACAC CCCGGGTCCC    4140

AGCCGAAAAC CGCGTTCATC ACCAAAGCCC TAGGTATCTC TTACGGCCGT AAAAAACGTC    4200

GTCAGCGACG TCGTCCGCCG CAGGGATCCC AGACCCACCA GGTTTCTCTG TCTAAACAGT    4260

GATCAGCATT GGCTAGCATG ACTGGTGGAC AGCAAATGGG TCGCGGATCC GGCTGCTAAC    4320

AAAGCCCGAA AGGAAGCTGA GTTGGCTGCT GCCACCGCTG AGCAATAACT AGCATAACCC    4380

CTTGGGGCCT CTAAACGGGT CTTGAGGGGT TTTTTGCTGA AAGGAGGAAC TATATCCGGA    4440

TATCCACAGG ACGGGTGTGG TCGCCATGAT CGCGTAGTCG ATAGTGGCTC CAAGTAGCGA    4500

AGCGAGCAGG ACTGGGCGGC GGCCAAAGCG GTCGGACAGT GCTCCGAGAA CGGGTGCGCA    4560

TAGAAATTGC ATCAACGCAT ATAGCGCTAG CAGCACGCCA TAGTGACTGG CGATGCTGTC    4620

GGAATGGACG ATATCCCGCA AGAGGCCCGG CAGTACCGGC ATAACCAAGC CTATGCCTAC    4680

AGCATCCAGG GTGACGGTGC CGAGGATGAC GATGAGCGCA TTGTTAGATT TCATACACGG    4740

TGCCTGACTG CGTTAGCAAT TTAACTGTGA TAAACTACCG CATTAAAGCT TATCGATGAT    4800

AAGCTGTCAA ACATGAGAA                                                4819
```

(2) INFORMATION FOR SEQ ID NO:21:

(i) SEQUENCE CHARACTERISTICS:
        (A) LENGTH: 45 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:21:

TTTACGGCCG TAAGAGATAC CTAGGGCTTT GGTGATGAAC GCGGT                45

(2) INFORMATION FOR SEQ ID NO:22:

(i) SEQUENCE CHARACTERISTICS:
        (A) LENGTH: 5574 base pairs
        (B) TYPE: nucleic acid
        (C) STRANDEDNESS: double
        (D) TOPOLOGY: circular (ii) MOLECULE TYPE: DNA (genomic)

(xi) SEQUENCE DESCRIPTION: SEQ ID NO:22:

TTCTTGAAGA CGAAAGGGCC TCGTGATACG CCTATTTTTA TAGGTTAATG TCATGATAAT      60

AATGGTTTCT TAGACGTCAG GTGGCACTTT TCGGGGAAAT GTGCGCGGAA CCCCTATTTG     120

TTTATTTTTC TAAATACATT CAAATATGTA TCCGCTCATG AGACAATAAC CCTGATAAAT     180

GCTTCAATAA TATTGAAAAA GGAAGAGTAT GAGTATTCAA CATTTCCGTG TCGCCCTTAT     240

TCCCTTTTTT GCGGCATTTT GCCTTCCTGT TTTTGCTCAC CCAGAAACGC TGGTGAAAGT     300

AAAAGATGCT GAAGATCAGT TGGGTGCACG AGTGGGTTAC ATCGAACTGG ATCTCAACAG     360

CGGTAAGATC CTTGAGAGTT TTCGCCCCGA AGAACGTTTT CCAATGATGA GCACTTTTAA     420

AGTTCTGCTA TGTGGCGCGG TATTATCCCG TGTTGACGCC GGGCAAGAGC AACTCGGTCG     480

CCGCATACAC TATTCTCAGA ATGACTTGGT TGAGTACTCA CCAGTCACAG AAAAGCATCT     540

TACGGATGGC ATGACAGTAA GAGAATTATG CAGTGCTGCC ATAACCATGA GTGATAACAC     600

TGCGGCCAAC TTACTTCTGA CAACGATCGG AGGACCGAAG GAGCTAACCG CTTTTTTGCA     660

CAACATGGGG GATCATGTAA CTCGCCTTGA TCGTTGGGAA CCGGAGCTGA ATGAAGCCAT     720

ACCAAACGAC GAGCGTGACA CCACGATGCC TGCAGCAATG GCAACAACGT TGCGCAAACT     780

ATTAACTGGC GAACTACTTA CTCTAGCTTC CCGGCAACAA TTAATAGACT GGATGGAGGC     840

GGATAAAGTT GCAGGACCAC TTCTGCGCTC GGCCCTTCCG GCTGGCTGGT TTATTGCTGA     900

TAAATCTGGA GCCGGTGAGC GTGGGTCTCG CGGTATCATT GCAGCACTGG GGCCAGATGG     960

TAAGCCCTCC CGTATCGTAG TTATCTACAC GACGGGGAGT CAGGCAACTA TGGATGAACG    1020

AAATAGACAG ATCGCTGAGA TAGGTGCCTC ACTGATTAAG CATTGGTAAC TGTCAGACCA    1080

AGTTTACTCA TATATACTTT AGATTGATTT AAAACTTCAT TTTTAATTTA AAAGGATCTA    1140

GGTGAAGATC CTTTTTGATA ATCTCATGAC CAAAATCCCT TAACGTGAGT TTTCGTTCCA    1200

CTGAGCGTCA GACCCCGTAG AAAAGATCAA AGGATCTTCT TGAGATCCTT TTTTTCTGCG    1260

CGTAATCTGC TGCTTGCAAA CAAAAAAACC ACCGCTACCA GCGGTGGTTT GTTTGCCGGA    1320

TCAAGAGCTA CCAACTCTTT TTCCGAAGGT AACTGGCTTC AGCAGAGCGC AGATACCAAA    1380

TACTGTCCTT CTAGTGTAGC CGTAGTTAGG CCACCACTTC AAGAACTCTG TAGCACCGCC    1440

TACATACCTC GCTCTGCTAA TCCTGTTACC AGTGGCTGCT GCCAGTGGCG ATAAGTCGTG    1500

TCTTACCGGG TTGGACTCAA GACGATAGTT ACCGGATAAG GCGCAGCGGT CGGGCTGAAC    1560

GGGGGGTTCG TGCACACAGC CCAGCTTGGA GCGAACGACC TACACCGAAC TGAGATACCT    1620

```
ACAGCGTGAG CATTGAGAAA GCGCCACGCT TCCCGAAGGG AGAAAGGCGG ACAGGTATCC    1680

GGTAAGCGGC AGGGTCGGAA CAGGAGAGCG CACGAGGGAG CTTCCAGGGG GAAACGCCTG    1740

GTATCTTTAT AGTCCTGTCG GGTTTCGCCA CCTCTGACTT GAGCGTCGAT TTTTGTGATG    1800

CTCGTCAGGG GGGCGGAGCC TATGGAAAAA CGCCAGCAAC GCGGCCTTTT TACGGTTCCT    1860

GGCCTTTTGC TGGCCTTTTG CTCACATGTT CTTTCCTGCG TTATCCCCTG ATTCTGTGGA    1920

TAACCGTATT ACCGCCTTTG AGTGAGCTGA TACCGCTCGC CGCAGCCGAA CGACCGAGCG    1980

CAGCGAGTCA GTGAGCGAGG AAGCGGAAGA GCGCCTGATG CGGTATTTTC TCCTTACGCA    2040

TCTGTGCGGT ATTTCACACC GCATATATGG TGCACTCTCA GTACAATCTG CTCTGATGCC    2100

GCATAGTTAA GCCAGTATAC ACTCCGCTAT CGCTACGTGA CTGGGTCATG GCTGCGCCCC    2160

GACACCCGCC AACACCCGCT GACGCGCCCT GACGGGCTTG TCTGCTCCCG GCATCCGCTT    2220

ACAGACAAGC TGTGACCGTC TCCGGGAGCT GCATGTGTCA GAGGTTTTCA CCGTCATCAC    2280

CGAAACGCGC GAGGCAGCTG CGGTAAAGCT CATCAGCGTG GTCGTGAAGC GATTCACAGA    2340

TGTCTGCCTG TTCATCCGCG TCCAGCTCGT TGAGTTTCTC CAGAAGCGTT AATGTCTGGC    2400

TTCTGATAAA GCGGGCCATG TTAAGGGCGG TTTTTTCCTG TTTGGTCACT TGATGCCTCC    2460

GTGTAAGGGG GAATTTCTGT TCATGGGGGT AATGATACCG ATGAAACGAG AGAGGATGCT    2520

CACGATACGG GTTACTGATG ATGAACATGC CCGGTTACTG GAACGTTGTG AGGGTAAACA    2580

ACTGGCGGTA TGGATGCGGC GGGACCAGAG AAAAATCACT CAGGGTCAAT GCCAGCGCTT    2640

CGTTAATACA GATGTAGGTG TTCCACAGGG TAGCCAGCAG CATCCTGCGA TGCAGATCCG    2700

GAACATAATG GTGCAGGGCG CTGACTTCCG CGTTTCCAGA CTTTACGAAA CACGGAAACC    2760

GAAGACCATT CATGTTGTTG CTCAGGTCGC AGACGTTTTG CAGCAGCAGT CGCTTCACGT    2820

TCGCTCGCGT ATCGGTGATT CATTCTGCTA ACCAGTAAGG CAACCCCGCC AGCCTAGCCG    2880

GGTCCTCAAC GACAGGAGCA CGATCATGCG CACCCGTGGC CAGGACCCAA CGCTGCCCGA    2940

GATGCGCCGC GTGCGGCTGC TGGAGATGGC GGACGCGATG GATATGTTCT GCCAAGGGTT    3000

GGTTTGCGCA TTCACAGTTC TCCGCAAGAA TTGATTGGCT CCAATTCTTG GAGTGGTGAA    3060

TCCGTTAGCG AGGTGCCGCC GGCTTCCATT CAGGTCGAGG TGGCCCGGCT CCATGCACCG    3120

CGACGCAACG CGGGGAGGCA GACAAGGTAT AGGGCGGCGC CTACAATCCA TGCCAACCCG    3180

TTCCATGTGC TCGCCGAGGC GGCATAAATC GCCGTGACGA TCAGCGGTCC AGTGATCGAA    3240

GTTAGGCTGG TAAGAGCCGC GAGCGATCCT TGAAGCTGTC CCTGATGGTC GTCATCTACC    3300

TGCCTGGACA GCATGGCCTG CAACGCGGGC ATCCCGATGC CGCCGGAAGC GAGAAGAATC    3360

ATAATGGGA AGGCCATCCA GCCTCGCGTC GCGAACGCCA GCAAGACGTA GCCCAGCGCG    3420

TCGGCCGCCA TGCCGGCGAT AATGGCCTGC TTCTCGCCGA AACGTTTGGT GGCGGGACCA    3480

GTGACGAAGG CTTGAGCGAG GGCGTGCAAG ATTCCGAATA CCGCAAGCGA CAGGCCGATC    3540

ATCGTCGCGC TCCAGCGAAA GCGGTCCTCG CCGAAAATGA CCCAGAGCGC TGCCGGCACC    3600

TGTCCTACGA GTTGCATGAT AAAGAAGACA GTCATAAGTG CGGCGACGAT AGTCATGCCC    3660

CGCGCCCACC GGAAGGAGCT GACTGGGTTG AAGGCTCTCA AGGGCATCGG TCGACGCTCT    3720

CCCTTATGCG ACTCCTGCAT TAGGAAGCAG CCCAGTAGTA GGTTGAGGCC GTTGAGCACC    3780

GCCGCCGCAA GGAATGGTGC ATGCAAGGAG ATGGCGCCCA ACAGTCCCCC GGCCACGGGG    3840

CCTGCCACCA TACCCACGCC GAAACAAGCG CTCATGAGCC CGAAGTGGCG AGCCCGATCT    3900

TCCCCATCGG TGATGTCGGC GATATAGGCG CCAGCAACCG CACCTGTGGC GCCGGTGATG    3960
```

```
CCGGCCACGA TGCGTCCGGC GTAGAGGATC GAGATCTCGA TCCCGCGAAA TTAATACGAC    4020

TCACTATAGG GAGACCACAA CGGTTTCCCT CTAGAAATAA TTTTGTTTAA CTTTAAGAAG    4080

GAGATATACA TATGGAACCG GTCGACCCGC GTCTGGAACC ATGGAAACAC CCCGGGTCCC    4140

AGCCGAAAAC CGCGTTCATC ACCAAAGCCC TAGGTATCTC TTACGGCCGT AAAAAACGTC    4200

GTCAGCGACG TCGTCCGCCG CAGGGATCTT CCATGGCCGG TGCTGGACGC ATTTACTATT    4260

CTCGCTTTGG TGACGAGGCA GCCAGATTTA GTACAACAGG GCATTACTCT GTAAGAGATC    4320

AGGACAGAGT GTATGCTGGT GTCTCATCCA CCTCTTCTGA TTTTAGAGAT CGCCCAGACG    4380

GAGTCTGGGT CGCATCCGAA GGACCTGAAG GAGACCCTGC AGGAAAAGAA GCCGAGCCAG    4440

CCCAGCCTGT CTCTTCTTTG CTCGGCTCCC CCGCCTGCGG TCCCATCAGA GCAGGCCTCG    4500

GTTGGGTACG GGACGGTCCT CGCTCGCACC CCTACAATTT TCCTGCAGGC TCGGGGGGCT    4560

CTATTCTCCG CTCTTCCTCC ACCCCGGTGC AGGGCACGGT ACCGGTGGAC TTGGCATCAA    4620

GGCAGGAAGA AGAGGAGCAG TCGCCCGACT CCACAGAGGA AGAACCAGTG ACTCTCCCAA    4680

GGCGCACCAC CAATGATGGA TTCCACCTGT TAAAGGCAGG AGGGTCATGC TTTGCTCTAA    4740

TTTCAGGAAC TGCTAACCAG GTAAAGTGCT ATCGCTTTCG GGTGAAAAAG AACCATAGAC    4800

ATCGCTACGA GAACTGCACC ACCACCTGGT TCACAGTTGC TGACAACGGT GCTGAAAGAC    4860

AAGGACAAGC ACAAATACTG ATCACCTTTG GATCGCCAAG TCAAAGGCAA GACTTTCTGA    4920

AACATGTACC ACTACCTCCT GGAATGAACA TTTCCGGCTT TACAGCCAGC TTGGACTTCT    4980

GATCACTGCC ATTGCCTTTT CTTCATCTGA CTGGTGTACT ATGCCAAATC TATGGTTTCT    5040

ATTGTTCTTG GGACTAGGAA GATCCGGCTG CTAACAAAGC CCGAAAGGAA GCTGAGTTGG    5100

CTGCTGCCAC CGCTGAGCAA TAACTAGCAT AACCCCTTGG GGCCTCTAAA CGGGTCTTGA    5160

GGGGTTTTTT GCTGAAAGGA GGAACTATAT CCGGATATCC ACAGGACGGG TGTGGTCGCC    5220

ATGATCGCGT AGTCGATAGT GGCTCCAAGT AGCGAAGCGA GCAGGACTGG GCGGCGGCCA    5280

AAGCGGTCGG ACAGTGCTCC GAGAACGGGT GCGCATAGAA ATTGCATCAA CGCATATAGC    5340

GCTAGCAGCA CGCCATAGTG ACTGGCGATG CTGTCGGAAT GGACGATATC CCGCAAGAGG    5400

CCCGGCAGTA CCGGCATAAC CAAGCCTATG CCTACAGCAT CCAGGGTGAC GGTGCCGAGG    5460

ATGACGATGA GCGCATTGTT AGATTTCATA CACGGTGCCT GACTGCGTTA GCAATTTAAC    5520

TGTGATAAAC TACCGCATTA AAGCTTATCG ATGATAAGCT GTCAAACATG AGAA          5574
```

(2) INFORMATION FOR SEQ ID NO:23:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (xi) SEQUENCE DESCRIPTION: SEQ ID NO:23:

```
GATCCCAGAC CCACCAGGTT                                                  20
```

(2) INFORMATION FOR SEQ ID NO:24:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:24:

GAACCTGGTG GGTCTGG                                                                      17

(2) INFORMATION FOR SEQ ID NO:25:

(i) SEQUENCE CHARACTERISTICS:
            (A) LENGTH: 50 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:25:

CGTCCGCCGC AGGGATCGCA GACCCACCAG GTTTCTCTGT CTAAACAGGC                                   50

(2) INFORMATION FOR SEQ ID NO:26:

(i) SEQUENCE CHARACTERISTICS:
            (A) LENGTH: 58 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:26:

CATGGCCTGT TTAGACAGAG AAACCTGGTG GGTCTGCGAT CCCTGCGGCG GACGACGT                          58

(2) INFORMATION FOR SEQ ID NO:27:

(i) SEQUENCE CHARACTERISTICS:
            (A) LENGTH: 48 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:27:

CATGTACGGC CGTAAAAAAC GTCGTCAGCG ACGTCGTCCG CCGGACAC                                     48

(2) INFORMATION FOR SEQ ID NO:28:

(i) SEQUENCE CHARACTERISTICS:
            (A) LENGTH: 46 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:28:

CGGTGTCCGG CGGACGACGT CGCTGACGAC GTTTTTTACG GCCGTA                                       46

(2) INFORMATION FOR SEQ ID NO:29:

(i) SEQUENCE CHARACTERISTICS:
            (A) LENGTH: 26 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:29:

ATCATCGATA AGCTTTAATG CGGTAG                    26

(2) INFORMATION FOR SEQ ID NO:30:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:30:

ACTTTAAGAA GGAGATATAC ATATGTTCAT CACCAAAGCC CTAGGTATCT CT    52

(2) INFORMATION FOR SEQ ID NO:31:

(i) SEQUENCE CHARACTERISTICS:
        (A) LENGTH: 51 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:31:

ACTTTAAGAA GGAGATATAC ATATGTACGG CCGTAAAAAA CGTCGTCAGC G     51

(2) INFORMATION FOR SEQ ID NO:32:

(i) SEQUENCE CHARACTERISTICS:
        (A) LENGTH: 52 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:32:

AACGTCGTCA GCGACGTCGT CCGCCGGACA CCGGAAACCC CTGCCACACC AC    52

(2) INFORMATION FOR SEQ ID NO:33:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:33:

CGAAAAGTGC CACCTGACGT CTAAGAAACC                30

(2) INFORMATION FOR SEQ ID NO:34:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:34:

CTCCCATGGC TAGCAACACT ACACCC                    26

(2) INFORMATION FOR SEQ ID NO:35:

(i) SEQUENCE CHARACTERISTICS:
        (A) LENGTH: 10 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:35:

GAAGATCTTC                                                             10

(2) INFORMATION FOR SEQ ID NO:36:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:36:

CAGAGGAAGC CATGGTGACT CTCCCAA                                          27

(2) INFORMATION FOR SEQ ID NO:37:

(i) SEQUENCE CHARACTERISTICS:
        (A) LENGTH: 27 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:37:

AAGGCAATGG ATCCGATCAG AAGTCCA                                          27

(2) INFORMATION FOR SEQ ID NO:38:

(i) SEQUENCE CHARACTERISTICS:
        (A) LENGTH: 134 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:38:

Met Tyr Gly Arg Lys Lys Arg Gln Arg Arg Pro Pro Asp Thr
1               5                   10                  15

Gly Asn Pro Cys His Thr Thr Lys Leu Leu His Arg Asp Ser Val Asp
                20                  25                  30

Ser Ala Pro Ile Leu Thr Ala Phe Asn Ser Ser His Lys Gly Arg Ile
            35                  40                  45

Asn Cys Asn Ser Asn Thr Thr Pro Ile Val His Leu Lys Gly Asp Ala
        50                  55                  60

Asn Thr Leu Lys Cys Leu Arg Tyr Arg Phe Lys Lys His Cys Thr Leu
65                  70                  75                  80

Tyr Thr Ala Val Ser Ser Thr Trp His Trp Thr Gly His Asn Val Lys
                85                  90                  95

His Lys Ser Ala Ile Val Thr Leu Thr Tyr Asp Ser Glu Trp Gln Arg
            100                 105                 110

Asp Gln Phe Leu Ser Gln Val Lys Ile Pro Lys Thr Ile Thr Val Ser

```
                    115                 120                 125
Thr Gly Phe Met Ser Ile
    130

(2) INFORMATION FOR SEQ ID NO:39:

(i) SEQUENCE CHARACTERISTICS:
         (A) LENGTH: 55 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:39:

CATGTACGGC CGTAAAAAAC GTCGTCAGCG ACGTCGTCCG CTGAGTCAGG CCCAG              55

(2) INFORMATION FOR SEQ ID NO:40:

(i) SEQUENCE CHARACTERISTICS:
         (A) LENGTH: 51 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:40:

CTGGGCCTGA CTCAGCGGAC GACGTCGCTG ACGACGTTTT TTACGGCCGT A                  51

(2) INFORMATION FOR SEQ ID NO:41:

(i) SEQUENCE CHARACTERISTICS:
         (A) LENGTH: 46 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:41:

TCCTTCCTGT CCGCTGGTCA GCGCCCGCGC CGCCTGTCCA CCTAAG                        46

(2) INFORMATION FOR SEQ ID NO:42:

(i) SEQUENCE CHARACTERISTICS:
         (A) LENGTH: 54 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:42:

AATTCTTAGG TGGACAGGCG GCGCGGGCGC TGACCAGCGG ACAGGAAGGA CATG               54

(2) INFORMATION FOR SEQ ID NO:43:

(i) SEQUENCE CHARACTERISTICS:
         (A) LENGTH: 39 base pairs
         (B) TYPE: nucleic acid
         (C) STRANDEDNESS: single
         (D) TOPOLOGY: linear (ii) MOLECULE TYPE: DNA (genomic)

(xi) SEQUENCE DESCRIPTION: SEQ ID NO:43:

GGGGACTTTC CGCTGGGGAC TTTCCACGGG GGACTTTCC                                39
```

(2) INFORMATION FOR SEQ ID NO:44:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:44:

```
GGAAAGTCCC CCGTGGAAAG TCCCCAGCGG AAAGTCCCC                    39
```

(2) INFORMATION FOR SEQ ID NO:45:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:45:

```
GTCTACTTTC CGCTGTCTAC TTTCCACGGT CTACTTTCC                    39
```

(2) INFORMATION FOR SEQ ID NO:46:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:46:

```
GGAAAGTAGA CCGTGGAAAG TAGACAGCGG AAAGTAGAC                    39
```

(2) INFORMATION FOR SEQ ID NO:47:

(i) SEQUENCE CHARACTERISTICS:
        (A) LENGTH: 12 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:47:

```
Tyr Gly Arg Lys Lys Arg Arg Gln Arg Arg Pro
1               5                   10
```

(2) INFORMATION FOR SEQ ID NO:48:

(i) SEQUENCE CHARACTERISTICS:
        (A) LENGTH: 26 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:48:

```
Tyr Gly Arg Lys Lys Arg Arg Gln Arg Arg Pro Pro Gln Gly Ser
1               5                   10                  15

Gln Thr His Gln Val Ser Leu Ser Lys Gln
```

(2) INFORMATION FOR SEQ ID NO:49:

(i) SEQUENCE CHARACTERISTICS:
        (A) LENGTH: 35 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:49:

```
Phe Ile Thr Lys Ala Leu Gly Ile Ser Tyr Gly Arg Lys Lys Arg Arg
1               5                   10                  15
Gln Arg Arg Pro Pro Gln Gly Ser Gln Thr His Gln Val Ser Leu
            20                  25                  30
Ser Lys Gln
        35
```

(2) INFORMATION FOR SEQ ID NO:50:

(i) SEQUENCE CHARACTERISTICS:
        (A) LENGTH: 21 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:50:

```
Phe Ile Thr Lys Ala Leu Gly Ile Ser Tyr Gly Arg Lys Lys Arg Arg
1               5                   10                  15
Gln Arg Arg Pro
            20
```

(2) INFORMATION FOR SEQ ID NO:51:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:51:

```
Pro Asp Thr Gly Asn Pro Cys His Thr Thr Lys Leu Leu His Arg Asp
1               5                   10                  15
Ser Val Asp Ser Ala Pro Ile Leu Thr Ala Phe Asn Ser Ser His Lys
            20                  25                  30
Gly Arg Ile Asn Cys Asn Ser Asn Thr Thr Pro Ile Val His Leu Lys
        35                  40                  45
Gly Asp Ala Asn Thr Leu Lys Cys Leu Arg Tyr Arg Phe Lys Lys His
    50                  55                  60
Cys Thr Leu Tyr Thr Ala Val Ser Ser Thr Trp His Trp Thr Gly His
65                  70                  75                  80
Asn Val Lys His Lys Ser Ala Ile Val Thr Leu Thr Tyr Asp Ser Glu
                85                  90                  95
Trp Gln Arg Asp Gln Phe Leu Ser Gln Val Lys Ile Pro Lys Thr Ile
            100                 105                 110
Thr Val Ser Thr Gly Phe Met Ser Ile
            115                 120
```

(2) INFORMATION FOR SEQ ID NO:52:

(i) SEQUENCE CHARACTERISTICS:
        (A) LENGTH: 15 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:52:

```
Gly Arg Lys Lys Arg Arg Gln Arg Arg Pro Pro Gln Gly Ser
1               5                   10                  15
```

(2) INFORMATION FOR SEQ ID NO:53:

(i) SEQUENCE CHARACTERISTICS:
        (A) LENGTH: 25 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:53:

```
Phe Ile Thr Lys Ala Leu Gly Ile Ser Tyr Gly Arg Lys Lys Arg Arg
1               5                   10                  15
Gln Arg Arg Pro Pro Gln Gly Ser
            20              25
```

(2) INFORMATION FOR SEQ ID NO:54:

(i) SEQUENCE CHARACTERISTICS:
        (A) LENGTH: 85 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:54:

```
Cys Asn Ser Asn Thr Thr Pro Ile Val His Leu Lys Gly Asp Ala Asn
1               5                   10                  15

Thr Leu Lys Cys Leu Arg Tyr Arg Phe Lys Lys His Cys Thr Leu Tyr
                20                  25                  30

Thr Ala Val Ser Ser Thr Trp His Trp Thr Gly His Asn Val Lys His
            35                  40                  45

Lys Ser Ala Ile Val Thr Leu Thr Tyr Asp Ser Glu Trp Gln Arg Asp
    50                  55                  60

Gln Phe Leu Ser Gln Val Lys Ile Pro Lys Thr Ile Thr Val Ser Thr
65                  70                  75                  80

Gly Phe Met Ser Ile
                85
```

(2) INFORMATION FOR SEQ ID NO:55:

(i) SEQUENCE CHARACTERISTICS:
        (A) LENGTH: 121 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:55:

```
Pro Asp Thr Gly Asn Pro Cys His Thr Thr Lys Leu Leu His Arg Asp
1               5                   10                  15

Ser Val Asp Ser Ala Pro Ile Leu Thr Ala Phe Asn Ser Ser His Lys
            20                  25                  30

Gly Arg Ile Asn Cys Asn Ser Asn Thr Thr Pro Ile Val His Leu Lys
            35                  40                  45

Gly Asp Ala Asn Thr Leu Lys Ser Leu Arg Tyr Arg Phe Lys Lys His
            50                  55                  60

Ser Thr Leu Tyr Thr Ala Val Ser Ser Thr Trp His Trp Thr Gly His
65                  70                  75                  80

Asn Val Lys His Lys Ser Ala Ile Val Thr Leu Thr Tyr Asp Ser Glu
            85                  90                  95

Trp Gln Arg Asp Gln Phe Leu Ser Gln Val Lys Ile Pro Lys Thr Ile
            100                 105                 110

Thr Val Ser Thr Gly Phe Met Ser Ile
            115                 120
```

(2) INFORMATION FOR SEQ ID NO:56:

(i) SEQUENCE CHARACTERISTICS:
        (A) LENGTH: 161 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:56:

```
Leu Gly Trp Val Arg Asp Gly Pro Arg Ser His Pro Tyr Asn Phe Pro
1               5                   10                  15

Ala Gly Ser Gly Gly Ser Ile Leu Arg Ser Ser Ser Thr Pro Val Gln
            20                  25                  30

Gly Thr Val Pro Val Asp Leu Ala Ser Arg Gln Glu Glu Glu Glu Gln
            35                  40                  45

Ser Pro Asp Ser Thr Glu Glu Glu Pro Val Thr Leu Pro Arg Arg Thr
            50                  55                  60

Thr Asn Asp Gly Phe His Leu Leu Lys Ala Gly Gly Ser Cys Phe Ala
65                  70                  75                  80

Leu Ile Ser Gly Thr Ala Asn Gln Val Lys Cys Tyr Arg Phe Arg Val
            85                  90                  95

Lys Lys Asn His Arg His Arg Tyr Glu Asn Cys Thr Thr Thr Trp Phe
            100                 105                 110

Thr Val Ala Asp Asn Gly Ala Glu Arg Gln Gly Gln Ala Gln Ile Leu
            115                 120                 125

Ile Thr Phe Gly Ser Pro Ser Gln Arg Gln Asp Phe Leu Lys His Val
            130                 135                 140

Pro Leu Pro Pro Gly Met Asn Ile Ser Gly Phe Thr Ala Ser Leu Asp
145                 150                 155                 160

Phe
```

(2) INFORMATION FOR SEQ ID NO:57:

(i) SEQUENCE CHARACTERISTICS:
        (A) LENGTH: 249 amino acids
        (B) TYPE: amino acid
        (C) STRANDEDNESS: single
        (D) TOPOLOGY: linear -continued (ii) MOLECULE TYPE: protein (xi) SEQUENCE DESCRIPTION: SEQ ID NO:57:

```
Met Ala Gly Ala Gly Arg Ile Tyr Tyr Ser Arg Phe Gly Asp Glu Ala
1               5                   10                  15

Ala Arg Phe Ser Thr Thr Gly His Tyr Ser Val Arg Asp Gln Asp Arg
                20                  25                  30

Val Tyr Ala Gly Val Ser Ser Thr Ser Ser Asp Phe Arg Asp Arg Pro
            35                  40                  45

Asp Gly Val Trp Val Ala Ser Glu Gly Pro Glu Gly Asp Pro Ala Gly
        50                  55                  60

Lys Glu Ala Glu Pro Ala Gln Pro Val Ser Ser Leu Leu Gly Ser Pro
65                  70                  75                  80

Ala Cys Gly Pro Ile Arg Ala Gly Leu Gly Trp Val Arg Asp Gly Pro
                85                  90                  95

Arg Ser His Pro Tyr Asn Phe Pro Ala Gly Ser Gly Ser Ile Leu
                100                 105                 110

Arg Ser Ser Ser Thr Pro Val Gln Gly Thr Val Pro Val Asp Leu Ala
            115                 120                 125

Ser Arg Gln Glu Glu Glu Gln Ser Pro Asp Ser Thr Glu Glu Glu
    130                 135                 140

Pro Val Thr Leu Pro Arg Arg Thr Thr Asn Asp Gly Phe His Leu Leu
145                 150                 155                 160

Lys Ala Gly Gly Ser Cys Phe Ala Leu Ile Ser Gly Thr Ala Asn Gln
                165                 170                 175

Val Lys Cys Tyr Arg Phe Arg Val Lys Lys Asn His Arg His Arg Tyr
            180                 185                 190

Glu Asn Cys Thr Thr Thr Trp Phe Thr Val Ala Asp Asn Gly Ala Glu
            195                 200                 205

Arg Gln Gly Gln Ala Gln Ile Leu Ile Thr Phe Gly Ser Pro Ser Gln
    210                 215                 220

Arg Gln Asp Phe Leu Lys His Val Pro Leu Pro Pro Gly Met Asn Ile
225                 230                 235                 240

Ser Gly Phe Thr Ala Ser Leu Asp Phe
                245
```

(2) INFORMATION FOR SEQ ID NO:58:

(i) SEQUENCE CHARACTERISTICS:
      (A) LENGTH: 385 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO:58:

```
Met Tyr Gly Arg Lys Lys Arg Gln Arg Arg Arg Pro Leu Ser Gln
1               5                   10                  15

Ala Gln Leu Met Pro Ser Pro Met Pro Val Pro Ala Ala Leu
                20                  25                  30

Phe Asn Arg Leu Leu Asp Asp Leu Gly Phe Ser Ala Gly Pro Ala Leu
            35                  40                  45

Cys Thr Met Leu Asp Thr Trp Asn Glu Asp Leu Phe Ser Gly Phe Pro
        50                  55                  60

Thr Asn Ala Asp Met Tyr Arg Glu Cys Lys Phe Leu Ser Thr Leu Pro
65                  70                  75                  80
```

```
Ser Asp Val Ile Asp Trp Gly Asp Ala His Val Pro Glu Arg Ser Pro
             85                  90                  95
Ile Asp Ile Arg Ala His Gly Asp Val Ala Phe Pro Thr Leu Pro Ala
            100                 105                 110
Thr Arg Asp Glu Leu Pro Ser Tyr Tyr Glu Ala Met Ala Gln Phe Phe
            115                 120                 125
Arg Gly Glu Leu Arg Ala Arg Glu Glu Ser Tyr Arg Thr Val Leu Ala
            130                 135                 140
Asn Phe Cys Ser Ala Leu Tyr Arg Tyr Leu Arg Ala Ser Val Arg Gln
145                 150                 155                 160
Leu His Arg Gln Ala His Met Arg Gly Arg Asn Arg Asp Leu Arg Glu
            165                 170                 175
Met Leu Arg Thr Thr Ile Ala Asp Arg Tyr Tyr Arg Glu Thr Ala Arg
            180                 185                 190
Leu Ala Arg Val Leu Phe Leu His Leu Tyr Leu Phe Leu Ser Arg Glu
            195                 200                 205
Ile Leu Trp Ala Ala Tyr Ala Glu Gln Met Met Arg Pro Asp Leu Phe
            210                 215                 220
Asp Gly Leu Cys Cys Asp Leu Glu Ser Trp Arg Gln Leu Ala Cys Leu
225                 230                 235                 240
Phe Gln Pro Leu Met Phe Ile Asn Gly Ser Leu Thr Val Arg Gly Val
            245                 250                 255
Pro Val Glu Ala Arg Arg Leu Arg Glu Leu Asn His Ile Arg Glu His
            260                 265                 270
Leu Asn Leu Pro Leu Val Arg Ser Ala Ala Ala Glu Glu Pro Gly Ala
            275                 280                 285
Pro Leu Thr Thr Pro Pro Val Leu Gln Gly Asn Gln Ala Arg Ser Ser
            290                 295                 300
Gly Tyr Phe Met Leu Leu Ile Arg Ala Lys Leu Asp Ser Tyr Ser Ser
305                 310                 315                 320
Val Ala Thr Ser Glu Gly Glu Ser Val Met Arg Glu His Ala Tyr Ser
            325                 330                 335
Arg Gly Arg Thr Arg Asn Asn Tyr Gly Ser Thr Ile Glu Gly Leu Leu
            340                 345                 350
Asp Leu Pro Asp Asp Asp Ala Pro Ala Glu Ala Gly Leu Val Ala
            355                 360                 365
Pro Arg Met Ser Phe Leu Ser Ala Gly Gln Arg Pro Arg Arg Leu Ser
            370                 375                 380
Thr
385

(2) INFORMATION FOR SEQ ID NO:59:

(i) SEQUENCE CHARACTERISTICS:
        (A) LENGTH: 148 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:59:

Met Tyr Gly Arg Lys Lys Arg Arg Gln Arg Arg Pro Pro Gln Gly
1               5                   10                  15
Ser Gln Thr His Gln Val Ser Leu Ser Lys Gln Pro Asp Thr Gly Asn
            20                  25                  30
```

Pro Cys His Thr Thr Lys Leu Leu His Arg Asp Ser Val Asp Ser Ala
         35                  40                  45

Pro Ile Leu Thr Ala Phe Asn Ser Ser His Lys Gly Arg Ile Asn Cys
         50                  55                  60

Asn Ser Asn Thr Thr Pro Ile Val His Leu Lys Gly Asp Ala Asn Thr
65                   70                  75                  80

Leu Lys Cys Leu Arg Tyr Arg Phe Lys Lys His Cys Thr Leu Tyr Thr
                 85                  90                  95

Ala Val Ser Ser Thr Trp His Trp Thr Gly His Asn Val Lys His Lys
                 100                 105                 110

Ser Ala Ile Val Thr Leu Thr Tyr Asp Ser Glu Trp Gln Arg Asp Gln
             115                 120                 125

Phe Leu Ser Gln Val Lys Ile Pro Lys Thr Ile Thr Val Ser Thr Gly
         130                 135                 140

Phe Met Ser Ile
145

(2) INFORMATION FOR SEQ ID NO:60:

(i) SEQUENCE CHARACTERISTICS:
        (A) LENGTH: 157 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:60:

Met Phe Ile Thr Lys Ala Leu Gly Ile Ser Tyr Gly Arg Lys Lys Arg
1               5                   10                  15

Arg Gln Arg Arg Arg Pro Pro Gln Gly Ser Gln Thr His Gln Val Ser
                 20                  25                  30

Leu Ser Lys Gln Pro Asp Thr Gly Asn Pro Cys His Thr Thr Lys Leu
             35                  40                  45

Leu His Arg Asp Ser Val Asp Ser Ala Pro Ile Leu Thr Ala Phe Asn
         50                  55                  60

Ser Ser His Lys Gly Arg Ile Asn Cys Asn Ser Asn Thr Thr Pro Ile
65                   70                  75                  80

Val His Leu Lys Gly Asp Ala Asn Thr Leu Lys Cys Leu Arg Tyr Arg
                 85                  90                  95

Phe Lys Lys His Cys Thr Leu Tyr Thr Ala Val Ser Ser Thr Trp His
                 100                 105                 110

Trp Thr Gly His Asn Val Lys His Lys Ser Ala Ile Val Thr Leu Thr
             115                 120                 125

Tyr Asp Ser Glu Trp Gln Arg Asp Gln Phe Leu Ser Gln Val Lys Ile
         130                 135                 140

Pro Lys Thr Ile Thr Val Ser Thr Gly Phe Met Ser Ile
145                 150                 155

(2) INFORMATION FOR SEQ ID NO:61:

(i) SEQUENCE CHARACTERISTICS:
        (A) LENGTH: 177 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:61:

```
Met Gly Arg Lys Lys Arg Arg Gln Arg Arg Pro Pro Gln Gly Ser
1               5                   10                  15

Leu Gly Trp Val Arg Asp Gly Pro Arg Ser His Pro Tyr Asn Phe Pro
                20                  25                  30

Ala Gly Ser Gly Gly Ser Ile Leu Arg Ser Ser Thr Pro Val Gln
            35                  40                  45

Gly Thr Val Pro Val Asp Leu Ala Ser Arg Gln Glu Glu Glu Gln
50                  55                  60

Ser Pro Asp Ser Thr Glu Glu Pro Val Thr Leu Pro Arg Arg Thr
65                  70                  75                  80

Thr Asn Asp Gly Phe His Leu Leu Lys Ala Gly Gly Ser Cys Phe Ala
                85                  90                  95

Leu Ile Ser Gly Thr Ala Asn Gln Val Lys Cys Tyr Arg Phe Arg Val
                100                 105                 110

Lys Lys Asn His Arg His Arg Tyr Glu Asn Cys Thr Thr Thr Trp Phe
            115                 120                 125

Thr Val Ala Asp Asn Gly Ala Glu Arg Gln Gly Gln Ala Gln Ile Leu
130                 135                 140

Ile Thr Phe Gly Ser Pro Ser Gln Arg Gln Asp Phe Leu Lys His Val
145                 150                 155                 160

Pro Leu Pro Pro Gly Met Asn Ile Ser Gly Phe Thr Ala Ser Leu Asp
                165                 170                 175

Phe
```

(2) INFORMATION FOR SEQ ID NO:62:

(i) SEQUENCE CHARACTERISTICS:
        (A) LENGTH: 187 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:62:

```
Met Phe Ile Thr Lys Ala Leu Gly Ile Ser Tyr Gly Arg Lys Lys Arg
1               5                   10                  15

Arg Gln Arg Arg Arg Pro Pro Gln Gly Ser Leu Gly Trp Val Arg Asp
                20                  25                  30

Gly Pro Arg Ser His Pro Tyr Asn Phe Pro Ala Gly Ser Gly Gly Ser
            35                  40                  45

Ile Leu Arg Ser Ser Ser Thr Pro Val Gln Gly Thr Val Pro Val Asp
50                  55                  60

Leu Ala Ser Arg Gln Glu Glu Glu Gln Ser Pro Asp Ser Thr Glu
65                  70                  75                  80

Glu Glu Pro Val Thr Leu Pro Arg Arg Thr Thr Asn Asp Gly Phe His
                85                  90                  95

Leu Leu Lys Ala Gly Gly Ser Cys Phe Ala Leu Ile Ser Gly Thr Ala
                100                 105                 110

Asn Gln Val Lys Cys Tyr Arg Phe Arg Val Lys Lys Asn His Arg His
            115                 120                 125

Arg Tyr Glu Asn Cys Thr Thr Thr Trp Phe Thr Val Ala Asp Asn Gly
            130                 135                 140

Ala Glu Arg Gln Gly Gln Ala Gln Ile Leu Ile Thr Phe Gly Ser Pro
145                 150                 155                 160
```

Ser Gln Arg Gln Asp Phe Leu Lys His Val Pro Leu Pro Pro Gly Met
            165                 170                 175

Asn Ile Ser Gly Phe Thr Ala Ser Leu Asp Phe
            180                 185

(2) INFORMATION FOR SEQ ID NO:63:

(i) SEQUENCE CHARACTERISTICS:
        (A) LENGTH: 143 amino acids
        (B) TYPE: amino acid
        (C) STRANDEDNESS: single
        (D) TOPOLOGY: linear (ii) MOLECULE TYPE: protein (xi) SEQUENCE DESCRIPTION: SEQ ID NO:63:

Met Phe Ile Thr Lys Ala Leu Gly Ile Ser Tyr Gly Arg Lys Lys Arg
1               5                   10                  15

Arg Gln Arg Arg Arg Pro Pro Asp Thr Gly Asn Pro Cys His Thr Thr
                20                  25                  30

Lys Leu Leu His Arg Asp Ser Val Asp Ser Ala Pro Ile Leu Thr Ala
            35                  40                  45

Phe Asn Ser Ser His Lys Gly Arg Ile Asn Cys Asn Ser Asn Thr Thr
50                  55                  60

Pro Ile Val His Leu Lys Gly Asp Ala Asn Thr Leu Lys Cys Leu Arg
65                  70                  75                  80

Tyr Arg Phe Lys Lys His Cys Thr Leu Tyr Thr Ala Val Ser Ser Thr
                85                  90                  95

Trp His Trp Thr Gly His Asn Val Lys His Lys Ser Ala Ile Val Thr
            100                 105                 110

Leu Thr Tyr Asp Ser Glu Trp Gln Arg Asp Gln Phe Leu Ser Gln Val
            115                 120                 125

Lys Ile Pro Lys Thr Ile Thr Val Ser Thr Gly Phe Met Ser Ile
            130                 135                 140

(2) INFORMATION FOR SEQ ID NO:64:

(i) SEQUENCE CHARACTERISTICS:
        (A) LENGTH: 46 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:64:

CGTCCGCCGC AGGGATCCCA GACCCACCAG GTTCCGGTTA CTCTGC                46

(2) INFORMATION FOR SEQ ID NO:65:

(i) SEQUENCE CHARACTERISTICS:
        (A) LENGTH: 54 base pairs
        (B) TYPE: nucleic acid
        (C) STRANDEDNESS: single
        (D) TOPOLOGY: linear (ii) MOLECULE TYPE: DNA (genomic)

(xi) SEQUENCE DESCRIPTION: SEQ ID NO:65:

CTTGGCAGAG TAACCGGAAC CTGGTGGGTC TGGGATCCCT GCGGCGGACG ACGT        54

(2) INFORMATION FOR SEQ ID NO:66:

```
        (i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:66:

CTAGTGGCTC GAGATTCCG                                                        19

(2) INFORMATION FOR SEQ ID NO:67:

(i) SEQUENCE CHARACTERISTICS:
            (A) LENGTH: 19 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:67:

GATCCGGAAT CTCGAGCCA                                                        19

(2) INFORMATION FOR SEQ ID NO:68:

(i) SEQUENCE CHARACTERISTICS:
            (A) LENGTH: 22 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:68:

CTCGAGAAGC TTGACGGATC CG                                                    22

(2) INFORMATION FOR SEQ ID NO:69:

(i) SEQUENCE CHARACTERISTICS:
            (A) LENGTH: 30 base pairs
            (B) TYPE: nucleic acid
            (C) STRANDEDNESS: single
            (D) TOPOLOGY: linear (ii) MOLECULE TYPE: DNA (genomic)

(xi) SEQUENCE DESCRIPTION: SEQ ID NO:69:

AATTCGGATC CGTCAAGCTT CTCGAGACGT                                            30
```